US010786587B1

(12) United States Patent
Ricciardi et al.

(10) Patent No.: US 10,786,587 B1
(45) Date of Patent: Sep. 29, 2020

(54) METHOD AND APPARATUS FOR CLEANING AND TREATING HVAC SYSTEMS WITH A DEPLOYED AGENT

(71) Applicants: Jonathan J. Ricciardi, Wausau, WI (US); Carl L. Ricciardi, Tomahawk, WI (US)

(72) Inventors: Jonathan J. Ricciardi, Wausau, WI (US); Carl L. Ricciardi, Tomahawk, WI (US)

( * ) Notice: Subject to any disclaimer, the term of this patent is extended or adjusted under 35 U.S.C. 154(b) by 0 days.

(21) Appl. No.: 16/729,620

(22) Filed: Dec. 30, 2019

Related U.S. Application Data

(63) Continuation-in-part of application No. 16/561,068, filed on Sep. 5, 2019, which is a continuation-in-part
(Continued)

(51) Int. Cl.
*A61L 2/22* (2006.01)
*A61L 2/20* (2006.01)
(Continued)

(52) U.S. Cl.
CPC ............... *A61L 2/20* (2013.01); *A61L 2/022* (2013.01); *A61L 2/208* (2013.01); *A61L 2/22* (2013.01);
(Continued)

(58) Field of Classification Search
CPC . A61L 2/20; A61L 2/202; A61L 2/208; A61L 2/22; A61L 9/14; A61L 9/015; A61L 9/03; A61L 9/032; A61L 9/12; A61L 9/122; A61L 2209/16; A61L 2202/00; A61L 2209/00; A61L 2209/13; A61L 2209/211;
(Continued)

(56) References Cited

U.S. PATENT DOCUMENTS

| 4,829,882 A * | 5/1989 | Jackson | ............... E02D 31/008 |
| | | | 236/49.1 |
| 5,878,355 A * | 3/1999 | Berg | .................. B01J 13/0095 |
| | | | 427/212 |

(Continued)

OTHER PUBLICATIONS

Samuel C. Sugarman, HVAC Fundamentals 10-12 (3rd ed. Fairmont Press 2016). (Year: 2016).*
(Continued)

*Primary Examiner* — Mikhail Kornakov
*Assistant Examiner* — Richard Z. Zhang
(74) *Attorney, Agent, or Firm* — Donald J. Ersler

(57) ABSTRACT

A method and apparatus for cleaning and treating HVAC systems with a deployed agent preferably includes an aerosol generating device, a plurality of vent sealing devices, an outlet connection conduit and an inlet connection conduit. The HVAC system includes at least one supply duct and at least one return duct. The aerosol generating device includes an inlet and an outlet. The outlet is connected to a return vent of the at least one return duct with the outlet connection conduit. A supply vent of the at least one supply duct may be connected to the inlet with the inlet connection conduit. However, the inlet does not have to be connected to the supply vent if the aerosol generating device is retained in an enclosure. A booster chamber may be used to increase the flow rate of the deployed agent from the aerosol generating device.

17 Claims, 27 Drawing Sheets

Related U.S. Application Data of application No. 14/886,124, filed on Oct. 19, 2015, now Pat. No. 10,436,462.

(51) Int. Cl.

| | |
|---|---|
| *A61L 2/02* | (2006.01) |
| *A61L 9/015* | (2006.01) |
| *A61L 9/14* | (2006.01) |
| *B08B 9/032* | (2006.01) |
| *F24F 13/08* | (2006.01) |

(52) U.S. Cl.
 CPC ................. *A61L 9/015* (2013.01); *A61L 9/14* (2013.01); *B08B 9/0322* (2013.01); *F24F 13/08* (2013.01); *F24F 2221/22* (2013.01)

(58) Field of Classification Search
 CPC ................. F24F 3/16; F24F 2003/1664; F24F 2003/1671; F24F 2003/1675; F24F 2003/1685; F24F 11/74; F24F 11/745; F24F 7/04–10; F24F 7/007; F24F 2221/22; F24F 3/08; F24F 11/75; F24F 2110/30; B08B 9/0322
 See application file for complete search history.

(56) References Cited

U.S. PATENT DOCUMENTS

| | | | |
|---|---|---|---|
| 8,359,984 B1* | 1/2013 | Wolf, II | ................... A61L 9/14 108/147.19 |
| 2004/0146437 A1* | 7/2004 | Arts | .......................... A61L 2/10 422/186.07 |
| 2011/0114744 A1* | 5/2011 | Ricciardi | ................... A61L 2/22 239/4 |

OTHER PUBLICATIONS

Google Image search for "booster fan" on Feb. 9, 2020. (Year: 2020).*

* cited by examiner

METHOD AND APPARATUS FOR CLEANING AND TREATING HVAC SYSTEMS WITH A DEPLOYED AGENT

CROSS-REFERENCES TO RELATED APPLICATIONS

This is a continuation-in-part patent application, which takes priority from patent application Ser. No. 16/561,068, filed on September, which takes priority from patent application Ser. No. 14/886,124, filed on Oct. 19, 2015, now U.S. Pat. No. 10,436,462 issued on Oct. 8, 2019, which are herein incorporated by reference in their entirety.

BACKGROUND OF THE INVENTION

Field of the Invention

The present invention relates generally to the cleaning and decontamination of the interior of various air duct(s) and/or HVAC part(s) by connecting any air entry vent(s) and air exit vent(s) in room(s) and area(s) of a building(s) using one or more vent bypass system(s) to connect the various ductwork and/or supply and return air duct(s) in an HVAC system(s), and allowing deployed airborne agent(s) to be flowed through the interconnected system of various connected air duct(s), conduit(s), and/or any other HVAC part(s) and related equipment(s) for their sanitization, disinfection, sterilization, and/or decontamination. Additionally, the present invention relates generally to an enhanced aerosol and/or vapor generator design where airflow is directed into and/or through preferably both the one or more aerosol(s), gas(s), and/or vapor(s) generator(s), and the at least one common pressurized chamber(s) in which the said generated aerosol(s), gas(s), and/or vapor(s), are flowed into after being generated or created, and where these said aerosol(s), gas(s), and/or vapor(s), is then flowed out of the said one or more pressurized chamber(s) and into the various targeted, enclosure(s), space(s), conduit(s) and/or airduct(s), overcoming a delinquency in many aerosol and/or vapor generator designs where an effective air/gas(s) flow is not provided or generated to deploy any, aerosol, gas(s), and/or vapor(s), effectively into any, enclosure(s), space(s), conduit(s) and/or air duct(s) with one or more of any attributes such as, but not limited to any, large volume area(s), areas with complex geometries, and/or area(s) and space(s) with long horizontal and/or vertical runs. Finally, the present invention also relates to an enhanced vent bypass system that can treat, decontaminate, dehumidify, remove unwanted vapor(s) or gas(s), and/or dry, various air duct(s), conduit(s), HVAC system(s), and/or any other HVAC part(s) and related equipment(s).

Discussion of the Prior Art

A vent cover is placed over a heating/cooling vent, which is a portion of a HVAC system, when a hospital room is disinfected. Automation of the vent covering process speeds up the disinfection process. U.S. Pat. No. 8,359,984 ('984 patent) to Wolf II et al. discloses a portable automated vent cover. U.S. Pat. No. 8,359,984 is herein incorporated into this patent application by reference in its entirety. However, the vent cover door of the '984 patent does not always release from a vent opening without manual intervention on the part of an operator, because the vacuum in the vent retains the vent cover door against the vent opening. U.S. Pat. No. 9,789,508 to Baumgartner et al. and U.S. Pat. No. 7,641,130 to Ricciardi et al. are hereby incorporated by reference in their entirety.

SUMMARY OF THE INVENTION

An apparatus and method of an embodiment of the present invention, briefly summarized and without limitation, comprises the use of a vent bypass system to provide the treatment of, and more preferably and without limitation, the decontamination of, various surfaces inside of various connected and/or indirectly connected ductwork, air ducts, connected air supply ducts, air return ducts, HVAC equipment, entire HVAC systems and associated ducting, and/or any other connected and/or related parts that can be, without limitation, connected to various parts and equipment used for heating, ventilation, cooling, movement, distribution, and/or filtering, of air and/or gas(s), that is supplied to one or more room(s), various rooms and/or area(s) in a building and/or home.

The problem with the current art, and without being limited, is that airborne agent(s) such as, but not limited to any, aerosol(s), gas(s), and/or vapor(s), cannot be moved and/or flowed and/or easily moved and/or flowed, through various air distribution and/or HVAC related part(s), such as, but not limited to any, air duct(s), air duct system(s), air supply duct(s), air supply trunk line(s), air return trunk line(s), vent component(s), air outlets, air inlets, air return duct(s), air shaft(s), hose(s) (40)(4380), blower(s), fan(s), valve(s), means to channel, stop, restrict, and/or direct air, and/or any other conduit(s) to move any air and/or gas(s) through, to, and/or from, one or more of any room(s) (4410), area(s), and/or building(s), HVAC part(s) and component(s) used to heat, cool, filter, and/or move air/gas(s) throughout a home or building, and more specifically through the connected and/or interconnected air duct system of an entire building or even one or more of any isolated area(s) of a building, because the various air supply duct(s) and their associated air supply vent(s), will supply airflow into one or more various room(s) and/or area(s), and the return and/or exit air vent(s) will allow air from these same room(s) and/or area(s) to exit the said room(s), and preferably and without limitation return it back to the said various HVAC equipment, thus posing problems known to those skilled in the art, such as, but not limited to, the said room(s) and/or area(s) will fill with the deployed and airborne agent(s), and any return or exit air ducts may not be exposed to an effective quantity and/or concentration of the deployed and airborne agent(s) for any effective treatment. Without being limited, the said deployed and airborne agent(s) can be used for purposes such as, but not limited to any, cleaning, sanitization, disinfection, sterilization, and/or decontamination, of the interior and/or exterior of the said various, air distribution duct(s), air duct(s) and/or HVAC related part(s) and component(s).

More specifically, and without limitation, the problem with the current art, and without being limited, is that airborne agent(s) such as, but not limited to any, aerosol(s), gas(s), and/or vapor(s), when deployed into any air supply ducts, will eventually flow into the various room(s) and/or area(s) in any building or home, through the various air supply vents located in these various room(s) and/or area(s). In many situations, and without being limited, this is not desired for various reasons known to those skilled in the art. In addition, and without limitation, it would be time consuming and larger amounts of airborne agent(s) would need to be used to fill these various rooms and/or area(s) with an effective amount and/or concentration of the said airborne agent(s) so that the airborne agent(s) can effectively flow from these room and/or area(s) and effectively treat the various air exit and/or air return vent(s) located in these various room(s) and/or area(s) as well as the various directly and/or indirectly connected air return and/or air exit duct(s) in the air duct system(s). Without being limited, the air supply duct(s) and air supply vent(s) can be any duct(s) and vent(s) that can supply air flow and/or deployed and airborne agent(s) to any room(s) and/or area(s), and the exit and/or return vent(s) and any connected air duct(s) can be any vent(s) and duct(s) that can allow airflow and/or deployed and airborne agent(s) to leave any room(s) and/or area(s).

Without being limited, by using the vent bypass system in the various room(s) and/or area(s) the one or more supply air duct(s) can be effectively connected to and communicate with the one or more return air duct(s), and more specifically the various room air supply vent(s) that connect with the various supply air duct(s) are effectively sealed and effectively connected via one or more of any suitable hose(s) and/or conduit(s) to the various room air return and/or exit vent(s) that connect with the various air return and/or air exit duct(s), thus allowing the air and the deployed agent(s) in the various air duct(s) and/or air duct system, to bypass the one or more room(s) and instead flow through the various conduit(s) and air ducts, and also preferably and without limitation, the various HVAC equipment and parts, that are all, preferably and without limitation, effectively connected together. The deployed agent provides at least one of sanitizing, disinfecting, high level disinfecting and sterilization. The present invention also describes, and without limitation, an enhanced vent bypass system that includes any suitable and effective means including, but not limited to any means to, filter air/gas(s), dehumidify air/gas(s), subject air/gas(s) to UV light, move, flow, blow and/or pump air/gas(s) and/or deployed agent(s), as well as any suitable and effective means to deploy, disperse, and/or administer any deployed agent(s), that can be and/or are moved and/or flowed through various, area(s), space(s), air/gas(s) duct(s), air/gas(s) shaft(s), HVAC system(s), HVAC part(s) and equipment(s), including the one or more enhanced vent bypass system(s).

Another problem with the current art is that many, aerosol generator(s), gas generator(s), and/or vapor generator(s), product(s) lack the ability or means to effectively treat large volume(s), remote location(s), and/or conduit(s) and/or air duct(s) with complex geometry(s), horizontal runs, and/or vertical runs, of various design complexities and/or long lengths, all in a manner known to those skilled in the art.

The present invention addresses these shortcomings, by directing, piping, and/or channeling, preferably and without limitation, in any suitable and effectively sealed manner, the generated vapor(s), gas(s), and/or aerosol(s), into at least one aerosol(s), gas(s), and/or vapor(s) collection chamber(s) and/or agent flow compartment(s), which is connected to and communicates with at least one effective, blower(s), fan(s), and/or air pump(s), and where the said collection chamber(s) and/or agent flow compartment(s) can directly and/or indirectly removably communicate and/or effectively connect with various, enclosure(s), chamber(s), room(s), space(s), conduit(s), HVAC equipment, vent bypass system(s), air shaft(s), and/or air duct(s), to effectively flow the generated aerosol(s), gas(s), and/or vapor(s), into these various space(s), location(s), and/or area(s) to coat and/or treat their various surfaces. The said generated vapor(s), gas(s), and/or aerosol(s), are blown, pumped, and/or flowed, into the said collection chamber(s) and/or agent flow compartment(s) with or using one or more of any suitable and effective source(s) of air and/or gas(s) flow(s) such as, but not limited to any, one or more effective source(s) of air and/or gas(s) that also supplies air and/or gas(s) to the said collection chamber(s) and/or agent flow compartment(s) in addition to the one or more means for producing and/or generating the said generated vapor(s), gas(s), and/or aerosol(s), and/or one or more effective source(s) of air and/or gas(s) that is separate from any air and/or gas(s) supply to the said collection chamber(s) and/or agent flow compartment(s) and independently supplies air and/or gas(s) to the one or more of any suitable and effective means for producing and/or generating the said generated vapor(s), gas(s), and/or aerosol(s).

Still another problem with the current art, and without limitation, is that various apparatus(s), agent generator(s), and/or agent dispenser(s), that generate, administer, distribute, flow, deliver, disperse, and/or transmit, one or more of, and/or one or more of any combination of any, substance(s), agent(s), chemical(s), chemistry(s), and/or molecule(s), and in one or more of any suitable and effective form(s), such as, but not limited to any, gas(s), plasma(s), vapor(s), aerosol(s), dry aerosol(s), liquid aerosol(s), and/or deployed agent(s), to one or more of any area(s), surface(s), and/or space(s), for one or more of any purpose(s) such as but limited to, the cleaning, sanitization, disinfection, sterilization, and/or decontamination, of one or more and/or various, surface(s), space(s), and/or area(s), can be limited for various reason(s) known to those skilled in the art, including, but not limited to, the deployed, gas(s), vapor(s), aerosol(s), dry aerosol(s), liquid aerosol(s), and/or deployed agent(s), may not have any effective velocity(s), speed(s), rate(s) of travel, area(s) filling speed(s), and/or effective volume(s) of deployed agent(s) to effectively reach, fill, and/or treat, the one or more targeted area(s) and/or surface(s). Without being limited, this can be especially true when treating various HVAC systems and their air ducts, as well as very large connected and/or non-connected area(s) and space(s), as known to those skilled in the art.

Without being limited, the present invention addresses these various problem(s) with the current art, by effectively connecting, communicating, and/or removably communicating, one or more of any suitable and effective means known to those skilled in the art for generating, creating, dispensing, deploying, and/or storing, the said gas(s), plasma(s), vapor(s), aerosol(s), dry aerosol(s), liquid aerosol(s), and/or deployed agent(s), (and/or otherwise the deployed agent(s) generator(s)), with one or more of any suitable and effective compartment(s) and/or enclosure(s), (and/or otherwise the agent flow compartment(s)) that has any suitable and effective size(s), geometry(s), design(s), and shape(s), and where both the deployed agent(s) generator(s) and the agent flow compartment(s) are supplied with one or more suitable and effective source(s) of air/gas(s) flow(s) and/or pressurized air/gas(s) flow(s), using one or more of any suitable and effective means for moving air/gas(s) known to those skilled in the art. It is preferred, without limitation, that at least one suitable and effective, fan(s), air pump(s), and/or blower(s) moves an effective quantity of air/gas(s) into the deployed agent(s) generator(s) and the agent flow compartment(s). It is more preferred, without limitation, that at least one suitable and effective, fan(s), air pump(s), and/or blower(s), moves an effective quantity of air/gas(s) into the deployed agent(s) generator(s), and at least another one and separate suitable and effective, fan(s), air pump(s), and/or blower(s), also moves an effective quantity of air/gas(s) into the agent flow compartment(s).

Without being limited, one or more of any flow(s) and/or movement(s) of any, air/gas(s) and/or pressurized air/gas(s), is effectively moved, flowed, and/or delivered to and/or into, the said deployed agent generator(s), preferably and without limitation from one or more of any suitable and effective location(s) outside of the deployed agent(s) generator(s), which is used to flow and/or move the said, gas(s), plasma(s), vapor(s), aerosol(s), dry aerosol(s), liquid aerosol (s), and/or deployed agent(s), from the deployed agent(s) generator(s) and into the said agent flow compartment(s). Also, and without being limited, one or more of any flow(s) and/or movement(s) of any, air/gas(s) and/or pressurized air/gas(s), is also effectively moved, flowed, and/or delivered to and/or into, the said agent flow compartment(s), preferably and without limitation from one or more of any suitable and effective location(s) outside of the agent flow compartment(s), which is used to flow and/or move the said, gas(s), plasma(s), vapor(s), aerosol(s), dry aerosol(s), liquid aerosol(s), and/or deployed agent(s), out of the agent flow compartment(s) and into the one or more targeted area(s) and/or space(s).

BRIEF DESCRIPTION OF THE DRAWINGS

FIG. 1 is an exploded perspective view of a portable automated vent cover.

FIG. 2 is an electrical schematic of a portable automated vent cover.

FIG. 3 is an enlarged perspective view of a drive system of a portable automated vent cover with a down stop in a raised position.

FIG. 4 is an enlarged perspective view of a drive system of a portable automated vent cover with a down stop in a lowered position.

FIG. 5 is an enlarged perspective view of a mobile tripod of a portable automated vent cover.

FIG. 6 is an enlarged perspective view of a mobile tripod of a portable automated vent cover in a collapsed orientation.

FIG. 7 is a bottom perspective view of a vacuum release door in contact with a vent cover door of a vent cover system in accordance with the present invention.

FIG. 8 is a bottom perspective view of a vacuum release door fully withdrawn from a vent cover door of a vent cover system in accordance with the present invention.

FIG. 9 is a top perspective view of a vacuum release door in contact with a vent cover door of a vent cover system in accordance with the present invention.

FIG. 10 is a side partially cross sectional view of a first vent cover system adjacent to a second vent cover system connected to each other with a vent bypass system in accordance with the present invention.

FIG. 11 is a side view of a treated room or space with at least one gas entry vent and at least one gas exit vent of a vent bypass system in accordance with the present invention.

FIG. 12 is a side view of targeted space having an gas entry vent and a gas exit vent, both sealed with a separate vent cover door and a vacuum release door, all in a sealed state, and positioned against a ceiling surface with a manual vent holding apparatus, where both vents are connected via a hose connecting both vent cover doors and their respective vents of a vent bypass system in accordance with the present invention.

FIG. 13 is a side view of targeted space having an air/gas entry vent and an gas exit vent, both sealed with a separate vent cover door and a vacuum release door, all in a sealed state, and positioned against a ceiling surface with a portable automated vent cover apparatus, where both vents are connected via a hose connecting both vent cover doors and their respective vents of a vent bypass system in accordance with the present invention.

FIG. 14 a side view showing air/gas flowing into a room or connected space from two separate entry vents, and then exiting the room from one exit vent of a vent bypass system in accordance with the present invention.

FIG. 15 a side view showing air/gas flowing into a room or connected space from one entry vent, and then exiting the room from three separate exit vents of a vent bypass system in accordance with the present invention.

FIG. 16 is a schematic diagram of a two story building showing at least one room and the rooms communicate with at least one system of shared air ducts that communicate with at least one HVAC system that supply air to the at least one room on each floor in accordance with the present invention.

FIG. 17 is a schematic diagram of a two story of building showing at least one room on each floor and the rooms are connected by at least one system of shared air ducts that communicate with at least one HVAC system that supply air to the at least one room on each floor with a duct fan located in a hose, which connects flow between entry and exit vents on a second floor.

FIG. 18 is a schematic diagram of two story building showing at least one room on each floor and the rooms communicate with at least one system of shared air ducts that are effectively sealed on one end, and communicate with at least one air entry filter on the sealed end.

FIG. 19 is a schematic side view of a two story building showing at least one room on each floor, where the at least one room communicates with at least one system of shared air ducts to supply air into the at least one room and to provide a means for air to exit the at least one room, and at least one of the at least one room is isolated from communicating with the another room.

FIG. 20 is a schematic side view of a two story building showing at least one room on each floor, where the at least one room communicates with at least one system of shared air ducts to supply air into the at least one room to provide a way for air to exit the at least one room, and at least one of the at least one room is isolated from communicating with another room by effectively sealing various effective ends of various air ducts that provide air into and out of the at least one isolated room.

FIG. 21 is a schematic diagram of isolated and sealed off air ducts that communicate with at least one HVAC unit that contains one or more of any apparatus(s) used for purposes such as, but not limited to any filtering, heating, humidification, dehumidification, movement, ventilation, and/or cooling, of any air and/or air flow(s) that pass through the HVAC unit.

FIG. 22 is a schematic diagram of an enhanced deployed agent generator that includes at least one aerosol, gas, and/or vapor collection chamber which is connected to and communicates with at least one blower, fan, and/or air pump.

FIG. 23 is a schematic diagram of an enhanced vent bypass system used in a multi-story building, where hoses and/or conduits that connect to one part of the vent bypass system that covers and seals the air/gas(s) vent(s) in an area(s) and/or room(s) is first connected to and communicates with one or more of any, air filter(s), blower(s), heater(s), and/or agent dispenser(s), and is then connected and sealed to the other means to cover and seal the other air/gas(s) vent(s) in the room(s)/area(s).

FIG. 24 is a schematic diagram of an enhanced deployed agent(s) generator that includes at least one aerosol, gas, and/or vapor collection chamber which is connected to and communicates with at least one blower, fan, and/or air pump, and where the collection chamber can directly and/or indirectly removably communicate with various conduit(s), HVAC equipment, air shaft, and/or air duct to flow the generated aerosol, gas, and/or vapor into enclosure(s), space(s), location(s), and/or area(s).

FIG. 25 is a schematic side view of an enhanced deployed agent(s) generator that includes at least one aerosol(s), gas(s), and/or vapor(s), collection chamber(s) or agent flow compartment(s), which is connected to and communicates with at least one blower(s), fan(s), and/or air pump(s) that is effectively connected to and communicates with and receives air/gas(s) from one or more of any, conduit(s), HVAC equipment, air shaft(s), air duct(s), space(s), chamber(s), enclosure(s), and/or room(s).

FIG. 26 is a schematic side view of an enhanced deployed agent(s) generator, which is connected to and communicates with at least one of blower(s), fan(s), and/or air pump(s) that is effectively connected to and communicates with and receives air/gas(s) from one or more of any, conduit(s), HVAC equipment, air shaft(s), air duct(s), space(s), chamber(s), enclosure(s), and/or room(s), and where the said agent flow compartment(s) can also directly and/or indirectly removably communicate with one or more of any of the said, conduit(s), HVAC equipment, air shaft(s), air duct(s), space(s), chamber(s), enclosure(s), and/or room(s).

DETAILED DESCRIPTION OF THE PREFERRED EMBODIMENTS

Figure 6:
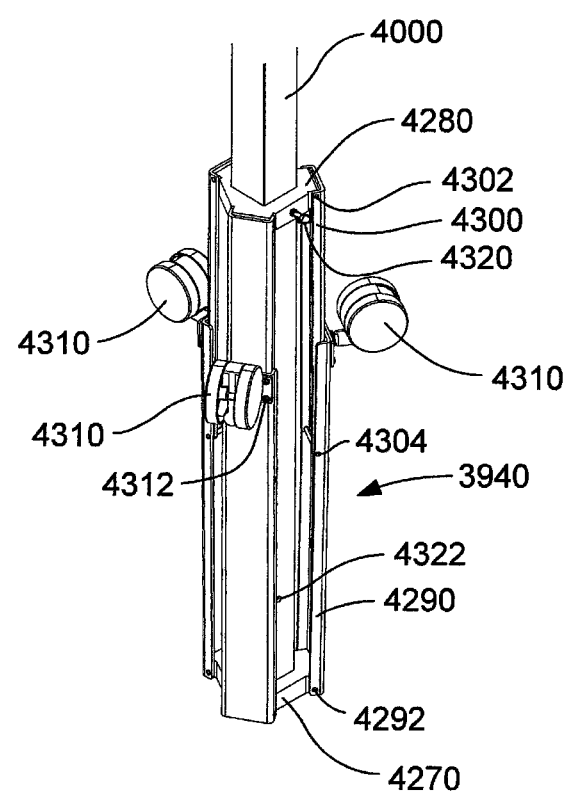
Figure 7:
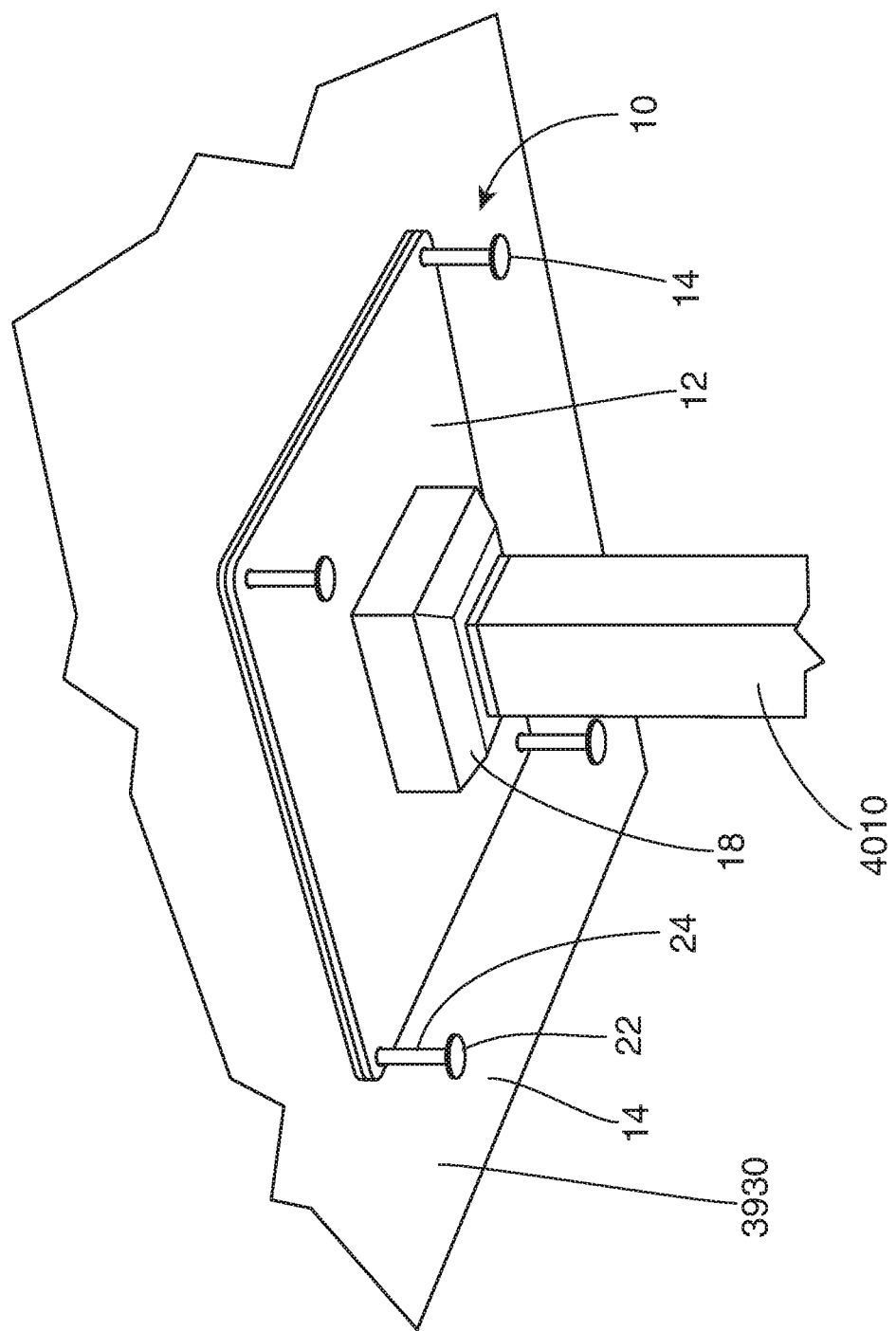
Figure 10:
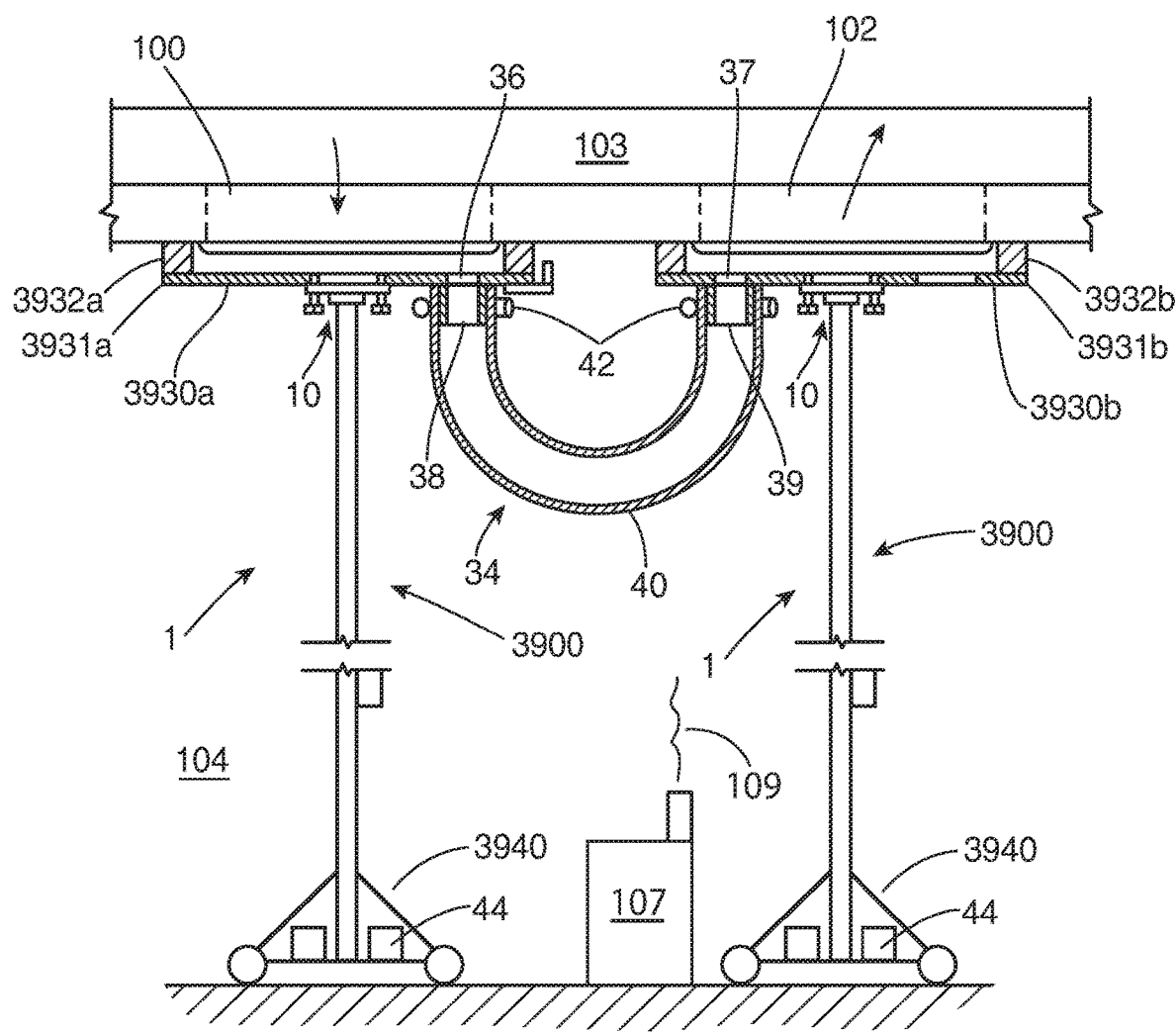
Figure 11:
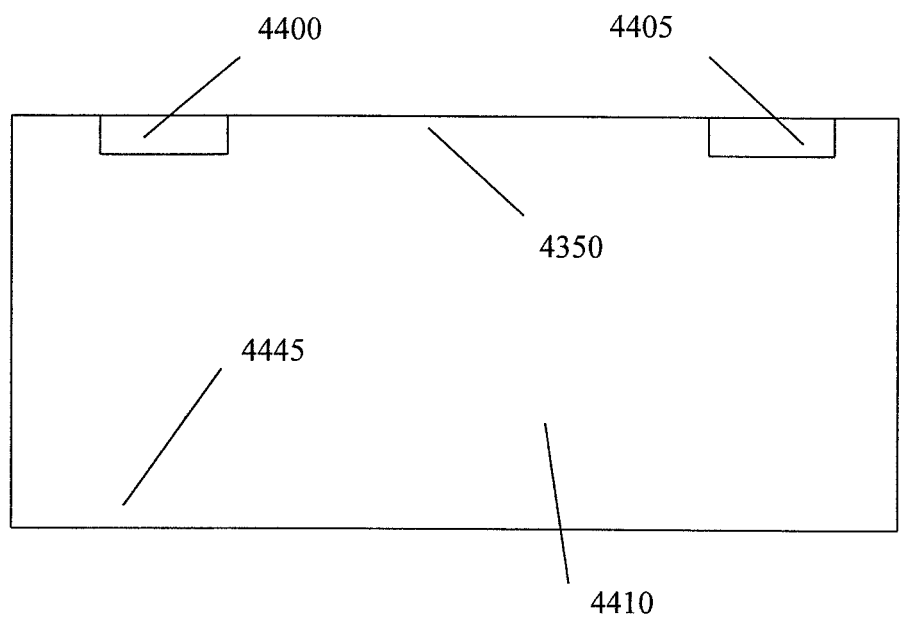

With reference now to the drawings, and particularly to FIG. 7, there is shown a perspective view of a vacuum release door (10) in contact with a bottom of a vent cover door (3930) of a portable automated vent cover 3900. With reference to FIG. 10), a vent cover system (1) preferably includes the portable automated vent cover (3900) and the vacuum release door (10). With reference to FIGS. 1-6, the portable automated vent cover (3900) preferably includes a drive system (3910), a telescoping tube (3920), a vent cover door (3930) and a collapsible mobile tripod (3940). The drive system (3910) preferably includes a drive motor (3950), a gear box (3960), a drive housing (3970), an up-relay (3980) and a down-relay (3990). The up and down relays are preferably double pole/double throw relays. However, the drive system (3910) could be replaced with any suitable manual lift system (not shown). The manual lift system may be locked to any appropriate height. The telescoping tube (3920) includes an outer support tube (4000), an inner cover tube (4010), a rack gear (4020) and a stop collar (4030). However, other types of extendable supports besides telescoping tube (3920) may also be used. The drive motor (3950) drives an input of the gear box (3960) and an output shaft (4040) is driven by an output of the gear box (3960). A pinion gear (4050) is retained on the output shaft (4040) and the rack gear (4020) is driven by through the pinion gear (4050). The gear box (3960) reduces the speed of the drive motor (3950). Small electric motor gear boxes are well known in the art and need not be explained in detail. The drive motor (3950) is preferably a DC motor, but other motors could also be used.

The drive housing (3970) includes a first housing half (4060) and a second housing half (4070). Each end of the output shaft (4040) is rotatably supported by the first and second housing halves. The first housing half (4060) includes a first tube slot (4080) and the second housing half (4070) includes a second tube slot (4090). The first and second tube slots are sized to receive an outer perimeter of the outer support tube (4000). The first and second housing halves are secured to the inner cover tube (4010) with a plurality of fasteners (4100). A drive system cover (4110) is attached to an outside perimeter of the first housing half (4060) with a plurality of fasteners (4120). The up and down relays are retained in the drive system cover (4110). An inlet hole (4130) is formed through a wall of the drive system cover (4110) to receive an inlet electrical connector (4140). The inlet electrical connector (4140) is attached to the drive system cover (4110) with at least two fasteners (4150). The inlet electrical connector (4140) is connected to the electronic controller or programmable logic circuit (315) with an electrical cable (not shown).

The inlet electrical connector (4140) includes a ground line (4142), a power supply line (4144) and a retract power line 4146. A switch opening (4170) is formed through a wall of the drive system cover (4110) to receive an up-down switch (4160). The up-down switch (4160) is an on-off-on switch. The up-down switch (4160) includes an off-pole (4162), a first on-pole (4164) and a second on-pole (4166). The off-pole (4162) of the up-down switch (4160) is connected to the power supply line (4144) of the inlet electrical connector (4140). A switch lever (4168) of the up-down switch (4160) is toggled to the first on-pole (4164) to raise the inner cover tube (4010).

The electrical power flowing through the first on-pole (4164) energizes the up-relay (3980), which sends electrical power to the drive motor (3950) through a first contact (3982) and provides a path to ground for the drive motor (3950) through a second contact (3984). The electrical power flowing through the first on-pole (4164) is connected in series with a reset fuse (4172), which prevents the motor (3950) from being damaged, when the vent cover door (3930) is forced against the vent opening (4355). The motor (3950) is preferably a permanent magnet DC motor.

Electromagnetic braking is inherent in permanent magnet DC motors. The electromagnetic braking keeps the vent cover door (3930) in contact with the vent opening (4355). The switch lever (4168) is toggled to the second on-pole (4166) to lower inner cover tube (4010). The electrical power flowing through the second on-pole (4166) energizes the down-relay (3990), which sends electrical power to the drive motor (3950) through a first contact (3992) and provides a path to ground for the drive motor (3950) through a second contact (3994). The retract power line (4146) is connected to the second on-pole (4166). Electrical power supplied through the retract power line (4146) will also lower the inner cover tube (4010).

The vent cover door (3930) includes a cover plate (4180), a peripheral sealing ring (4190) and a tube flange (4200). The peripheral sealing ring (4190) is attached to a top of the cover plate (4180) and around a perimeter thereof. The peripheral sealing ring (4190) is preferably fabricated of rubber, a rubber like material or any other suitable material. The tube flange (4200) is attached to a bottom of the cover plate (4180). The tube flange (4200) includes a tube opening (4210), which is sized to receive the inner cover tube (4010.) A tightening screw (4212) is used to secure the inner cover tube (4010) in the tube flange (4200). The rack gear (4020) is attached to the inner cover tube (4010) with a plurality of fasteners (4220). An end cap (4012) is preferably retained in a bottom of the inner cover tube (4010) with at least one fastener (4014). A rack slot (4230) is formed in the outer support tube (4000) to provide clearance for the rack gear (4020). The stop collar (4030) includes a clamp slot (4032), a tube opening (4034) and a stud slot (4036). A threaded stud (4240) is secured in the stud slot (4036) with a pair of nuts (not shown) secured to a top and bottom of the stop collar (4030). The threaded stud (4240) is positioned to actuate a normally closed limit switch (4250) to an open position to stop the flow of electricity to the down-relay (3990). The threaded stud (4240) is axially and radially adjusted to actuate a lever (4252) of the limit switch (4250) and stop the flow of electricity to the drive motor (3950), just before the down stop strikes a top of the drive housing (3970). A clamping fastener (4260) is tightened to secure the stop collar (4030) on the inner cover tube (4010).

Figure 1:
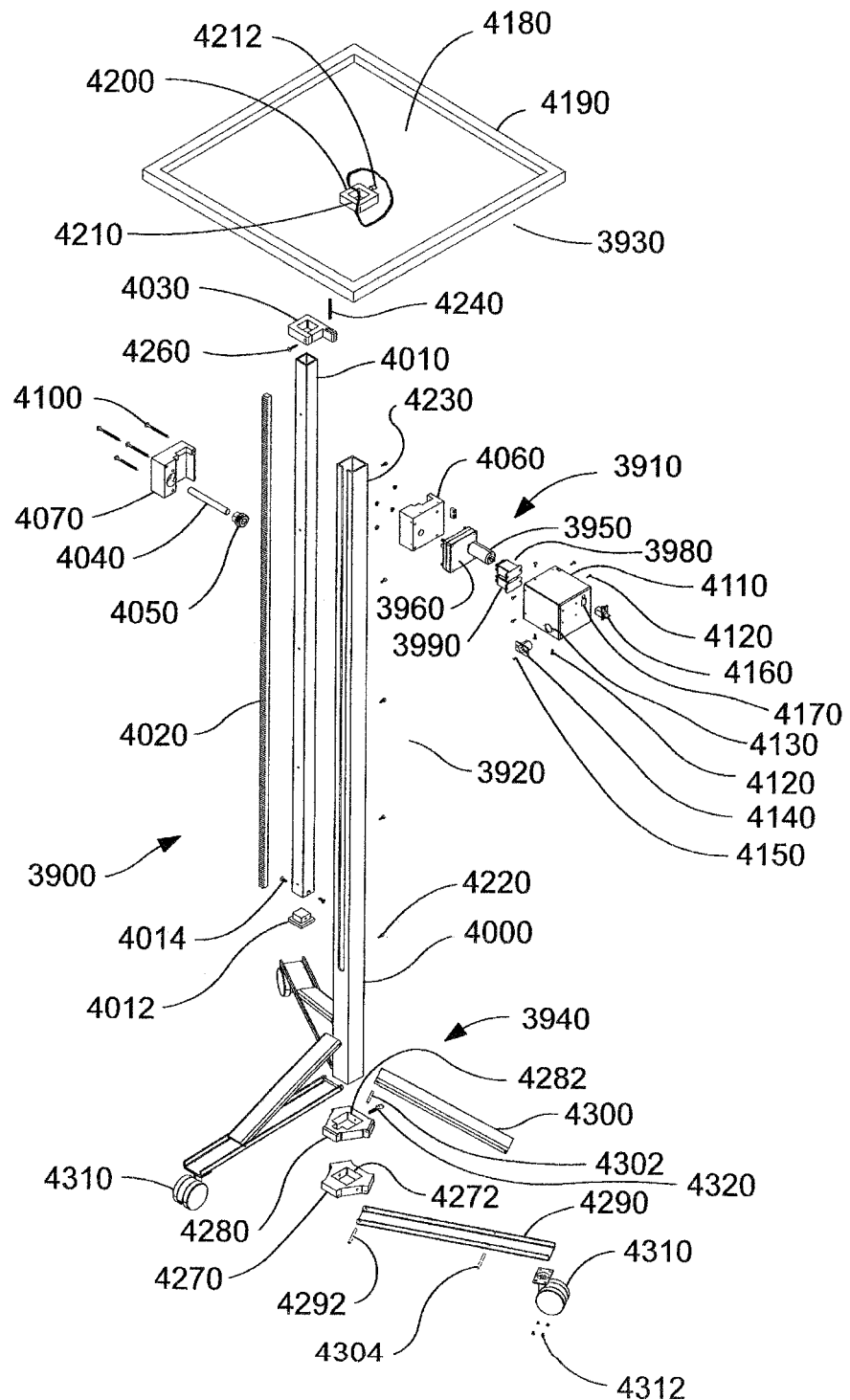
Figure 2:
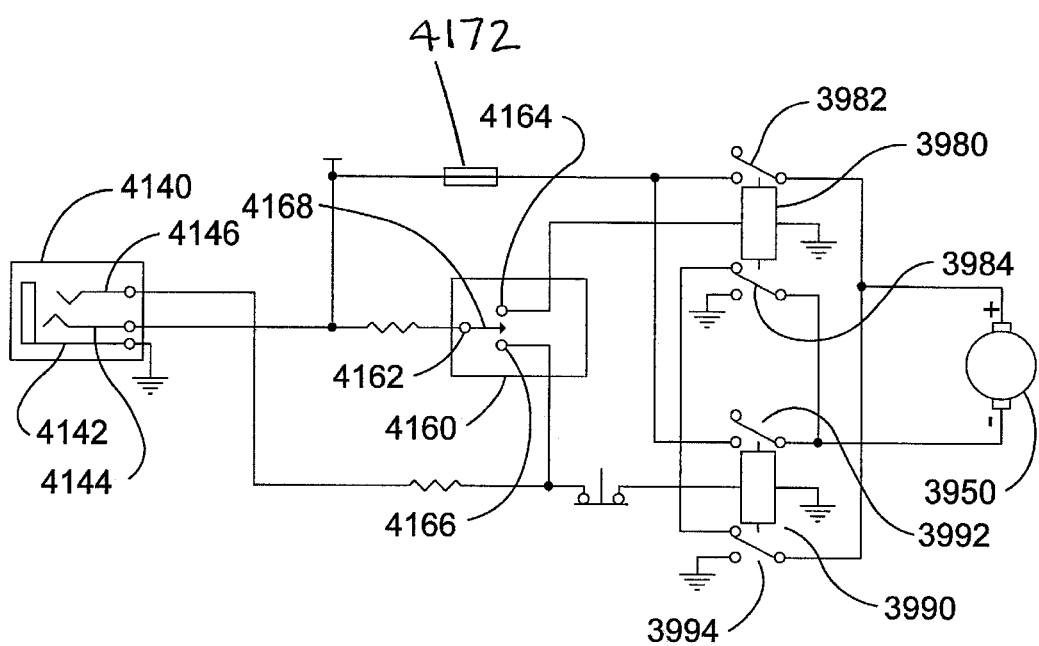
Figure 3:
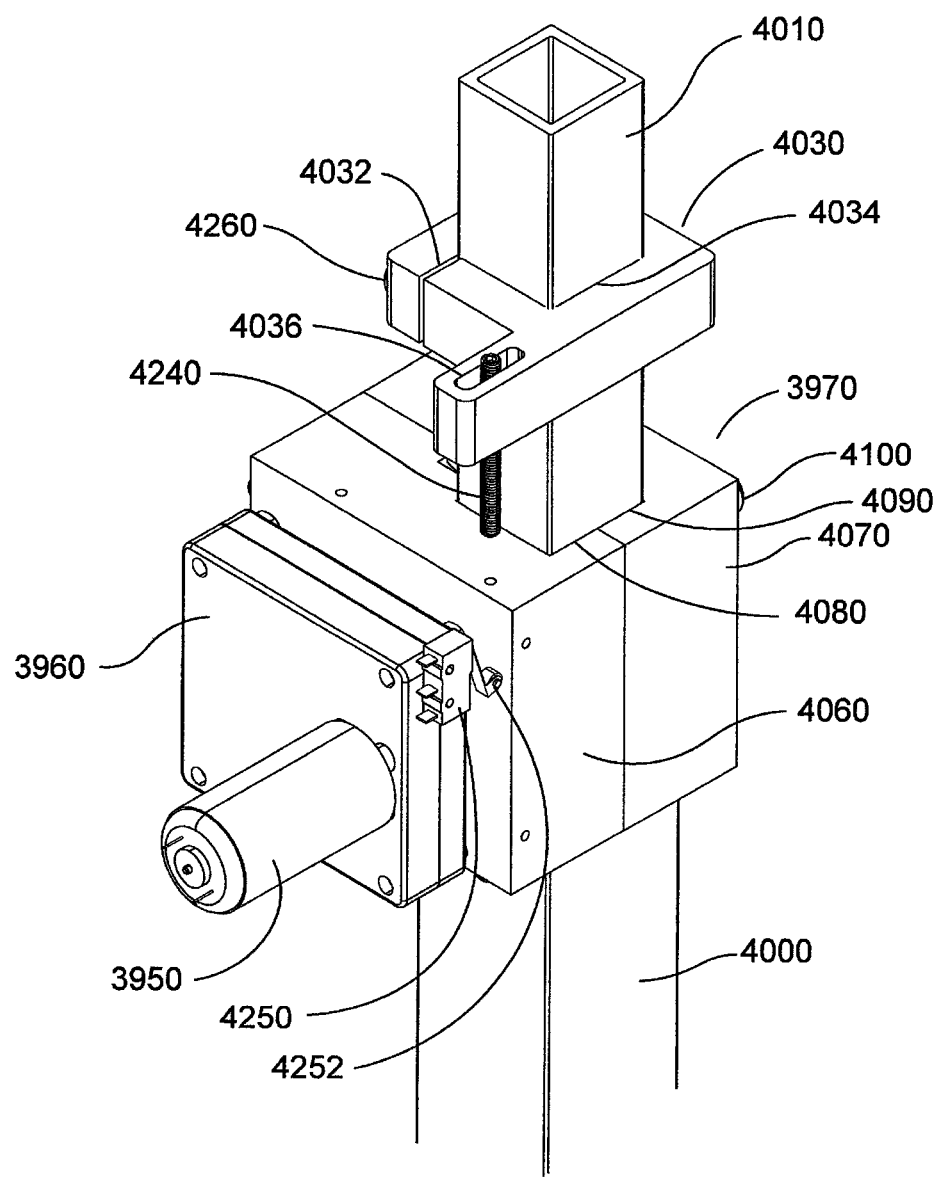
Figure 4:
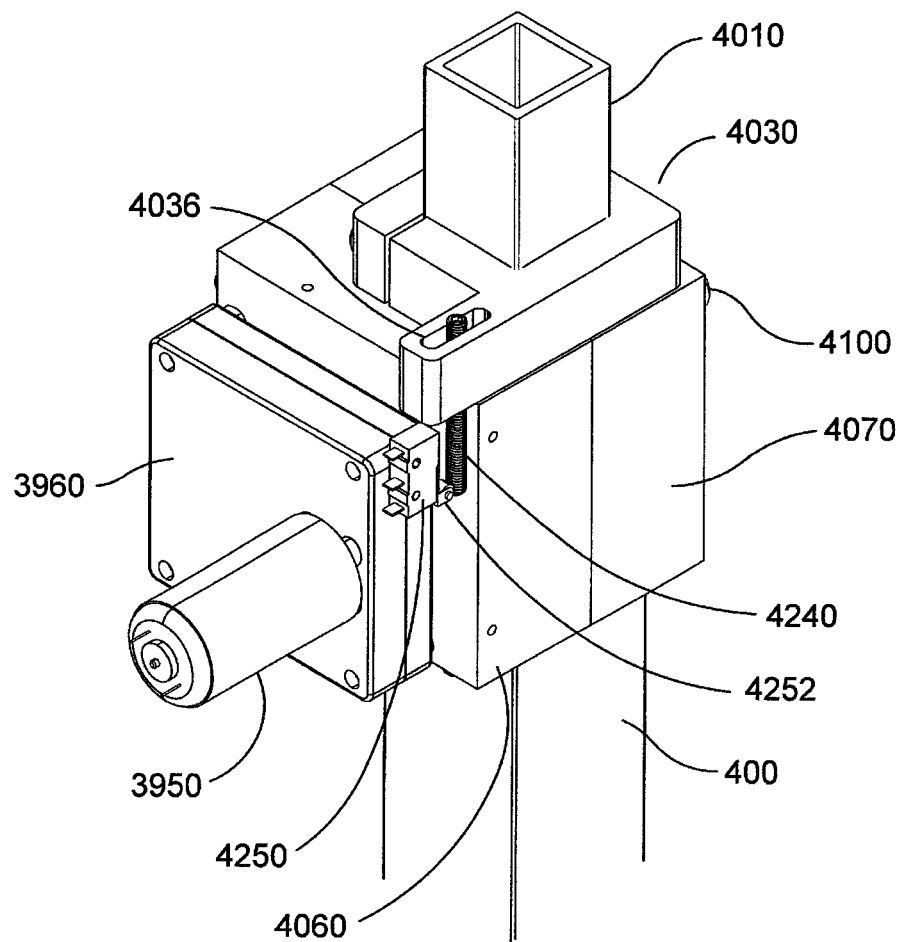
Figure 5:
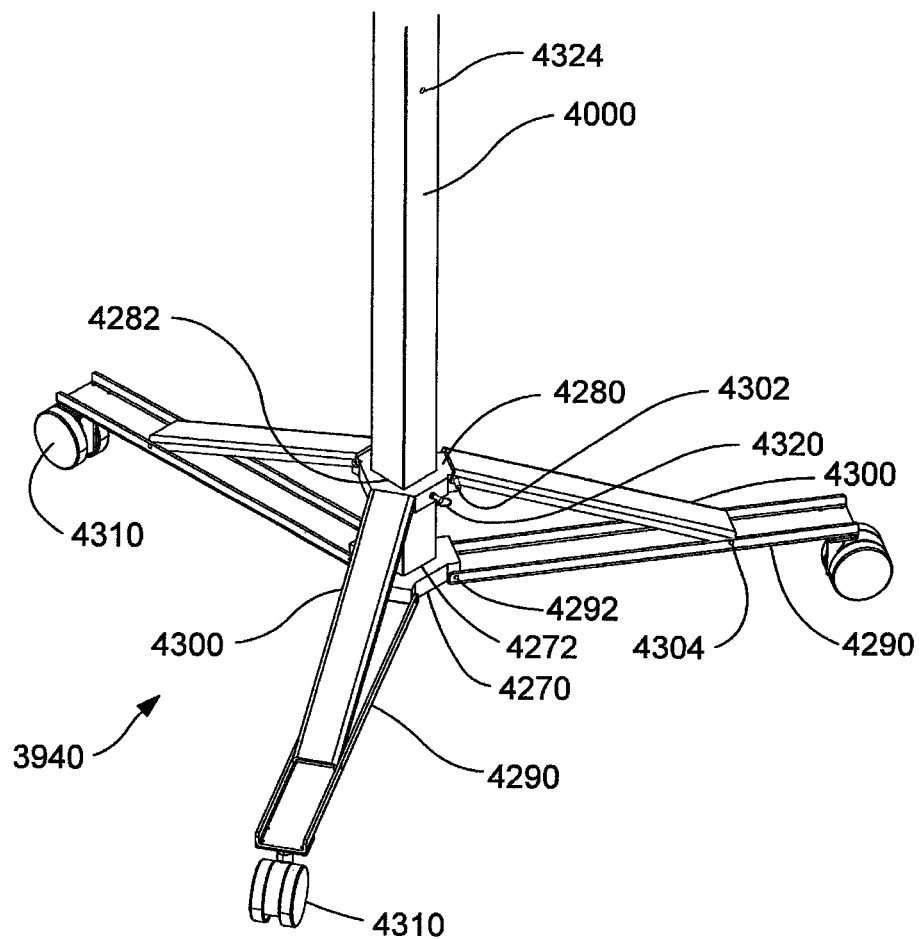

With reference to FIGS. 5-6, the collapsible mobile tripod (3940) preferably includes a stationary pivot block (4270), a sliding pivot block (4280), three lower support arms (4290), three upper support arms (4300) and three castors (4310). The stationary pivot block (4270) includes a tube opening (4272), which is sized to receive the outer support tube (4000). The stationary pivot block (4270) is attached to a bottom of the outer support tube (4000) with any suitable device or method, such as fasteners. One end of the three lower support arms (4290) are pivotally attached equidistant around a perimeter of the stationary pivot block (4270) with three pivot pins (4292). The three castors (4310) are attached to a bottom of the other end of the three lower support arms (4290) with a plurality of fasteners (4312). The sliding pivot block (4280) includes a tube opening (4282), which is sized to slidably receive the outer support tube (4000).

One end of the three upper support arms (4300) are pivotally attached equidistant around a perimeter of the sliding block (4280) with three pivot pins (4302). The other end of the three upper support arms (4300) are pivotally attached to the three lower support arms with three pivot pins (4304). A locking pin (4320) is inserted through the sliding support block (4280) and a support hole (4322) or a retraction hole (4324) in the outer support tube (4000) to place the mobile tripod in a support orientation or a retracted orientation, respectively.

Figure 8:
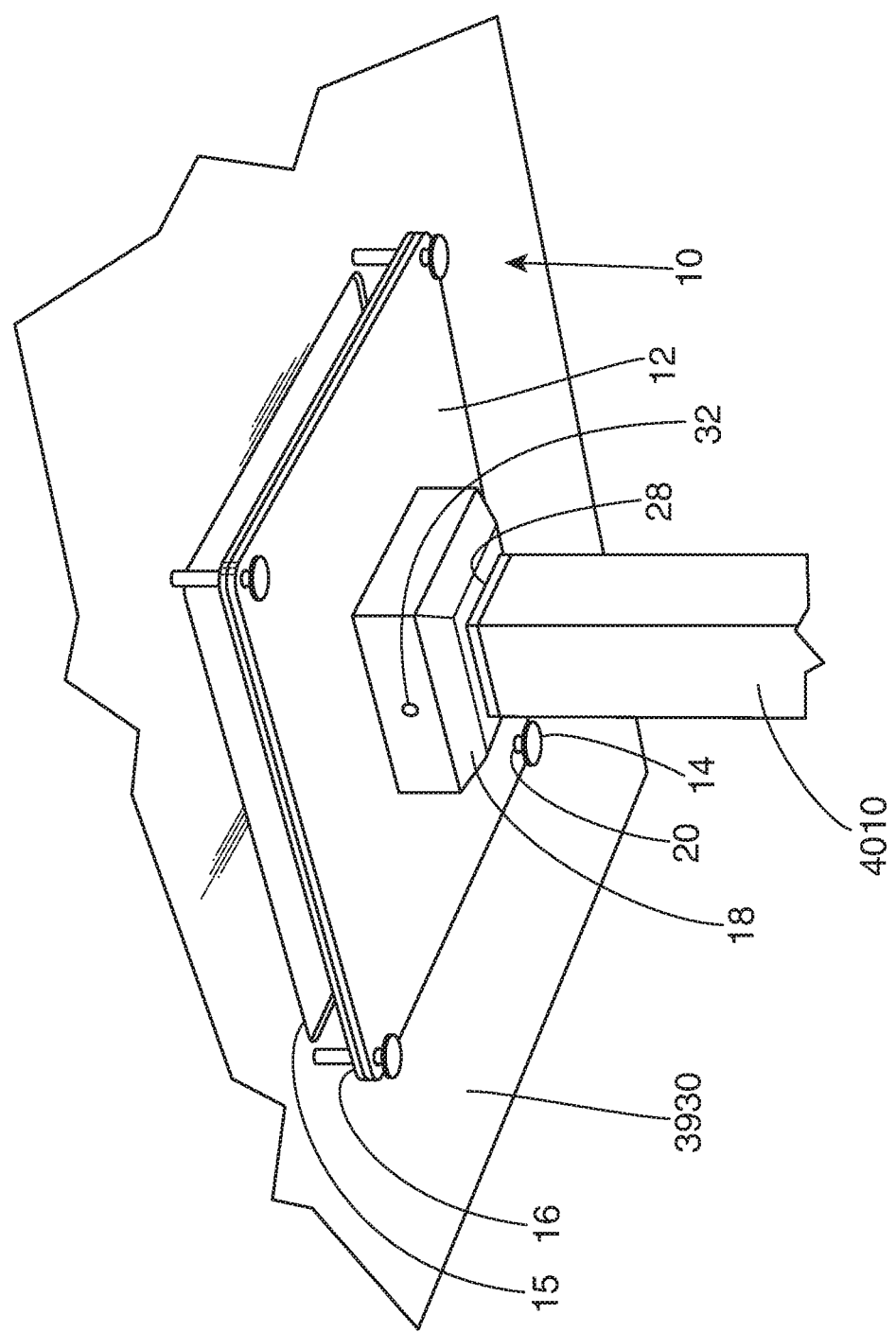
Figure 9:
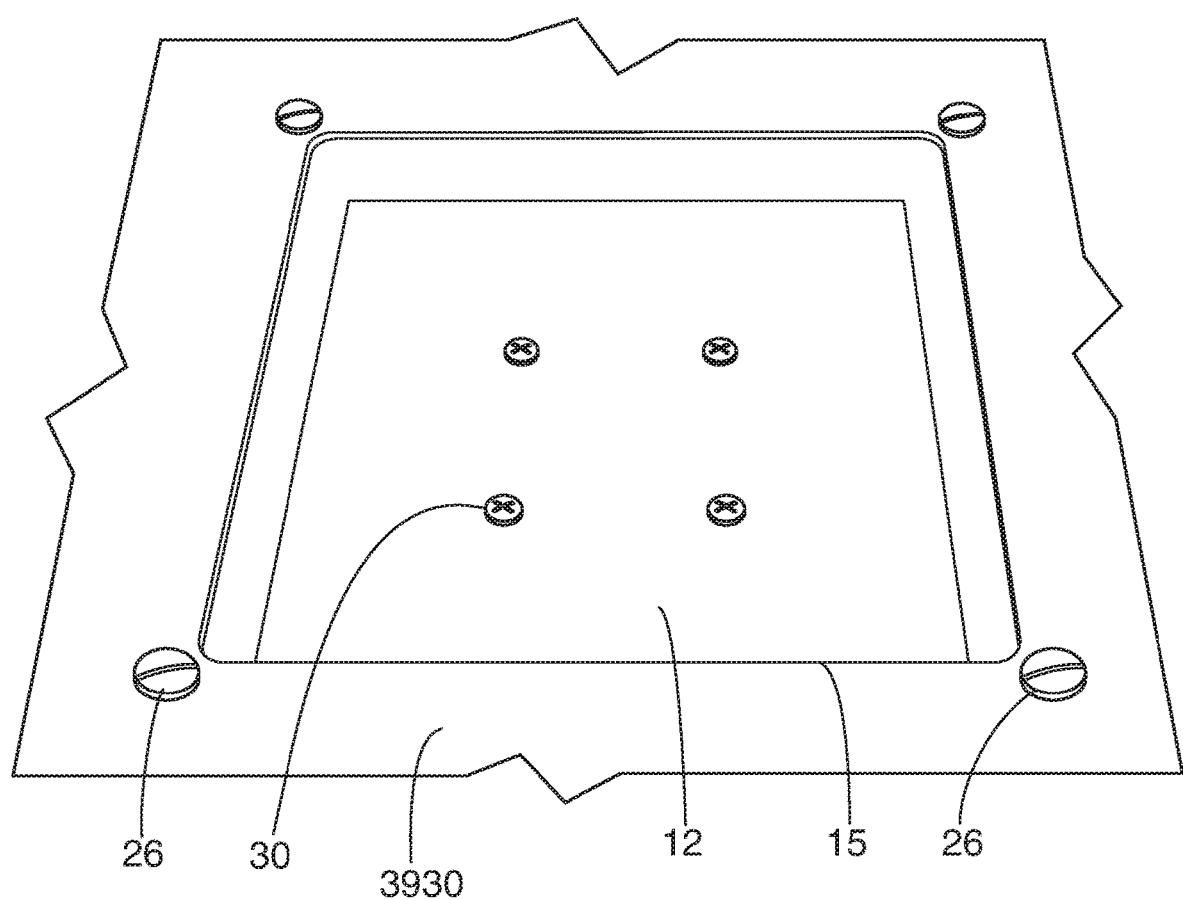

With reference to FIGS. 7-9, the vacuum release door (10) preferably includes a vacuum door plate (12), a plurality of retention pins (14), a sealing gasket (16) and a tube flange (18). The sealing gasket (16) preferably includes the same outer perimeter as the vacuum door plate (12). The sealing gasket (16) is preferably fabricated from rubber, a rubber like material, or any suitable material. A vacuum break opening (15) is formed through a center of the vent cover door (3930). The vacuum door plate (12) has an outer perimeter that is larger than a perimeter of the vacuum break opening (15). The sealing gasket (16) is attached to a top of the vacuum door plate (12). A plurality of pin holes (20) are formed around a perimeter of the vacuum door plate (12) to slidably receive the plurality of retention pins (14). Each retention pin (14) includes a head portion (22) and a pin portion (24). The pin portion (24) extends from the head portion (22). The pin portion (24) is inserted through the plurality of pin holes (20) and attached to the vent cover door (3930) with fasteners (26) or the like. Alternatively, and without limitation, the pin portion (24) is inserted through the plurality of pin holes (20) and attached to the vent cover door (3930) and/or the cover plate (4180), with fasteners (26) or the like. The pins (24) may also be suitably terminated on both ends, so they can perform their intended purposes, while also being able to have axial movement in the pin holes (20). However, other devices may also be substituted for the plurality of retention pins (14), such as but not limited to any type of guide rails. The tube flange (18) includes a tube opening (28), which is sized to snugly receive a top end of the inner cover tube (4010). The tube flange (18) is attached to a bottom of the vacuum door plate with fasteners (30) or the like. The inner cover tube (4010) is retained in the tube flange (18) with a pin (32) or the like.

In use, the vent cover door (3930) is raised, until a peripheral sealing ring (4190) on a top of the vent cover door (3930) seals around and/or to a perimeter of a vent opening (not shown). When an attempt is made to lower the vent cover door (3930) from the vent opening, retraction of the inner cover tube (4010) will cause a seal to be broken between the vacuum door plate (12) and the vacuum break opening (15) in the vent cover door (3930). After the seal is broken, the plurality of retention pins (14) will experience a downward force, which will cause a seal between the vent cover door 3930 and the vent opening to be broken. The vent cover system (1) makes it easier to break a seal between the vent opening and the vent cover door (3930), because the perimeter of the vacuum release door (12) is much shorter than a perimeter of the vent cover door (3930).

An air gap between a bottom of the vent cover door (3930) and a top of the vacuum door plate 12 is preferably, and without limitation, at least ⅛ inch, when the vacuum door plate (12) is in an open position. The vacuum door plate (12) seals the vacuum break opening (15) in a closed orientation. The vacuum door plate (12) does not cover the vacuum break opening (15) in an open orientation. It is easier to break a small perimeter seal than a large perimeter seal.

With reference to FIG. 10, a vent bypass system (34) includes at least one first vent cover (3930a) and at least one second vent cover (3930b). The first vent cover (3930a) includes a first vent plate (3931a) and a first sealing ring (3932a). The second vent cover (3930b) includes a second vent plate (3931b) and a second sealing ring (3932b). The vent bypass system (34) is created by forming a first bypass hole (36) through the first vent plate (3931a), and a second bypass hole (37) through a second vent plate (3930b) of two adjacent vent cover systems (1). A first tube flange (38) extends from a bottom surface of the first vent cover (3930a), and a second tube flange (39) extends from a bottom surface of the second vent cover (3930b), concentric with the bypass hole (36). The first vent cover (3930a) covers an entry vent (100) and the second vent cover (3930b) covers an exit vent (102). A first end of a flexible tube (tubular member) (40) is secured to the tube flange (38) of the first vent cover (3930a) with a securement device, such as a hose clamp (42) or the like, and a second end of the flexible tube (40) is secured to the second tube flange (38) of the second vent cover (3930b). The flexible tube or 22 tubular member may have any suitable cross-sectional shape.

The tubular member (40) member will keep the HVAC system (103) substantially balanced by not sealing up a normal flow pattern through the enclosed space (104). Any type of support device may be used to force the first vent cover door (3930*a*) against the entry vent (100) and the second vent cover door (3930*b*) against the exit vent (102), such as a painter's pole (4365), a collapsible mobile tripod (3940), or any other suitable manual or automated support device.

Gas blown into the enclosed space (104) will bypass circulating through the enclosed space (104) by going through the flexible tube 40 from the entry vent (100) to the exit vent (102). The vent bypass system (34) will also keep a balance in a circulating system by not sealing up a normal flow pattern through the room. Additionally, more than one entry vent (100) may be transferred to one exit vent 102 with more than one tube (40), or one entry vent (100) may be transferred to more than one exit vent (102) with more than one tube (40).

With reference to FIGS. 11-15, an alternative embodiment of the vent bypass system (4415) can be positioned to and/or sealed against gas vents (4400) and (4405) in various ways including, but not limited to, automatically using any automated vent cover apparatus (3900), and/or manually using any manually adjustable vent cover holding and sealing apparatus (4430).

Without being limited, the vent bypass system (4415), can also include various components, such as, but not limited to any, vacuum release door(s) (10), vacuum break opening(s) (15), vent cover door(s) (3930), hose(s) (4380), and hose connection(s) (4420). The hose(s) (4380) can effectively connect and operate with any apparatus or component that can effectively seal any air/gas entry vent(s) (4400) and any air/gas exit vent(s) (4405). It is preferred, without limitation that the hose(s) (4380) connect to the various vent cover door(s) (3930) with one or more of any hose connection(s) (4420). Without being limited, the hose(s) (4380) can allow any air/gas to flow out from one or more vent(s) (4400) that opens into a room(a) or connected space(s), through the hose(s) (4380), and into and out of another one or more vent(s) (4405) that is in the same room or connected space, allowing the air/gas(s) to leave that room(s) or connected space(s). It is preferred, without limitation, that these one or more room(s) or connected space(s) (4410) are effectively connected and sealed.

More specifically, and without being limited, the hose connection(s) (4420) can include, one or more of any inbound air/gas hose connection(s) (4385) and outbound air/gas hose connection(s) (4390), all known to those skilled in the art, and they can be directly and/or indirectly connected, in various ways including, permanently, semi-permanently, and/or removable, to any vent covering component(s) such as, but not limited to any, vent cover door(s) (3930), or any other connected location(s) and/or component(s), all in a manner known in the art.

Referring again to FIGS. 14-15, and without being limited, any vent(s) connecting to any rooms and/or connected space(s), or any part of any vent(s) such as, but not limited to any, air/gas entry vent(s) (4400), air/gas exit vent(s) (4405), and/or any vent opening(s) (4355), can also be designed to be effectively sealed against the escape of any air/gas(s), while still being effectively sealed to and effectively interfaced with, any hose connection(s) (4420) for the passage of any air/gas(s) to any hose(s) (4380).

Again, with reference to FIGS. 11-15, the hose connection(s) (4420) can allow any gas to pass through one or more of any connected parts, such as, but not limited to any, inbound gas vent(s) (4385), outbound air/gas vent(s)(4390), vent(s) opening(s) (4355), vent cover door(s) (3930), hose(s) (4380), and hose connection(s) (4420), and function effectively as a system for the effective movement, passage, and/or transfer, of any air or gas(s) to, from, and/or through, any vent(s) (4385) (4390) and hose(s) (4380), in any room(s) and/or connected space(s) (4410).

Figure 12:
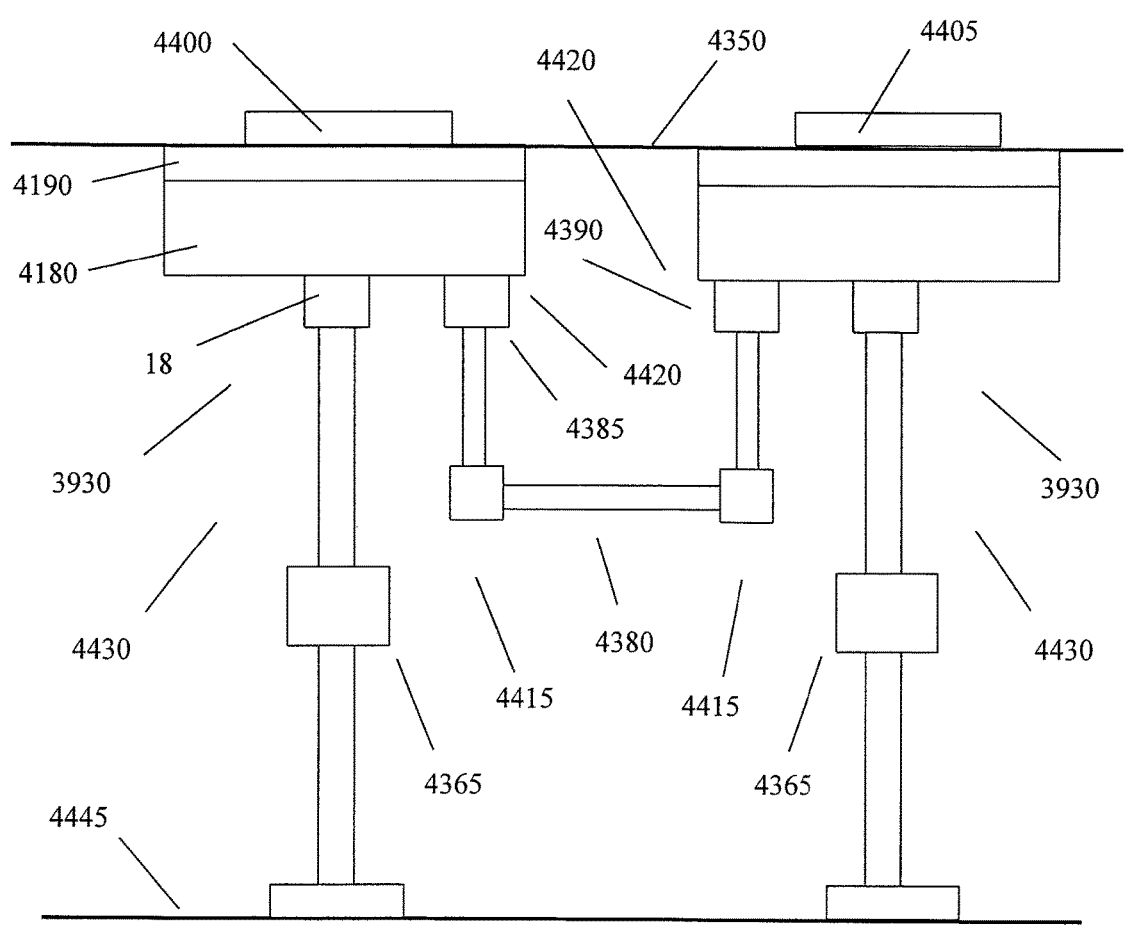
Figure 13:
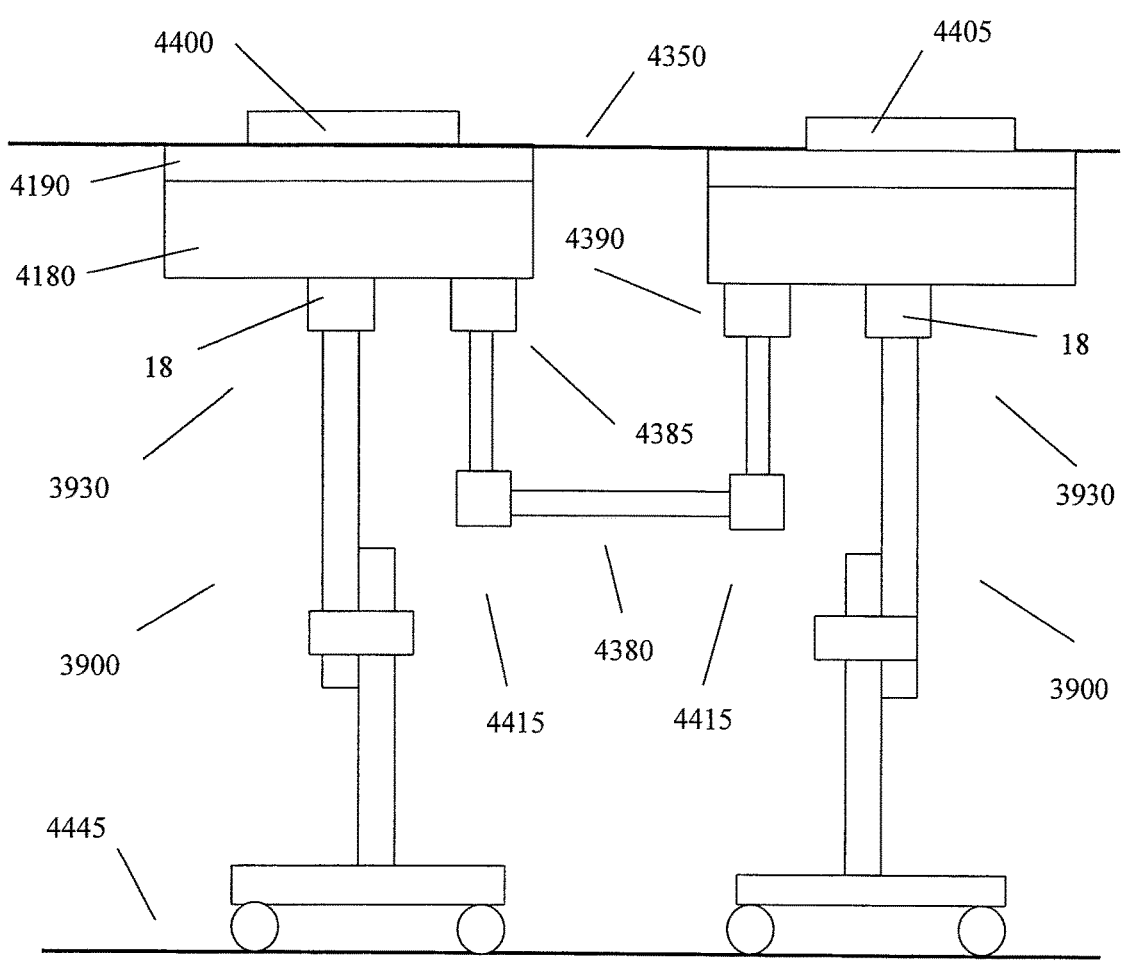
Figure 14:
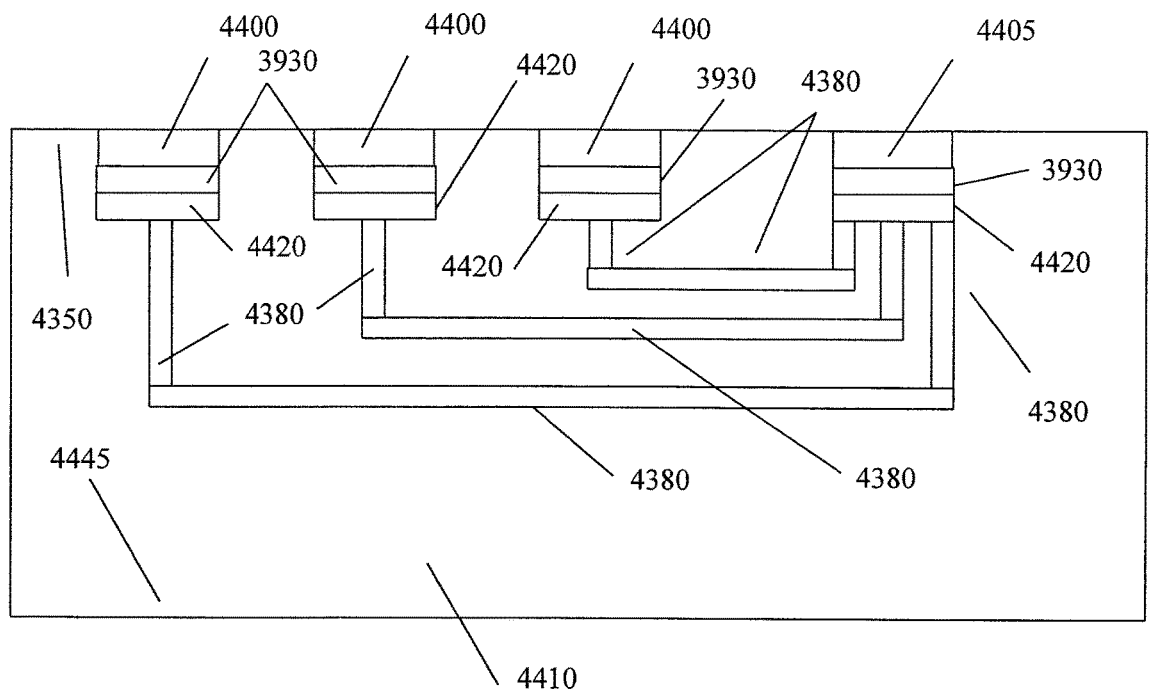
Figure 15:
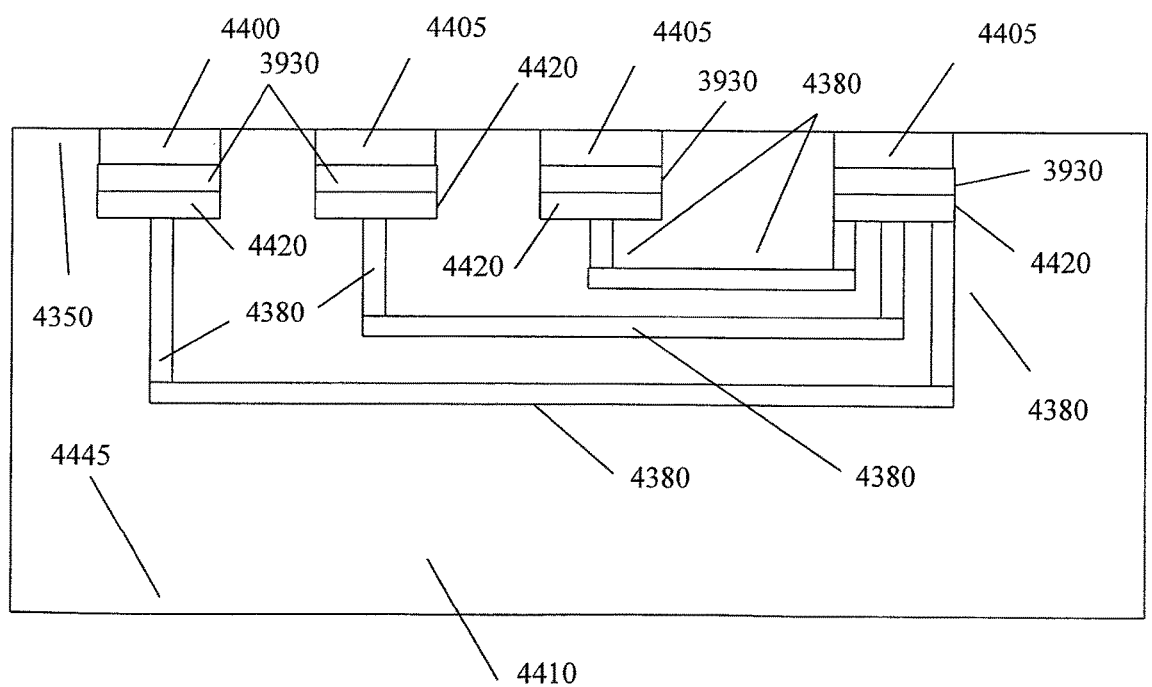

According to FIGS. 12-13, it is preferred that two separate vent cover and hose bypass systems (4415) are each interfaced with a manually adjustable vent cover holding and sealing apparatus (4430) as shown in FIG. 12, and an automated vent cover apparatus (3900) as shown in FIG. 13, where both apparatus do not include any vacuum release door (10) and vacuum break opening (15).

Referring to FIGS. 12-13 and without limitation, the vent cover door (3930) belonging to a first vent cover and hose bypass system (4415), effectively seals an air/gas entry vent (4400), while another separate vent cover door (3930) belonging to another second vent cover and hose bypass system (4415), effectively seals an air/gas exit vent (4405). Any type of support device may be used to force the cover plate (4180) against the gas entry vent (4400) or the gas exit vent (4405), such as the painter's pole (4365), a collapsible mobile tripod (3940), or any other suitable manual or automated support device.

At least one hose (4380) connects the first vent cover and hose bypass system (4415) to the second vent cover and hose bypass system (4415). The hose(s) (4380) effectively connect to each vent cover door (3930) via at least one hose connection(s) (4420). More specifically, the inbound air/gas hose connection (4385) effectively connects the hose (4380) to the vent cover door (3930) that effectively covers and/or seals the air/gas entry vent (4400), while the same hose (4380) effectively connects with the outbound air/gas hose connection (4390) that connects with the vent cover door (3930) that effectively covers and/or seals the air/gas exit vent (4405). The flow of air/gas bypasses flowing into the enclosed space and flows back into the ventilation system.

With reference to FIGS. 10-27, and without limitation, an apparatus and method of another embodiment of the present invention, can also relate generally to the cleaning, sanitization, disinfection, sterilization, and/or decontamination, of the interior and/or exterior, and/or any other part, of one or more of any, air duct(s), air duct system(s), air supply duct(s), air supply trunk line(s), air return trunk line(s), air outlets, air inlets, air return duct(s), air shaft(s), hose(s) (40)(4380), means to channel, stop, restrict, and/or direct air/gas(s), and/or any other conduit(s) to move any air and/or gas(s) through, to, and/or from, one or more of any, HVAC equipment, room(s) (4410), area(s), and/or building(s), (Herein called "Air Duct(s)") (4455) that are used to supply any air and/or gas(s) that is heated, cooled, humidified, dehumidified, blown, pumped, and/or filtered, to various room(s) (4410), space(s), building(s), and/or building area(s), and are also used to return any air from these various room(s) (4410), space(s), building(s), and/or building area(s) back to the various HVAC part(s) and equipment(s) (4465), as well as any suitable and effective means known to those skilled in the art used for, heating air, moving air, delivering air, ventilating air, filtering air, processing air, humidifying air, dehumidifying air, adding fresh air, and/or cooling air, as well as any other associated system(s), equipment(s), part(s) and component(s) known to those skilled in the art such as, but not limited to any, air/gas(s) valve(s) (not shown), air/gas(s) diversion apparatus(s) (not shown), air duct(s) (4455), air duct(s) system(s) (4460), air/gas entry vent(s) (4400), air/gas exit vent(s) (4405), and/or vent opening(s) (4355) (Herein all generally called "HVAC part(s) and equipment(s)") (4465). Without being limited, air duct system(s) (4460) can include but are not limited to, one or more of any effectively connected air duct(s) (4455). Without being limited, the said room(s) (4410) can have one or more of any suitable floor(s) (4445). Also, and without being limited, the one or more of any, HVAC system(s), air duct(s) (4455), and/or air duct(s) system(s), within any building(s) (4470), can connect with one or more of any suitable and effective apparatus(s) that can be used for one or more of any uses and activities such as, but not limited to any, heating air, moving air, delivering air, ventilating air, filtering air, processing air, humidifying air, dehumidifying air, adding fresh air, and/or cooling air (Herein collectively called "HVAC Unit(s)" (4610)). Without being limited, many building(s) (4470) known to those skilled in the art use at least one HVAC unit(s) (4610) to heat air, move air, deliver air, ventilate air, filter air, process air, humidify air, dehumidify air, add fresh air, and/or cool air, that is flowed and/or circulated through one or more of any area(s) and room(s) (4410) of any building(s) (4470). Without being limited, the HVAC part(s) and equipment(s) (4465) can also include one or more of any suitable HVAC unit(s) (4610).

Without being limited, the present invention can also relate generally to the cleaning, sanitization, disinfection, sterilization, and/or decontamination, of the interior and/or exterior, and/or any other part, of one or more of any part(s) and component(s) associated with any, filtering of air/gas(s), heating of air/gas(s), cooling of air/gas(s), humidification of air/gas(s), dehumidification of air/gas(s), movement of air/gas(s), adding fresh air, ventilation of any air, including any part(s) and/or apparatus(s) of any HVAC unit(s) (4610), and/or any other HVAC part(s) and equipment(s) (4465), as well as any other associated parts and components used to heat, humidify, dehumidify, ventilate, filter, move, and/or cool, any air and/or gas(s) that is flowed within, into, through, and/or out of, various residential, commercial, industrial, and/or healthcare building(s) and/or structure(s) (Herein called "Building(s)" (4470), as well as any means to carry, transmit, and/or pipe, any air/gas(s) flow(s) within any building(s) (4470), such as, but not limited to any, air duct(s) (4455), air duct system(s) (4460), air/gas entry vent(s) (4400), air/gas exit vent(s) (4405), air supply duct(s) (4515), air return duct(s) (4520), vent opening(s) (4355), air handler(s) (not shown), register(s) (not shown), grilles (not shown), blower(s) and fan(s) (not shown), duct fan(s) (4535), and any other associated part(s), motor(s), housing(s), piping(s), air plenum(s) (not shown), drain pan(s) (not shown), air cleaner(s) (not shown), heat exchanger(s) (not shown), coil(s) (not shown), and/or chill coil(s) (not shown), of any HVAC part(s) and equipment(s) (4465) and/or HVAC unit(s) (4610) known to those skilled in the art (Herein collectively called "HVAC Part(s) and Equipment" (4465)). Without being limited, air duct(s) (4455) can include one or more of any, pipe(s), tube(s), and/or conduit(s), preferably and without limitation, that are effective, through which any air/gas(s) can flow through various building(s) (4470) and to and from any HVAC unit(s) (4610) as well as any area(s) and room(s) (4410) located in various building(s) (4470), and also includes any air duct(s) such as, but not limited to any, air duct system(s) (4460), air shaft(s) (4472), air supply duct(s) (4515), and air return duct(s) (4520).

Without being limited, the present invention also relates generally to the use of one or more of any suitable and effective means, known to those skilled in the art, to generate, administer, distribute, flow, deliver, disperse, and/or transmit (Herein called "Agent Dispenser(s)" or a "device for supplying a treatment substance) (4505) one or more of any, substance(s), agent(s), chemical(s), chemistry(s), and/or molecule(s), in any suitable and effective quantity, and in one or more of any suitable and effective form(s), such as, but not limited to any, gas(s), vapor(s), aerosol(s), dry aerosol(s), and/or liquid aerosol(s) (Herein called "Deployed Agent(s)") (4510), to one or more of any area(s), surface(s), and/or space(s), such as, but not limited to, the interior of, inside of, within, and/or on, any targeted surface(s) of any, air duct(s) (4455), room(s) (4410), enclosure(s), compartment(s), air shaft(s), means to channel and/or direct air (not shown), vent(s) (4400)(4405), orifice(s), hose(s) (40)(4380), vent bypass system (4415), conduits to move any air flow(s), air duct system(s) (4460), HVAC unit(s) (4610), as well as any HVAC part(s) and equipment(s) (4465) and HVAC system related part(s) and component(s), for one or more of any purpose(s) such as, but not limited to, killing, destroying, neutralizing, and/or decontaminating, one or more of any pathogen(s) and/or microorganism(s) such as, but not limited to any, virus(s), bacteria(s), mold(s), fungus(s), and/or spore(s), that may be present on any of these surface(s), targeted surface(s), and/or suspended in any air and/or gas(s). The agent dispenser(s) (4505) and the current invention can also be used for other foreseeable purposes such as, but not limited to, deploying any suitable and effective aerosol(s) for various purposes such as, but not limited to, plugging holes in any air duct(s) (4455), air duct(s) system(s) (4460), and/or HVAC part(s) and equipment(s) (4465) and HVAC system(s), all in a manner known to those skilled in the art, as well as encapsulating any particles within, inside of, and/or on any, air duct(s) (4455), air duct(s) system(s) (4460), and/or HVAC part(s) and equipment(s) (4465), in a manner known to those skilled to the art. Without being limited, the deployed agent(s) (4510) can be administered and/or deployed into the various, air duct(s) (4455), air duct(s) system(s) (4460), any suitable and effective part of any vent bypass system(s) (4415), and/or HVAC part(s) and equipment(s) (4465), at any suitable and effective, concentration(s), quantity(s), air flow velocity(s), air speed(s), flow rate(s), density(s), particle size(s), ingredient number(s), temperature(s), mass concentration(s), time interval(s), concentration(s), and/or for any treatment and exposure time(s). Without being limited, the one or more agent dispenser(s) (4505) can also include internally and/or externally in its design, one or more of any means to move, disperse, inject, and/or deploy, the one or more deployed agent(s) (4510), such as, but not limited to one or more of any suitable and effective blower(s), fan(s), and/or air pump(s).

Without being limited, the one or more agent dispenser(s) (4505) can include, but is not limited to any, vaporized hydrogen peroxide (VHP) gas deployment system, aerosol containing hydrogen peroxide deployment system, ozone gas deployment system, aerosol containing ozone deployment system, chlorine dioxide gas deployment system, aerosol containing chlorine dioxide deployment system, peroxyacetic acid (PAA) gas deployment system, aerosol containing peroxyacetic acid (PAA) deployment system, ultrasonically derived aerosol(s), and/or any other effective airborne systems, technologies, and methods, to administer, distribute, flow, blow, deliver, disperse, and/or transmit, one or more of any, substance(s), agent(s), chemical(s), chemistry(s), molecule(s), or otherwise any suitable and effective deployed agent(s) (4510), known to those skilled in the art for purposes including, but not limited to, treating, disinfecting, sterilizing, sanitizing, decontaminating, plugging, and/or encapsulating, various surfaces, part(s) (4465), and/or area(s).

It is known to those skilled in the art that any, air duct(s) (4455), air duct system(s) (4460), air shafts (4472), air conduit(s), air filters, means to hold or mount any air filter(s), and/or any other HVAC part(s) and equipment(s) (4465) known in the art, can harbor and/or be contaminated with any, virus(s), mold(s), fungus(s), bacteria(s), spore(s), contaminate(s), and/or pathogen(s). Without being limited, this can especially be a problem with buildings (4470) that have "sick building syndrome" due to the presence of pathogens such as, but not limited to any, mold and fungus growth within, inside of, and/or on, any, air duct(s) (4455), air duct(s) system(s) (4460), and/or HVAC part(s) and equipment(s) (4465), that are used to move air into, within, out of, and/or throughout, one or more of any building(s) (4470) and/or one or more of any room(s) (4410) within any building(s) (4470). Without being limited, various industries such as, but not limited to, the pharmaceutical, biotechnology, medical device, and biomedical industry, are also concerned with pathogen safety and the microbiological cleanliness within, inside of, and/or on, any, air duct(s) (4455), air duct(s) system(s) (4460), and/or HVAC part(s) and equipment(s) (4465) that are used to move air into, within, out of, and/or throughout, one or more of any room(s), isolated clean space(s), clean room(s), system of clean room(s), system of clean space(s) (Herein also called "Room(s)") (4410) and/or building(s) (4470). Without being limited, the healthcare industry is also increasingly concerned with pathogen safety and the microbiological cleanliness within, inside of, and/or on, any, air duct(s) (4455), air duct(s) system(s) (4460), and/or HVAC part(s) and equipment(s) (4465) that are used to move air into, within, out of, and/or throughout, one or more of any room(s) (4410) and/or building(s) (4470), especially as the world has now entered the end of the antibiotic era, and especially with the new threat that is reported with the fungus C. auris.

It is also known to those skilled in the art that the cleaning and/or treating of any, air duct(s) (4455), air duct(s) system(s) (4460), and/or HVAC part(s) and equipment(s) (4465) can be a labor and time intensive process. For example, and without being limited, one or more of any suitable and effective steps known to those skilled in the art, can be taken to effectively clean, sanitize, disinfect, sterilize, and/or decontaminate, the one or more of any area(s), surface(s), and/or space(s), on and/or within any, air duct(s) (4455), hose(s) (40)(4380), vent bypass system(s) (4415), air duct(s) system(s) (4460), and/or HVAC part(s) and equipment(s) (4465), such as but not limited to: (a) mechanically scrubbing, mechanically hitting, air whipping, air washing, air brushing, hitting surface(s) with compressed air from one or more air nozzle(s) outlets, agitating, brushing, and/or wiping, the various targeted surface(s) of these various parts, space(s), and/or area(s), for purpose(s) such as, but not limited to, loosening and/or removing any, foreign object debris, contaminant(s), pathogen(s), organism(s), dirt, dust, debris, and/or residue(s), that may have accumulated within, inside of, and/or on, the various air duct(s) (4455), air duct(s) system(s) (4460), and/or HVAC part(s) and equipment(s) (4465) (Herein called "Loosening the Contamination(s)"), (b) vacuuming the various air duct(s) (4455), air supply duct(s) (4515), hose(s) (40)(4380), vent bypass system(s) (4415), air return ducts (4520), and various HVAC part(s) and equipment(s) (4465), with one or more of any effective tool(s) and/or apparatus(s) known to those skilled in the art that can be used for vacuuming these various part(s), component(s), space(s), and/or conduit(s), by pulling any effective vacuum on any and/or all part(s) of any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465), sealed zone(s) (4532), and/or one or more of any sealed air/gas flow system(s) (4530), and/or by blowing or moving any effective airflow and quantity of air through these various part(s), component(s), space(s), and/or conduit(s), at one or more of any effective time(s) and for any suitable and effective duration of time(s), to remove any foreign object debris and/or residue(s) that may have accumulated within, inside of, and/or on, any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and various HVAC part(s) and equipment(s) (4465), sealed zone(s) (4532), and/or one or more of any sealed air/gas flow system(s) (4530) (Herein called "Collecting the Contaminant(s)"), and/or (c) administering, distributing, flowing, delivering, dispersing, and/or transmitting, one or more of any, deployed agent(s) (4510), substance(s), agent(s), chemical(s), chemistry(s), and/or molecule(s), such as, but not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), by one or more of any suitable and effective agent dispenser(s) (4505), to clean, sanitize, disinfect, sterilize, and/or decontaminate, the one or more of any area(s), surface(s), and/or space(s), on and/or within any, conduit(s), part(s), space(s), area(s), hardware(s), such as, but not limited to any, air duct(s) (4455), hose(s) (40)(4380), vent bypass system(s) (4415), air duct(s) system(s) (4460), and/or HVAC part(s) and equipment(s) (4465) (Herein called "Treating the Surfaces"). Without being limited, the "loosening of the contamination" step can also be combined with the "collecting the contaminants" step at the same time. Also, without being limited, the various steps and activities of "loosening of the contamination", "collecting the contaminant(s)", and "treating the surfaces", can all be combined at the same time. It is preferred, without limitation, that the "treating the surface(s)" step is performed after the steps of "loosening of the contamination(s)" and "collecting the contaminant(s)".

The current art has, without being limited, multiple problems known to those skilled in the art, that can be solved with the current invention. First, and without being limited, it can be difficult to pull and/or establish an effective vacuum or establish an effective positive airflow pressure, on and/or through the one or more air duct(s) (4455), system of air duct(s) (4460), and/or HVAC system(s) known to those skilled in the art, any sealed off and/or isolated targeted zone(s) (4532)(4540) of air duct(s) (4455), and/or air duct system(s) (4460), to clean in various ways known to those skilled in the art and/or chemically treat with various methods previously mentioned including, but not limited to any, effective airborne surface treatment method(s), for one or more of any space(s), location(s), part(s) and component(s) such as, but not limited to any, building(s) (4470), air duct(s) (4455), air duct system(s) (4460), isolated air duct(s) (4540), sealed zone(s) (4532), isolated air duct system(s), unisolated targeted zone(s) of HVAC part(s) and equipment(s) (4465) and air duct(s), isolated targeted zone(s) of HVAC part(s) and equipment(s) (4465) and/or air duct(s) (4550), and/or HVAC system(s) known to those skilled in the art, because of one or more of various limiting factors known to those skilled in the art can be such as, but not limited to: (a) the total length of all of the combined air duct(s) (4455) and/or air duct(s) system(s) (4460), in the building(s) (4470), targeted area(s) of the building(s) (4470), and/or HVAC system(s) known to those skilled in the art, can be excessively long to achieve an effective outcome, and (b) one or more of any air/gas(s) supply duct(s) (4515) and/or return duct(s) (4520) can both connect with, communicate with, and/or enter into any, same or common room(s), area(s), and/or connected space(s) (4410), contributing to a loss of the needed air/gas(s) pressures or vacuum that is needed to be established for any effective outcome(s), cleaning(s), and/or surface treatment(s). Second, and without limitation, one or more of any air duct(s) (4455) and more specifically, and without limitation any, air/gas(s) supply duct(s) (4515) and/or air/gas(s) return ducts (4520), that are directly and/or indirectly connected with one or more of any agent dispenser(s) (4505), can both connect with, communicate with, and/or enter into any, same or common room(s), area(s), and/or connected space(s) (4410), resulting in deployed agent(s) (4510), that are emitted and/or deployed by the agent dispenser(s) (4505), entering these said room(s), area(s), and/or connected space(s) (4410), when this result and/or situation is not desired and/or needs to be avoided for reasons known to those skilled in the art.

Without being limited, personnel such as, but not limited to any, HVAC cleaning personnel, technicians, their co-workers, and/or any other associated people, who loosen the contamination(s), collect the contaminant(s), and/or treat surfaces, of any, air duct(s) (4455), air duct(s) system(s) (4460), and/or HVAC part(s) and equipment(s) (4465), in situation(s) known to those skilled in the art, may need to effectively seal, cover, and/or block off, one or more of any, air duct(s) (4455), HVAC part(s) and equipment(s) (4465), and/or one or more of any section(s) and/or zone(s) (4532) (4525)(4530)(4545)(4550) including any HVAC part(s) and equipment(s) (4465), such as, but not limited to any, air duct(s) (4455), air duct(s) system(s) (4460), air/gas entry vent(s) (4400), air/gas exit vent(s) (4405), vent opening(s) (4355), and/or any other HVAC part(s) and equipment(s) (4465) known to those skilled in the art, in one or more area(s), location(s), and/or place(s), for purposes including, but not limited to, effectively loosening the contamination(s), collecting the contaminant(s), and/or treating the surfaces, of any, air duct(s) (4455), air duct(s) system(s) (4460), and/or HVAC part(s) and equipment(s) (4465). In addition, and without limitation, one or more hole cut(s) are sometimes also made into these various HVAC part(s) and equipment(s) (4465) such as, but not limited to any, air duct(s) (4455), air duct(s) system(s) (4460), air shaft(s) (4472), and/or any other HVAC part(s) and equipment(s) (4465), in order to effectively loosen the contamination(s), collect the contaminant(s), and/or treat the surfaces, of any various, air duct(s) (4455), air duct(s) system(s) (4460), and/or HVAC part(s) and equipment(s) (4465), including for one or more of any isolated section(s) and/or zone(s) (4540) of one or more of any, air duct(s) (4455), air duct(s) system(s) (4460), and/or any other HVAC part(s) and equipment(s) (4465), that are cleaned and/or treated.

Without being limited, a major problem in the current art is that the various air duct(s) (4455), air duct(s) system(s) (4460), and/or HVAC part(s) and equipment(s) (4465), such as, but not limited to any, supply duct(s) (4515), and return ducts (4520), and/or any other HVAC part(s) and equipment(s) (4465), especially and without limitation the one or more of any supply duct(s) (4515) and/or return duct(s) (4520), that both connect with, communicate with, and/or enter into, the same or common room(s), area(s), and/or connected space(s) (4410), could not be connected in any effective, communicating line, circuit, open circuit, closed circuit, sealed circuit, sealed and communicating line, including but not limited for any, entire HVAC system for a building, entire system of directly and/or indirectly communicating air duct(s) in a building(s) (4470), isolated section(s) and/or zone(s) (4540) and/or unisolated section(s) and/or zone(s) (4545) of one or more of any HVAC part(s) and equipment(s) (4465) such as, but not limited to any, air duct(s) (4455), air duct(s) system(s) (4460), air/gas(s) supply duct(s) (4515), and/or air/gas(s) return ducts (4520).

More specifically, and without limitation, the various air duct(s) (4455), and more specifically the various air duct(s) (4455), supply duct(s) (4515), and/or return ducts (4520) for an HVAC system in any building, flow air into and/or out of various room(s), zone(s), area(s), and/or zone(s) of room(s) and/or area(s) (Herein called "Room(s)" (4410)). These various air duct(s) (4455), and more specifically the various air/gas(s) supply duct(s) (4515) and/or air/gas(s) return ducts (4520) connect via these various room(s), zone(s), area(s), and/or zone(s) of room(s) and/or area(s) (4410), in a manner known in the art, where one or more supply duct(s) (4515) can connect or communicate with these one or more various room(s), zone(s), area(s), and/or zone(s) of room(s) and/or area(s) (4410) to supply air into these location(s) that is, without limitation, treated, heated, filtered, dehumidified, humidified, and/or cooled, by the various HVAC unit(s) (4610) and HVAC part(s) and equipment(s) (4465), and one or more return ducts (4520) can also connect or communicate with these one or more various room(s), zone(s), area(s), and/or zone(s) of room(s) and/or area(s) (4410) to return the air from these various room(s), zone(s), area(s), and/or zone(s) of room(s) and/or area(s) (4410), back to the various HVAC unit(s) (4610) and HVAC part(s) and equipment(s) (4465) so the returned air can be treated, heated, filtered, dehumidified, humidified, and/or cooled. The air/gas(s) supply duct(s) (4515) and the air/gas(s) return ducts (4520) for these various room(s), zone(s), area(s), and/or zone(s) of room(s) and/or area(s) (4410) are not directly connected since they are used to flow air into and out of these various area(s) and room(s) (4410).

Without being limited, this can present problems such as, but not limited to, the debris from cleaning the various air duct(s) (4455) can be deposited into the room(s) (4410) where the various air duct(s) (4455) connect, the needed one or more of any effective air/gas(s) pressure(s) and/or vacuum(s) for any effective outcome(s) for any cleaning(s) and/or surface treatment(s) such as, but not limited to any, "loosening of the contamination", "collecting the contaminant(s)", and/or "treating the surfaces", cannot be kept throughout location(s), part(s), component(s), space(s), and area(s) such as, but not limited to any, air duct(s) (4455), air duct(s) system(s) (4460), HVAC part(s) and equipment(s) (4465), HVAC unit(s) (4610), because the various air duct(s) (4455) connect with the various area(s) and room(s) (4410), and the deployed agent(s) (4510), that are emitted and/or deployed by the agent dispenser(s) (4505), used to treat various surface(s) such as, but not limited to any surface(s) inside any air duct(s) (4455), can enter into the various room(s) (4410), unless the various air duct(s) that open into and communicate with the various area(s) and room(s) (4410) such as, but not limited to any, supply duct(s) (4515) and return ducts (4520) are effectively sealed. Without being limited, and as known to those skilled the art, entire HVAC system may not be effectively and completely treated from one or more effective input location(s) because the various air duct(s) (4455), supply duct(s) (4515), and return ducts (4520), are not all effectively interconnected as one continuous sealed and communicating system of air duct(s) (4455).

Also, without being limited, the present invention, allows one or more of any, air duct(s) (4455), air duct system(s) (4460), supply duct(s) (4515), return ducts (4520), and/or HVAC parts and equipment(s) (4465), to be effectively, connected, interconnected, and/or seamlessly interconnected, preferably and without limitation, with the use one or more of any suitable and effective vent bypass system(s) (4415) and associated hose(s) (40)(4380), in any effective, communicating line, communicating conduit, circuit, open circuit, closed circuit, sealed circuit, sealed and communicating line, sealed and communicating system of conduit(s), sealed and communicating conduit(s), also including but not limited to any, isolated zone(s) (4540) and/or unisolated section(s) zone(s) (4545) and/or room(s) (4410) of one or more of any HVAC parts and equipment(s) (4465) such as, but not limited to any, air duct(s) (4455), air duct(s) system(s) (4460), supply duct(s) (4515), and/or return ducts (4520). This communicating system of one or more air duct(s) (4455), air duct(s) system(s) (4460), supply duct(s) (4515), and/or return ducts (4520) can be, without limitation, cleaned in any effective manner known to those skilled in the art, and more preferably treated with one or more of any deployed agent(s) (4510), to clean and/or treat any surfaces within these conduits and any connected HVAC part(s) and equipment(s) (4465) and HVAC unit(s) (4610) such as, but not limited to, those used for any, filtering, heating, humidification, dehumidification, movement, ventilation, and/or cooling, of any air and/or air flow(s).

Without being limited, the various air, gas(s), and/or deployed agent(s) (4510), can flow within the various air duct(s) (4455), air duct(s) system(s) (4460), and HVAC part(s) and equipment(s) (4465), at one or more of any suitable and effective flow rate(s), flow speed(s), flow velocity(s), pressure(s), and/or vacuum(s), and it is preferred without limitation, that these flow characteristic(s), pressure(s), and or vacuum(s), that can be applied and/or used by those skilled in the art, within the one or more air duct(s) (4455), air duct(s) system(s) (4460), and HVAC part(s) and equipment(s) (4465), are at least effective.

With reference to FIGS. 16-20 and 23, and according to an embodiment, and without limitation, the one or more of any air duct(s) (4455), in any building(s) (4470), that supply air/gas(s) from one or more of any HVAC part(s) and equipment(s) (4465) and HVAC unit(s) (4610) such as, but not limited to, those used for filtering, heating, humidification, dehumidification, movement, ventilation, and/or cooling, of any air, to any one or more area(s) and/or room(s) (4410), and more specifically and without limitation, the one or more of any air/gas entry vent(s) (4400), can be effectively, and preferably and without limitation, removably connected, either directly and/or indirectly, in any effective sealed manner known in the art, but preferably and without limitation with one or more of any suitable and effective vent bypass system(s) (4415) and/or hose(s) (40)(4380), to one or more of any air duct(s) (4455) that return air (4520) from any of the said one or more area(s) and/or room(s) (4410) back to the said HVAC part(s) and equipment(s) (4465) and HVAC unit(s) (4610), and more specifically and without limitation, to the one or more of any air/gas exit vent(s) (4405) that connect to the said return ducts (4520), so that the one or more, and more preferably and without limitation all, of the various air duct(s) (4455)(4460)(4465)(4515) (4520) and the various parts of the HVAC part(s) and equipment(s) (4465) and HVAC unit(s) (4610), known those skilled in the art, can all be effectively connected and/or linked together and can effectively communicate, and any, air, gas(s), and/or deployed agent(s) (4510), can effectively flow through, and more preferably and without limitation, circulate through and around, the effectively sealed and connected system of the one or more of any air duct(s) (4455), air supply duct(s) (4515), air/gas(s) entry vent(s) (4400), air/gas exit vent(s) (4405), air return ducts (4520), vent bypass system(s) (4415), hose(s) (40)(4380), and various HVAC part(s) and equipment(s) (4465) and HVAC unit(s) (4610), that is established. This can prevent the deployed agent(s) (4510) from entering or being deployed into any room(s) and/or area(s) (4410) where there are any air/gas entry vent(s) (4400) and/or air/gas exit vent(s) (4405). It is preferred, without limitation, that the various air duct(s) (4455)(4460) (4465)(4515)(4520) are effectively connected and communicate with one another using the one or more vent bypass system(s) (4415), it is more preferred without limitation, that the one or more air supply duct(s) (4515) are effectively connected and communicate with the one or more air return and/or air exit duct(s) (4520)(4455) using the one or more vent bypass system(s) (4415), it is even more preferred, without limitation, that the one or more air/gas(s) entry vent(s) (4400) are effectively connected and communicate with the one or more air/gas exit vent(s) (4405) using the one or more vent bypass system(s) (4415).

According to FIGS. 16-24, and without limitation, the deployed agent(s) (4510) can be, deployed, injected, administered, distributed, flowed, delivered, dispersed, and/or transmitted by one or more agent dispenser(s) (4505), in any suitable and effective manner known to those skilled in the art, into, interfaced with, removably interfaced with, and/or at, one or more of any suitable and effective location(s) of this said sealed and connected system of one or more of any, part(s), component(s), area(s), location(s), such as, but not limited to any, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), HVAC unit(s) (4610), and/or HVAC part(s) and equipment(s) (4465), that is established. When these one or more of any, part(s), component(s), area(s), location(s), such as, but not limited to any, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), HVAC unit(s) (4610), and/or HVAC part(s) and equipment(s) (4465), are effectively connected and sealed together, it is intended, without limitation, that the various room(s) and area(s) (4410) in which there are any air/gas(s) entry vent(s) (4400) and air/gas exit vent(s) (4405), are not exposed to the deployed agent(s) (4510). However, in certain situations known to those skilled in the art, and without being limited, the deployed agent(s) (4510) can also enter one or more of any, room(s), zone(s), area(s) (4410), and/or zone(s) of room(s) and/or area(s) (4525), for purposes including, but not limited to, treating the air and/or various surface(s) within those space(s) and room(s) (4410) with the deployed agent(s) (4510).

It is preferred, without limitation, that the deployed agent(s) (4510) are injected, administered, distributed, flowed, dispersed, transmitted, and/or flowed, into this said connected system of air duct(s) (4455) and the various HVAC part(s) and equipment(s) (4465) and/or HVAC unit(s) (4610), at least at or effectively near the one or more of any suitable and effective location(s) of any HVAC part(s) and equipment(s) (4465) and/or HVAC unit(s) (4610) such as, but not limited to, those used for any, filtering, heating, humidification, dehumidification, movement, ventilation, and/or cooling, of any air, and more preferably, and without limitation, in the area of any suitable fresh air intake and/or fresh air supply for the HVAC part(s) and equipment(s) (4465) and/or HVAC unit(s) (4610), and even more preferably, and without limitation, after any HVAC part(s) and equipment(s) (4465) and/or HVAC unit(s) (4610) used for moving and/or circulating air/gas(s) throughout various room(s) (4410) and/or building(s) (4470). It is more preferred, without limitation, that there are at least one, but more preferably, and without limitation, multiple treatment locations, and even more specifically one or more effective location(s), where the deployed agent(s) (4510) are injected and/or flowed into this said connected system of various, air duct(s) (4455), conduit(s), hose(s) (40)(4380), and the various HVAC part(s) and equipment(s) (4465) and/or HVAC unit(s) (4610), and even more specifically, and without limitation, along the connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air, and more preferably, and without limitation, in the area of the fresh air intake and/or supply of the HVAC part(s) and equipment(s) (4465) and/or HVAC unit(s) (4610), and even more preferably, and without limitation, after any HVAC part(s) and equipment(s) (4465) and/or HVAC unit(s) (4610) used for moving any air and/or gas(s) (Herein called "Sealed Air/Gas Flow System" (4530), all in a manner known to those skilled in the art.

Also according to FIGS. 16-20 and FIG. 23, and without limitation, one or more of any suitable and effective, source(s) of pressurized air/gas(s), air pump(s), blower(s), fan(s), duct fan(s) (Herein called "Duct Fan(s)" (4535)), can also be located at and/or effectively integrated with, interfaced with, communicate with, and/or into, and preferably and without limitation, temporarily and/or removably, in a manner known to those skilled in the art, one or more of any suitable and effective location(s) such as, but not limited to any, air duct(s) (4455), sealed and connected system of one or more of any air duct(s) (4455), air gas(s) supply duct(s) (4515), air/gas(s) entry vent(s) (4400), air/gas exit vent(s) (4405), hose(s) (40)(4380), vent bypass system(s) (4415), orifice(s), air/gas(s) return ducts (4520), HVAC part(s) and equipment(s) (4465), HVAC unit(s) (4610), sealed zone(s) (4532), orifice(s), zone(s) of room(s) and/or area(s) (4525), sealed air/gas(s) flow system(s) (4530), isolated zone(s) (4540), unisolated section(s) zone(s) (4545), isolated targeted zone(s) of HVAC part(s) and equipment(s) (4465) and/or air duct(s) (4550), and/or one or more of any sealed air/gas flow system(s) (4530), and/or air duct system(s) (4460). Without limitation, the said duct fan(s) (4535) can move any suitable and effective quantity of any air, gas(s), vapor(s), and/or deployed agent(s) (4510), at any suitable and effective velocity, speed, cubic feet per minute, and/or volume of air/gas(s) flow(s).

Without being limited, the deployed agent(s) (4510), can be moved through any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), and/or HVAC unit(s) (4610) and various HVAC part(s) and equipment(s) (4465), sealed zone(s) (4532), and/or one or more of any sealed air/gas flow system(s) (4530), with one or more, including any effective combination(s) of, at one or more of any suitable location(s), any suitable and effective source(s) of pressurized air/gas(s), air pump(s), blower(s), fan(s), and/or any effective means to move any air/gas(s), such as, but not limited to any, duct fan(s) (4535), airflow source(s) used with any HVAC system(s) and/or HVAC unit(s) (4610) known to those skilled in the art, such as, but not limited to any HVAC unit(s) (4610) fan(s) and/or blower(s) that are a part of any HVAC unit(s) (4610), part(s), and/or component(s), that move air and/or gas(s) throughout one or more of any location(s), space(s), and/or area(s) such as, but not limited to any, building(s) (4470), room(s), zone(s), area(s) (4410), and/or zone(s) of room(s) and/or area(s) (4525), sealed air/gas(s) flow system(s) (4530), and/or sealed zone(s) (4532), as well as any source(s) of pressurized air/gas(s), air pump(s), blower(s), and/or fan(s), that are directly and/or indirectly a part of any agent dispenser(s) (4505). Without being limited, these one or more of any suitable and effective source(s) of pressurized air/gas(s), air pump(s), blower(s), fan(s), and/or any means to move any air/gas(s), can be located at one or more of any suitable and effective location(s) known to those skilled in the art, and can be operated at one or more of any suitable and effective time(s) and for any suitable and duration of time(s). Without being limited, the deployed agent(s) (4510) can be flowed in one or more of any suitable and effective direction(s) at any effective time(s) within any, air duct(s) (4455), air supply duct(s) (4515), air/gas(s) entry vent(s) (4400), air/gas exit vent(s) (4405), vent bypass system(s) (4415), hose(s) (40) (4380), orifice(s), air return ducts (4520), various HVAC part(s) and equipment(s) (4465) and/or HVAC unit(s) (4610), sealed zone(s) (4532), and/or one or more of any sealed air/gas flow system(s) (4530).

With reference to FIGS. 16-20 and FIG. 23, and without limitation, the one or more of any duct fan(s) (4535) can be effectively interfaced with and/or effectively communicate with, any, air duct(s) (4455), vent bypass system(s) (4415), hose(s) (40)(4380), connected system of air duct(s) (4455), HVAC part(s) and equipment(s) (4465) and/or HVAC unit(s) (4610), in any suitable and effective, configuration(s), mounting direction(s), and/or orientation(s). The airflow(s) from the said duct fan(s) (4535) can also, without limitation, flow in one or more of any suitable and effective direction(s). Also, and without being limited, the one or more duct fan(s) (4535) can suitably and effectively communicably and removably interface, preferably and without limitation in any hermetically sealed manner, and more preferably and without limitation, be effectively located to and/or within any, air duct(s) (4455), hose(s) (40)(4380), sealed zone(s) (4532), and/or one or more of any sealed air/gas flow system(s) (4530), in any effective manner known to those skilled in the art, but at least at and/or with one or more of any suitable and effective location(s) and/or part(s), of one or more of any sealed zone(s) (4532) and/or one or more of any sealed air/gas flow system(s) (4530) such as, but not limited to any, air duct(s) (4455), vent bypass system(s) (4415), hose(s) (40)(4380), connected system of air duct(s) (4460), and/or the various HVAC part(s) and equipment(s) (4465) and/or HVAC unit(s) (4610), and even more specifically the connected and sealed system of various air duct(s) (4455)(4460) (4530), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air.

Without being limited, the deployed agent(s) (4510) can be, deployed, injected, administered, distributed, flowed, delivered, dispersed, and/or transmitted, by the one or more said agent dispenser(s) (4505), in any suitable and effective manner and with any suitable and effective agent dispenser(s) (4505), known to those skilled in the art, at one or more of any suitable and effective, temperature(s), flow rate(s), flow speed(s), cubic feet per minute flow(s), mass flow(s), particle size(s), number mass(s), and/or concentration(s), of the air/gas(s) and/or deployed agent(s) (4510). It is preferred, without limitation, that the deployed agent(s) (4510) can move, flow, circulate, and/or completely circulate, through and/or throughout the one or more effectively connected and/or sealed, sealed zone(s) (4532), sealed air/gas flow system(s) (4530), air duct(s) (4455), conduit(s), hose(s) (40)(4380), HVAC part(s) and equipment(s) (4465) and/or HVAC unit(s) (4610), any connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or open system(s) (4565).

According to FIGS. 19-21, and without being limited, the one or more of the said sealed and connected system(s) of the one or more of any air duct(s) (4455), air supply duct(s) (4515), air/gas(s) entry vent(s) (4400), orifice(s), air/gas exit vent(s) (4405), vent bypass system(s) (4415), hose(s) (40)(4380), air return ducts (4520), and/or various HVAC part(s) and equipment(s) (4465) and/or HVAC unit(s) (4610), that is established, can also be confined and/or isolated to one or more of any suitable and effective zone(s) and/or area(s) (Herein called "Sealed Zone(s)" (4532)). It is preferred, without limitation, that the sealed zone(s) (4532) are effectively sealed and/or isolated in a manner and/or with one or more suitable and effective means known to those skilled in the art (Herein called "Air Duct Seal(s) (4555)". The sealed zone(s) (4532) can include and/or be, without limitation, any suitable and effective, size, air volume, number of air duct(s) (4455), number of air/gas(s) entry vent(s) (4400), number of air/gas exit vent(s) (4405), number of vent bypass system(s) (4415), number of hose(s) (40)(4380), number of HVAC part(s) and equipment(s) (4465), number of HVAC unit(s) (4610), number of air supply duct(s) (4515), number of air return duct(s) (4520), complexity, height, number of building(s) (4470), number of floor(s) (4560) of any building(s) (4470), and/or include one or more of any, room(s), zone(s), area(s), and/or zone(s) of room(s) and/or area(s) (4410). Also, according to FIGS. 16-20 and FIG. 23, and without being limited, one or more of any vent opening(s) (4355), air/gas(s) entry vent(s), and/or air/gas(s) exit vent(s), can also be effectively covered and/or sealed with one or more of any suitable and effective cover(s) and/or seal(s) (Herein called "Orifice Seal(s)") (4720) that can be any suitable and effective size(s), shape(s), design(s), thickness(s), length(s), width(s), height(s), material(s), and/or combination of material(s). Without being limited, the present invention, including but not limited to any of its embodiments, can apply to any, style of building(s), design of building(s), and number of stories or floors (4560) that any building may have including but not limited to any, one story and/or floor building(s) and/or multi story and/or floor building(s), known to those skilled in the art.

With reference to FIGS. 18 and 20, and without limitation, the deployed agent(s) (4510) and any accompanying air/gas(s) can also be, deployed, injected, and/or flowed, into one or more of any suitable and effective locations of any open and connected system(s) (4565) of various connected, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), conduit(s), hose(s) (40)(4380), and even more preferably, and without limitation, one or more of any suitable and effective location(s) of the connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610) (Herein called "Open System(s)" (4565)), where the deployed agent(s) (4510) are effectively deployed at least at one or more of any suitable and effective end(s) and/or beginning(s) (Herein called ("Start Location(s) of Open System" (4570)) of this said open system(s) (4565), and then flowed through the said various part(s), component(s), space(s), location(s), and conduit(s), and then exit at one or more of any other suitable and effective open end(s) (Herein called ("Open End Location(s) of Open System" (4575)) of this said open system(s) (4565). It is preferred, without limitation that the deployed agent(s) (4510) are at least, without limitation, deployed, injected, and/or flowed, into one or more additional suitable and effective location(s) of this said open system(s) (4565).

Without being limited, the one or more of any sealed air/gas flow system(s) (4530), sealed zone(s) (4532), and open system(s) (4565), can be any suitable and effective, size(s), shape(s), complexity(s), include multiple building (4470) level(s) or floor(s) (4560), and include both small and large connected and interconnected systems of various, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610).

Also, without being limited, the establishment of any sealed zone(s) (4532) and/or open system(s) (4565) can also be used to isolate, encompass, include, seal together, connect, and/or envelop, one or more of any, equipment(s), component(s), area(s), and/or space(s), such as, but not limited to any, fan(s), blower(s), duct fan(s) (4535), air duct(s) (4455), air duct system(s) (4460), filter assembly(s) (not shown), filter holding apparatus(s) (not shown), and/or any other HVAC part(s) and equipment(s) (4465) and/or HVAC unit(s) (4610), for various activities and/or any combination of any suitable and effective activities such as, but not limited to, loosening the contamination(s), collecting the contaminant(s), treating the surfaces, cleaning various surface(s), within and/or on these various part(s), equipment(s), area(s) and/or space(s). Without being limited, this can also be used for cleaning and treating various HVAC part(s) and equipment(s) (4465) and/or HVAC unit(s) (4610), as well as before, during, and/or after, changing and/or replacing any air/gas(s) filter(s) (not shown). Without being limited the one or more of any air/gas(s) filter(s) (not shown) located in these various location(s), such as, but not limited to inside various HVAC system(s) and component(s) and/or HVAC unit(s) (4610), can be treated with any effective deployed agent(s) (4510) before, during, and/or after their removal. It is preferred, without limitation, that the various filter holding apparatus(s) (not shown) are effectively treated with the deployed agent(s) (4510) for purposes including, but not limited to, the effective decontamination of their various surface(s), at least before any new air/gas(s) filter(s) (not shown) are installed, and after the old air/gas(s) filter(s) (not shown) are removed from any suitable filter holding apparatus(s) (not shown). The air/gas(s) filter(s) can be, without limitation, any suitable and effective filter(s) known to those skilled in the art, for any suitable and effective application(s) known to those skilled in the art.

Figure 21:
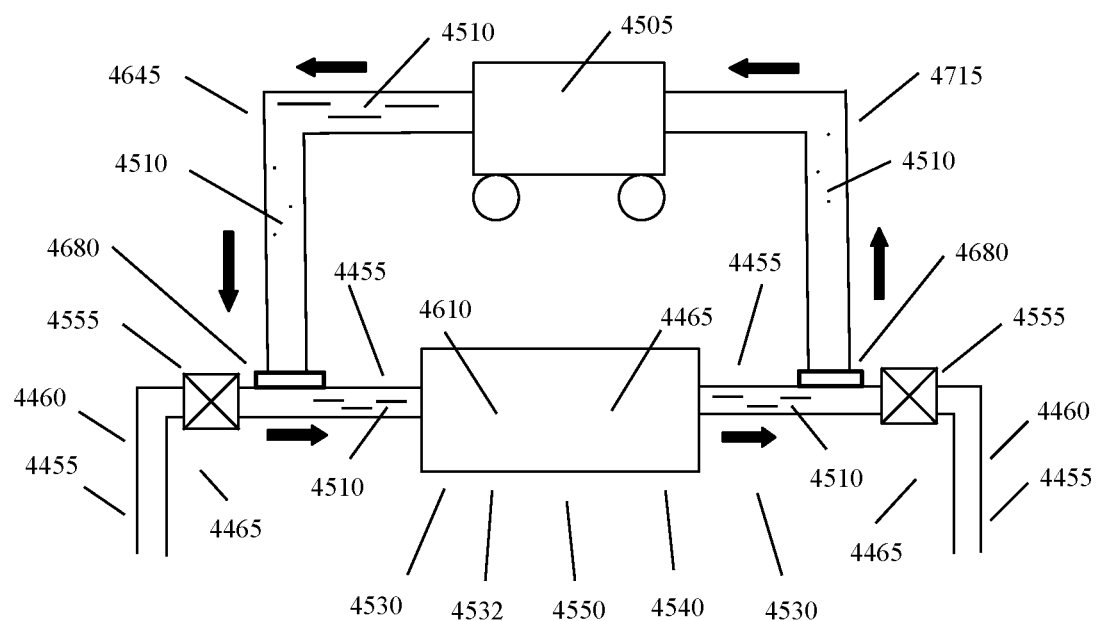

With reference to FIG. 21, and without being limited, one or more section(s) of any, air duct(s) (4455), air supply duct(s) (4515), air return duct(s) (4520), HVAC part(s) and equipment(s) (4465), HVAC unit(s) (4610), and/or HVAC system, can also be effectively sealed off in a manner known to those skilled in the art, but preferably and without limitation with any suitable number, size, and shape, of any effective air duct seal(s) (4555), so that they cannot communicate with other one or more of any connecting air duct(s) (4455), room(s) (4410), and/or system of air duct(s) (4460), so that one or more of any HVAC part(s) and equipment(s) (4465) and/or HVAC unit(s) (4610), such as, but not limited to, those used for any, filtering, heating, humidification, dehumidification, movement, ventilation, and/or cooling, of any air/gas(s), as well as any communicating air duct(s) (4455), can be subjected to the one or more of any of the said step(s) and/or activities such as, but not limited to, "Loosening the Contamination(s)", "Collecting the Contaminant(s)", and/or "Treating the Surfaces", on and/or within these various area(s), part(s), and/or space(s).

According to FIGS. 16-24, and without being limited, the one or more agent dispenser(s) (4505) can suitably and effectively communicably and removably interface, preferably and without limitation in any hermetically sealed manner, known to those skilled in the art, at or with one or more of any suitable and effective, part(s), location(s), component(s), area(s), and/or space(s), such as, but not limited to any, air duct system(s) (4460), sealed zone(s) (4532) sealed air/gas flow system(s) (4530), air duct(s) (4455), connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air.

Without being limited, the deployed agent(s) (4510) can be, deployed, injected, administered, distributed, flowed, delivered, dispersed, and/or transmitted, by the one or more said agent dispenser(s) (4505), in any suitable and effective manner known to those skilled in the art, at one or more of any suitable and effective, temperature(s), flow rate(s), flow speed(s), cubic feet per minute flow(s), mass flow(s), particle size(s), particle number(s), number mass(s), and/or concentration(s), of the air/gas(s) and/or deployed agent(s) (4510). It is preferred, without limitation, that the deployed agent(s) (4510) can move, flow, circulate, and/or completely circulate, through and/or throughout, the one or more of any area(s) such as, but not limited to any, effectively connected and/or sealed zone(s) (4532), sealed air/gas flow system(s) (4530), and/or zone(s) (4540).

Without being limited, the one or more of any air/gas entry vent(s) (4400) and the one or more of any air/gas exit vent(s) (4405), and/or any other entry and/or exit orifice(s), can be directly and/or indirectly connected with one or more of any suitable and effective conduit(s), tube(s), and/or hose(s) (40)(4380), and preferably and without limitation, with one or more of any suitable and effective vent bypass system (4415), so that air, deployed agent(s) (4510), and/or gas(s), may effectively pass from one or more of any air duct(s) (4455), and more particularly and without limitation, any air duct(s) (4455) that supply air/gas(s) (4515) to the one or more area(s) and/or room(s) (4410), preferably and without limitation through the one or more of any air/gas entry vent(s) (4400) and/or any other entry orifice(s), through the one or more of any conduit(s), tube(s), vent bypass system(s) (4415), and/or hose(s) (40)(4380), and preferably and without limitation through the one or more of any air/gas exit vent(s) (4405) and/or any other exit orifice(s), and then to one or more of any air duct(s) (4455) that return air/gas(s) (4520) to the one or more of any HVAC part(s) and equipment(s) (4465) and/or HVAC unit(s) (4610), and/or to one or more of any air duct(s) (4455) that reconnect, recirculate, and/or connect back, to one or more of any air duct(s) (4455) that supply air/gas(s) (4515) to the one or more of any area(s) and/or room(s) (4410).

It is preferred, without limitation, that all of the various air/gas(s) entry vent(s) (4400) and air/gas exit vent(s) (4405), that are preferably within, connected to, and/or communicating with, one or more of any, air duct(s) (4455), system of air duct(s) (4460), air supply duct(s) (4515), air return duct(s) (4520), sealed air/gas(s) flow system(s) (4530), sealed zone(s) (4532), isolated zone(s) (4540), within any building(s) (4470), and more preferably within an entire building(s) (4470), are effectively covered, and more preferred without limitation these air/gas(s) vent(s) (4400)(4405) are effectively removably sealed, and even more preferred without limitation these air/gas(s) vent(s) (4400)(4405) are effectively removably sealed in a manner that is hermetic or about hermetically sealed. Without being limited, these various air/gas(s) vent(s) (4400)(4405), and/or any other suitable and effective orifice(s) (not shown) that may be cut and/or made present in one or more of any suitable location(s) of any air duct(s) (4455), in a manner known to those skilled in the art, can be effectively covered and/or sealed with one or more of any suitable and effective means to cover and/or seal any air/gas(s) vent(s) (4400) (4405) and/or orifice(s) (not shown) known to those skilled in the art, such as, but not limited to any, vent cover apparatus(s) (3900), cover plate(s) (4180) that preferably and without limitation includes at least one effective seal(s) and/or sealing ring(s) (4190), vent bypass system(s) (4415), and/or air duct seal(s) (4555).

Also, and without being limited, it is preferred that these said one or more means to cover and/or seal any air/gas(s) vent(s) (4400)(4405) and/or orifice(s) (not shown), can also interface and connect with, and/or removably interface and connect with, in any manner known to those skilled in the art, one or more of any suitable and effective conduit(s), tube(s), and/or hose(s) (40) (4380), thus preferably forming one or more effective vent bypass system(s) (4415). Without being limited, the said means to cover and/or seal any air/gas(s) vent(s) (4400)(4405) and/or orifice(s) (not shown), such as, but not limited to any vent bypass system(s) (4415) can effectively directly and/or indirectly interface with, and/or removably interface with, in any manner known to those skilled in the art, one or more of any air duct(s) (4455) that supply air (4515) and/or air/gas(s) entry vent(s) (4400), and one or more of any air duct(s) (4455) that returns air (4520) and/or air/gas(s) exit vent(s) (4405). The one or more of any suitable and effective conduit(s), tube(s), hose(s) (40)(4380) and/or vent bypass system(s) (4415), can and without limitation, effectively directly and/or indirectly connect and communicate with the one or more of any air duct(s) (4515) and/or air/gas(s) entry vent(s) (4400) that supply air to one or more area(s) and room(s) (4410), to the one or more of any air duct(s) (4520) and/or air/gas(s) exit vent(s) (4405) that return air/gas(s) from these one or more area(s) and room(s) (4410) back to the HVAC part(s) and equipment(s) (4465) and/or HVAC unit(s) (4610), so that air/gas(s), deployed agent(s) (4510), and/or gas(s) can effectively pass from the air/gas(s) supply duct(s) (4515) and air/gas(s) entry vent(s) (4400), to the air/gas(s) exit vent(s) (4405) that connect to the said return ducts (4520) and eventually back to the HVAC part(s) and equipment(s) (4465) and/or HVAC unit(s) (4610). Without being limited, the air/gas(s) and/or deployed agent(s) can also move in the opposite direction(s). Also, and without being limited, one or more of any air supply duct(s) (4515) and air/gas(s) entry vent(s) (4400) in certain, unique, and/or specific area(s), zone(s), and/or room(s) (4410) can also be effectively connected to one or more of any air/gas exit vent(s) (4405) and air return ducts (4520) in other certain, unique, different, and/or specific area(s), zone(s), and/or room(s) (4410).

According to FIGS. 16-20 and FIG. 23, and without being limitation, one or more of any suitable and effective means and apparatus design(s) known to those skilled in the art, can be used to cover and/or seal any air/gas(s) vent(s) (4400) (4405) and/or orifice(s) (not shown), such as, but not limited to any suitable and effective, plate(s), cover(s), block(s), and/or vent cover door(s) (3930) (Herein called "Cover(s)" (4580)). The cover(s) (4580) can be effectively connected to, interfaced with, and/or include one or more of any suitable and effective means known to those skilled in the art, to directly, indirectly, and/or removably, connect with, one or more of any suitable and effective conduit(s), tube(s), and/or hose(s) (40)(4380), so that any, air, gas(s), and/or any deployed agent(s) (4510), may effectively flow to and/or from the various air duct(s) (4455)(4515)(4520), air/gas(s) vent(s) (4400)(4405), and/or other orifice(s) (not shown), through the one or more of any cover(s) (4580), as well as through the one or more of any connected conduit(s), tube(s), and/or hose(s) (40)(4380), and more preferably through various vent bypass system(s) (4415), that are all directly and/or indirectly connected to one another and/or communicate with one another through the various said conduits and/or hose(s) (40) (4380). It is preferred, without limitation, that these various part(s) and component(s) are removably and effectively sealed to one another in a manner known to those skilled in the art, and additionally at least one effective seal(s) (not shown) can also be effectively positioned between the various air duct(s) (4455)(4515)(4520) and/or air/gas(s) vent(s) (4400) (4405), and the various cover(s) (4580).

According to FIGS. 16-21 and FIG. 23, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s) (not shown), air return ducts (4520), cover(s) (4580), and/or various HVAC part(s) and equipment(s) (4465) and/or HVAC unit(s) (4610), can be connected and/or interconnected in various ways known to those skilled in the art, for activities such as, but not limited to, loosening the contamination(s), collecting the contaminant(s), and treating the surfaces, of the various, conduit(s), air duct(s), and HVAC part(s) and equipment(s) (4465) and/or HVAC unit(s) (4610).

Figure 16:
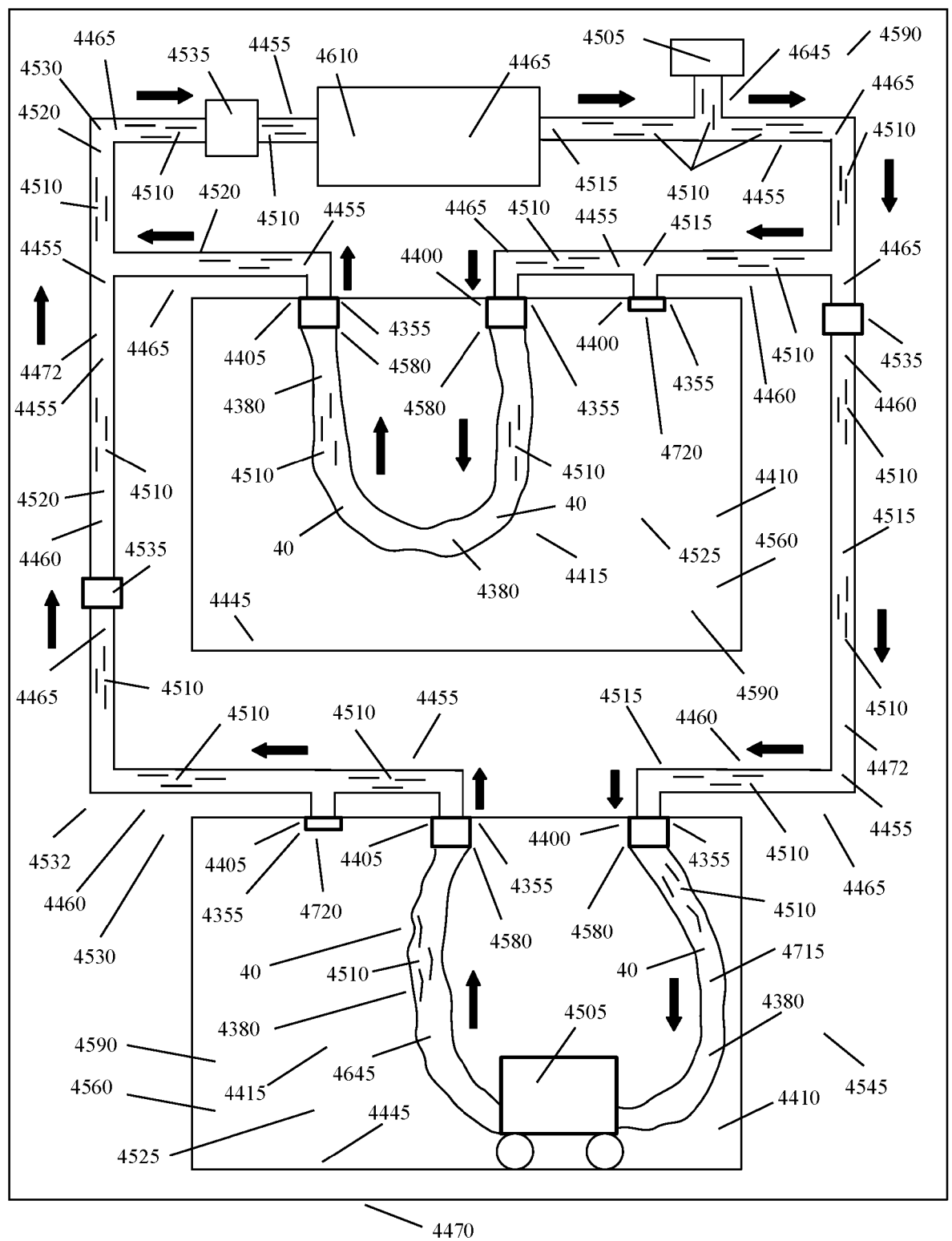
Figure 17:
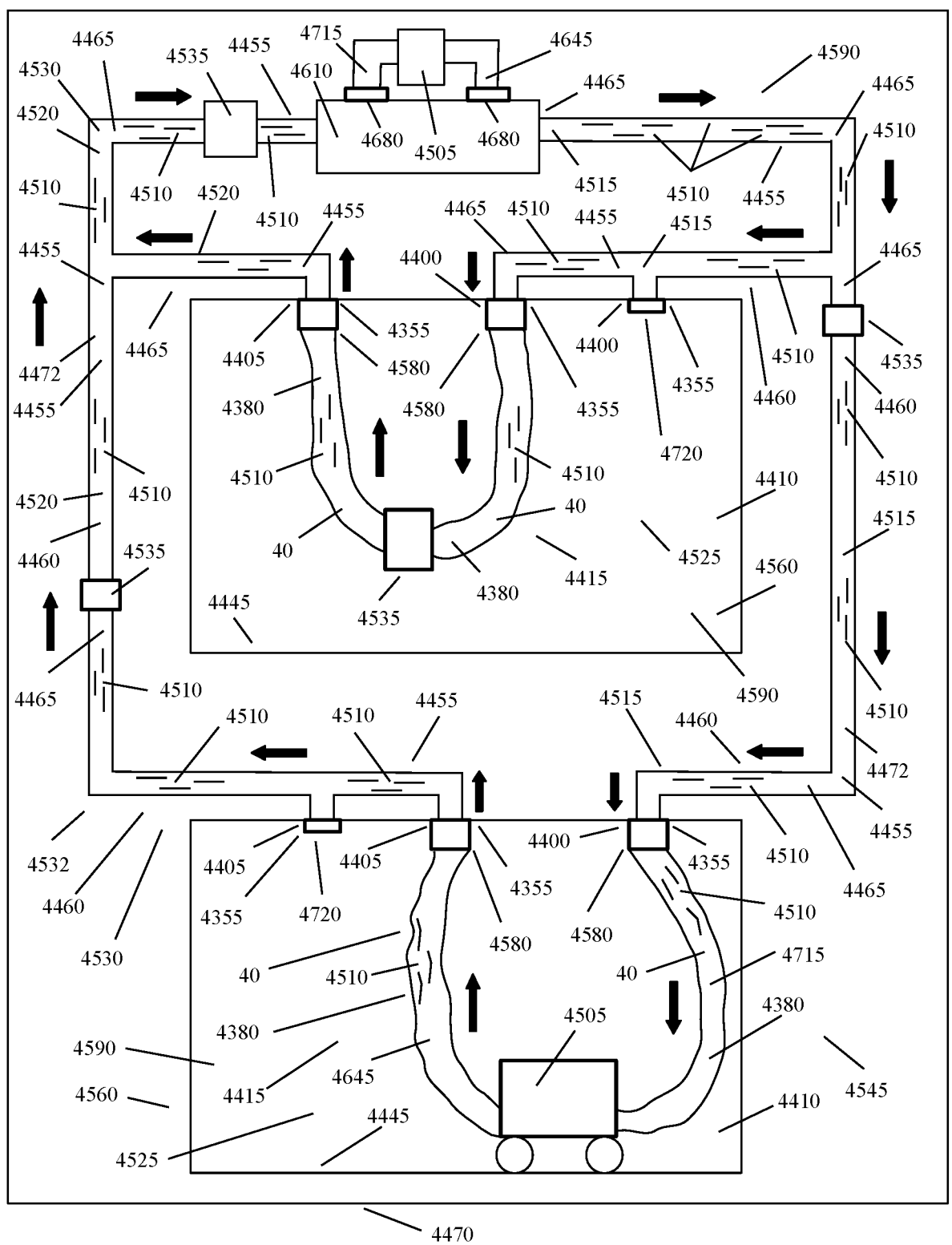

In one configuration, and according to FIGS. 16-17, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, to form one or more of any effective sealed air/gas flow system(s) (4530), can be effectively connected and/or interconnected with one or more equipment(s) such as, but not limited to any, agent dispenser(s) (4505) and/or duct fan(s) (4535), so that the air/gas(s) and/or deployed agent(s) (4510) that are deployed into the connected conduits can circulate and/or fully circulate through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), various HVAC part(s) and equipment(s) (4465) and/or HVAC unit(s) (4610), and/or sealed air/gas flow system(s) (4530).

Figure 18:
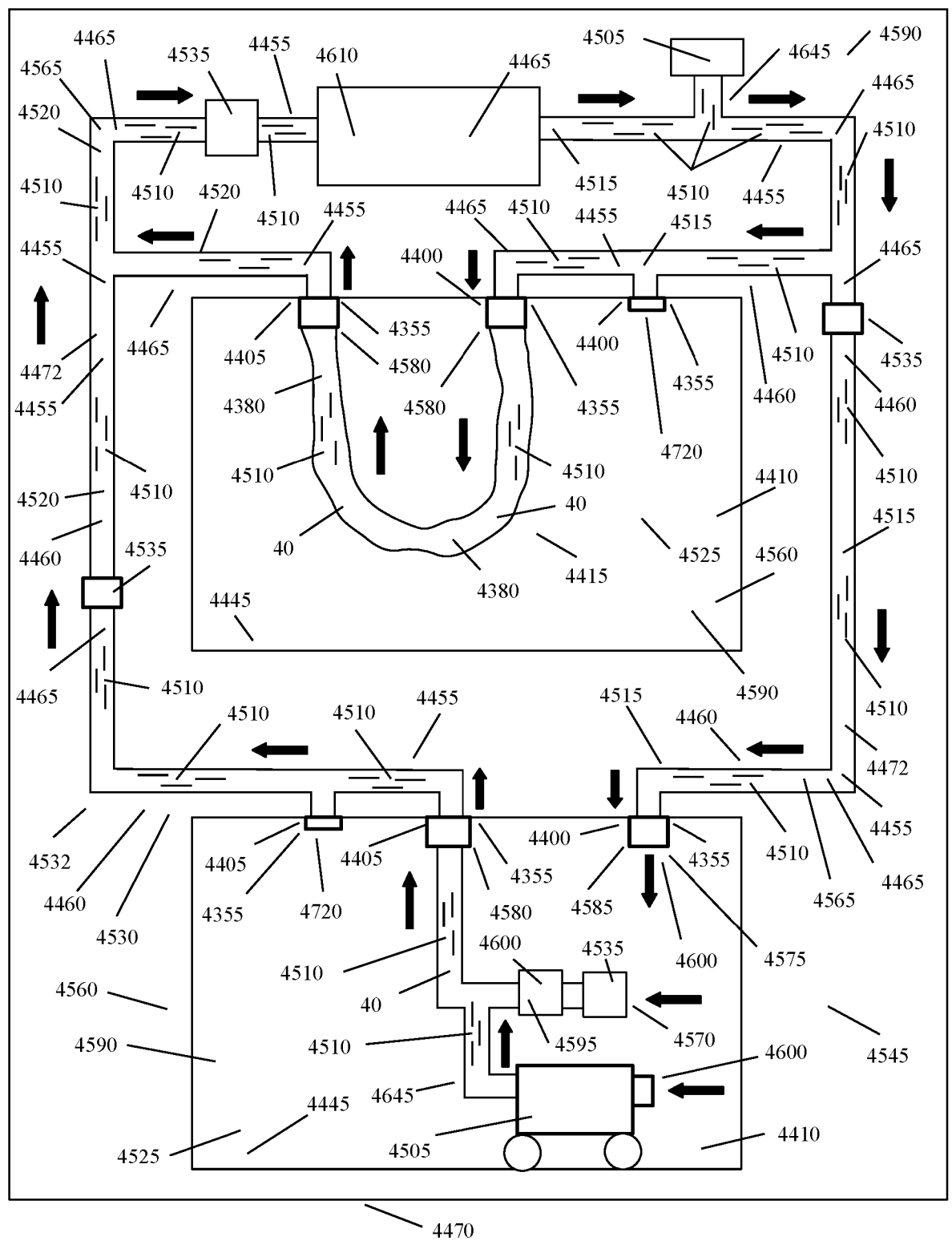

In another configuration, and according to FIG. 18, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, to form one or more of any effective sealed air/gas flow system(s) (4530), can be effectively connected and/or interconnected with one or more equipment(s) such as, but not limited to any, agent dispenser(s) (4505), air/gas(s) entry filter(s) (4595), duct fan(s) (4535), and/or air/gas exit filter(s) (4585), so that the air/gas(s) and/or deployed agent(s) (4510) that are deployed into the connected conduits can flow effectively through all of the various connected and/or interconnected part(s), space(s), area(s), and/or component(s) such as, but not limited to any, air duct(s) (4455), air supply duct(s) (4515), air/gas(s) entry vent(s) (4400), hose(s) (40)(4380), vent bypass system(s) (4415), air/gas exit vent(s) (4405), air return ducts (4520), various HVAC part(s) and equipment(s) (4465) and/or HVAC unit(s) (4610), and/or sealed air/gas flow system(s) (4530), and then flow through one or more air/gas exit filter(s) (4585) and exit into the surrounding environment (4590). Without being limited, the surrounding environment (4590) can include, but is not limited to any, area(s), space(s), room(s) (4410), atmosphere(s), that is not connected to any, and/or is outside of any connected, sealed, and/or communicating, system of various part(s), component(s), area(s), and/or space(s) such as, but not limited to any, air duct(s) (4455), air supply duct(s) (4515), air/gas(s) entry vent(s) (4400), hose(s) (40) (4380), vent bypass system(s) (4415), air/gas exit vent(s) (4405), air return ducts (4520), various HVAC part(s) and equipment(s) (4465) and/or HVAC unit(s) (4610), air duct system(s) (4460), sealed air/gas flow system(s) (4530), sealed zone(s) (4532), and/or open system(s) (4565).

Figure 19:
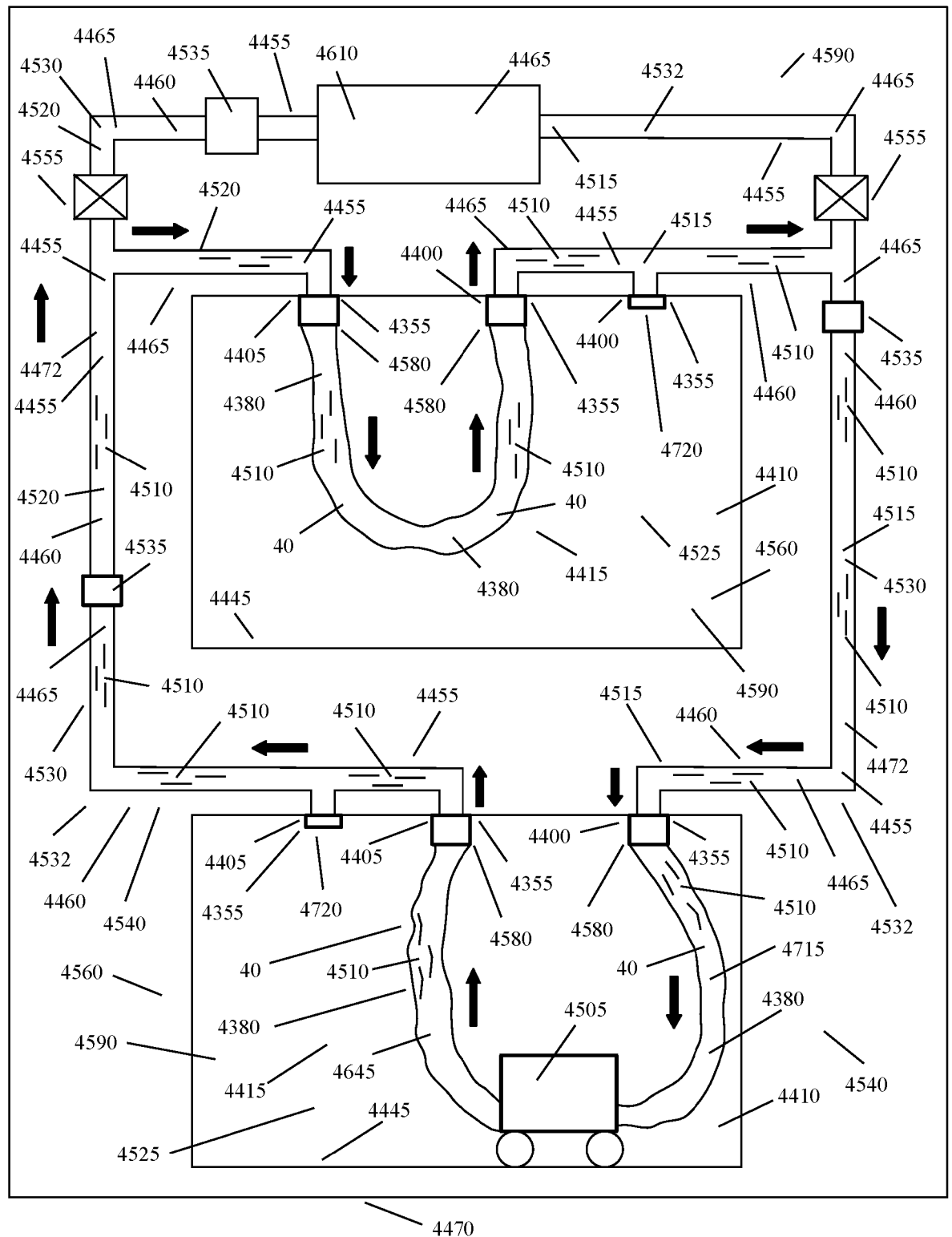

In still another configuration, and according to FIG. 19, and without limitation, the various air duct(s) (4455), air supply duct(s) (4515), air/gas(s) entry vent(s) (4400), hose(s) (40) (4380), air/gas exit vent(s) (4405), vent bypass system(s) (4415), orifice(s), air return ducts (4520), and/or various HVAC part(s) and equipment(s) (4465) and/or HVAC unit(s) (4610), that are connected and/or interconnected, and form one or more of any effective sealed zone(s) (4532), can be effectively connected and/or interconnected with one or more equipment(s) such as, but not limited to any, agent dispenser(s) (4505), and/or duct fan(s) (4535), so that the air/gas(s) and/or deployed agent(s) (4510) that are deployed into the connected conduits can circulate and/or fully circulate through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), various HVAC part(s)

and equipment(s) (4465) and/or HVAC unit(s) (4610), and/or sealed air/gas flow system(s) (4530).

Figure 20:
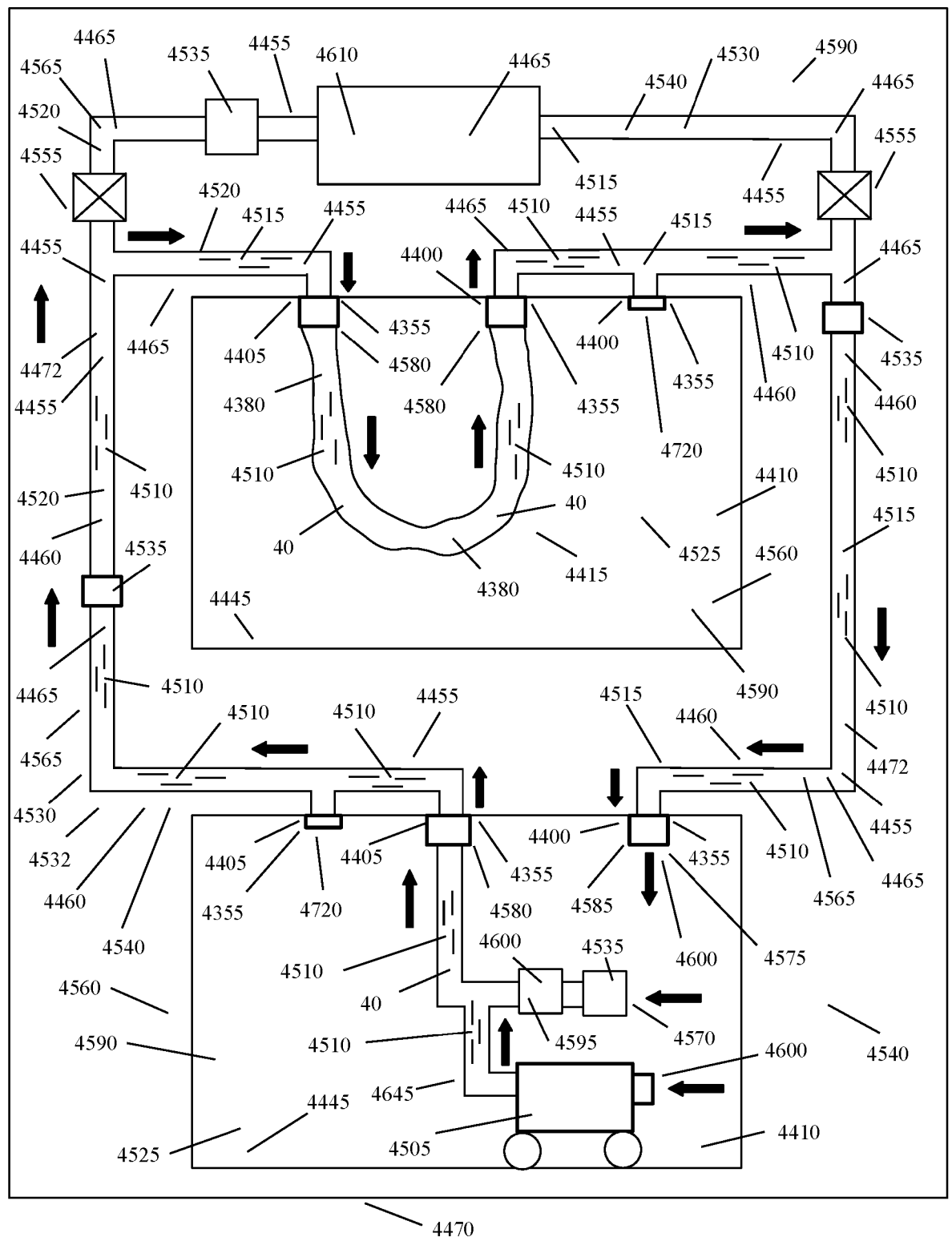

In still another additional configuration, and according to FIG. 20, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, and form one or more of any effective sealed zone(s) (4532), can be effectively connected and/or interconnected with one or more equipment(s) such as, but not limited to any, agent dispenser(s) (4505), duct fan(s) (4535), and/or air/gas exit filter(s) (4585), so that the air/gas(s) and/or deployed agent(s) (4510) that are deployed into the connected conduits can flow effectively through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), various HVAC part(s) and equipment(s) (4465), and/or sealed air/gas flow system(s) (4530), and then flow through one or more air/gas(s) exit filter(s) (4585) and exit into the surrounding environment (4590).

With reference to FIGS. 18 and 20, and without being limited, any air/gas(s) and/or deployed agent(s) (4510) that enters and/or exits the one or more sealed air/gas flow system(s) (4530) and/or sealed zone(s) (4532), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), HVAC part(s) and equipment(s) (4465) and/or HVAC unit(s) (4610), and/or sealed air/gas flow system(s) (4530), and then flow through one or more air/gas(s) exit filter(s) (4585), and/or sealed zone(s) (4532), and then exit into the surrounding environment (4590) through one or more of any effective exit filter(s) (4585) that can be any suitable and effective filters such as, but not limited to any, HEPA filter(s), ULPA filter(s), and/or any vapor capture filter(s), as known to those skilled in the art, before the air/gas(s) and/or deployed agent(s) (4510) exits into the surrounding environment (4590), preferably, and without limitation, after the time for administering, distributing, flowing, delivering, dispersing, and/or transmitting the deployed agent(s) has finished. Without being limited, it is preferred that only the external air/gas(s) that is used, provided, and/or flowed, is effectively and suitably filtered, and more preferably by one or more of any suitable and effective entry filter(s) (4595), before the said external air/gas(s) is introduced, injected, and/or flowed, into the one or more of any connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), air duct system(s) (4460), sealed air/gas flow system(s) (4530), and/or sealed zone(s) (4532). Without being limited, external air/gas(s) can be sourced from one or more of any suitable and effective location(s) such as, but not limited to those in the surrounding environment(s) (4590) outside of the said connected and/or interconnected part(s), space(s), area(s), and/or component(s).

Alternatively, and with reference to FIGS. 16-24, and without limitation, the various, part(s), component(s), area(s), and/or space(s) such as, but not limited to any, air duct(s) (4455), air supply duct(s) (4515), air/gas(s) entry vent(s) (4400), hose(s) (40)(4380), vent bypass system(s) (4415), air/gas exit vent(s) (4405), air return ducts (4520), various HVAC part(s) and equipment(s) (4465) and/or HVAC unit(s) (4610), air duct system(s) (4460), sealed air/gas flow system(s) (4530), open system(s) (4565), and/or sealed zone(s) (4532), can also be subjected to and/or undergo the one or more of any of the said step(s) and/or activities such as, but not limited to, "Loosening the Contamination(s)", "Collecting the Contaminant(s)", and/or "Treating the Surfaces", either with and/or without the use of the one or more of any suitable and effective filter(s) (4600)(4595)(4585) at one or more of any suitable and effective location(s). For example, and without limitation, during the activity of "Treating the Surfaces", the deployed agent(s) (4510) can be effectively circulated through and/or around the said various, part(s), component(s), area(s), and/or space(s), as well as any, air duct system(s) (4460), sealed air/gas flow system(s) (4530), and/or sealed zone(s) (4532), without the use of any air/gas(s) filter(s) (4600)(4595) (4585).

With reference to FIGS. 16-18, and without limitation, an apparatus and method of another embodiment of the present invention comprises numerous steps to mechanically clean and/or treat with one or more of any deployed agent(s) (4510), the one or more of any area(s), surface(s), and/or space(s), on, inside of, and/or within one or more of any, air duct(s) (4455), air supply duct(s) (4515), air/gas(s) entry vent(s) (4400), air/gas exit vent(s) (4405), hose(s) (40) (4380), vent bypass system(s) (4415), orifice(s), air return ducts (4520), air shaft(s) (4472), room(s) (4410), and various HVAC part(s) and equipment(s) (4465) and/or HVAC unit(s) (4610), open system(s) (4565), sealed air/gas flow system(s) (4530), and/or air duct system(s) (4460). These one or more steps can be, without limitation, taken in any number of any suitable and effective order(s) and/or combination(s), and one or more of these steps and/or one or more of any part(s) of these steps can also be omitted and/or modified, all in a manner known to those skilled in the art. These various steps and/or activities can also, and without limitation, take place at one or more of any suitable and effective locations, and at one or more of any suitable and effective time(s) and for any suitable and effective duration(s).

In a first step, and without being limited, the desired, needed, and/or relevant, air/gas(s) entry vent(s) (4400) and air/gas exit vent(s) (4405) and/or any other orifice(s), that can cause any unwanted leaks of any air/gas(s) and/or deployed agent(s), and that connect and/or communicate with any air duct(s) (4455) and/or any other part(s), space(s), and/or component(s), that communicate with any air duct(s) (4455), are effectively sealed in a manner known to those skilled in the art, and one or more of any suitable and effective hose(s) (40)(4380) of effective length and diameter, are used to suitably and effectively connect in a manner known to those skilled in the art, the one or more of any air/gas(s) entry vent(s) (4400) to the one or more of any suitable and effective air/gas exit vent(s) (4405), and preferably and without limitation, with one or more of any various suitable vent bypass system(s) (4415), so that the various air supply duct(s) (4515) can effectively communicate with the various air return duct(s) (4520), and/or various HVAC part(s) and equipment(s) (4465) and/or HVAC unit(s) (4610), to form any effective, open system(s) (4565), sealed air/gas flow system(s) (4530), and/or air duct system(s) (4460), so that air/gas(s) and/or deployed agent(s) (4510) can be effectively flowed, moved, and/or circulated, through and/or around, these various part(s), component(s), structure(s), conduit(s), space(s), area(s), hose(s) (40) (4380), air duct(s) (4455), and/or various HVAC part(s) and equipment(s) (4465) and/or HVAC unit(s) (4610).

In a second step, and without being limited, one or more of any suitable and effective air filter(s) (4600)(4595)(4585) such as, but not limited to any, HEPA filter(s) and/or ULPA filter(s), can also be optionally located and/or used if needed and as determined by those skilled in the art, at any suitable and effective time(s), but preferably and without limitation, before, during, and/or after, and more preferably and without limitation, before, any deployed agent(s) (4510) are administered, distributed, flowed, delivered, dispersed, and/or transmitted, by one or more of any agent dispenser(s) (4505), into the one or more of any, air duct system(s) (4460), sealed air/gas flow system(s) (4530) and/or open system(s) (4565).

Without being limited, the one or more air filter(s) (4600) (4595)(4585), can be optionally located at any suitable and effective location(s), including, but not limited to, suitably and effectively sealed inside any, air duct(s) (4455), hose(s) (40)(4380), conduit(s), and/or vent bypass system(s) (4415). Without being limited, at least one air filter(s) (4600) can be effectively and suitably located either and/or both where any air/gas(s) and/or fresh air/gas(s) might enter (4595) and/or exit (4585) any, open system(s) (4565), sealed air/gas flow system(s) (4530), and/or air duct system(s) (4460), so that any air/gas(s) and/or deployed agent(s) (4510) that might enter and/or exit the connected conduit(s) system(s) (4460) and/or the one or more open system(s) (4530), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), air duct system(s) (4460), open system(s) (4565), sealed air/gas flow system(s) (4530), and/or air duct system(s) (4460), and then optionally flow through one or more of any suitable air/gas(s) exit filter(s) (4585), and then exit into the surrounding environment (4590).

It is preferred, without limitation, that before any air/gas(s) exits into the surrounding environment (4590), the said air/gas(s) can also pass through one or more of any effective exit filter(s) (4585) that can be any suitable and effective filters such as, but not limited to any, HEPA filter(s), gas(s)/vapor(s) absorbing filter(s), and/or any gas(s)/vapor(s) capture filter(s), as known to those skilled in the art, before the air/gas(s) and/or deployed agent(s) (4510) exits the, open system(s) (4565), sealed air/gas flow system(s) (4530), and/or air duct system(s) (4460), into the surrounding environment (4590). It is more preferred, without limitation the said filter(s) (4600) (4595)(4585) are at least used during the time for administering, distributing, flowing, delivering, dispersing, and/or transmitting, the deployed agent(s) (4510) and/or during any time(s) where air/gas(s) are flowed through any air duct(s) 4455) and/or HVAC part(s) and equipment(s) (4465) and/or HVAC unit(s) (4610), for drying any of the treated surfaces.

In a third step, and without being limited, various vent bypass system(s) (4415), conduit(s), and/or hose(s) (40) (4380), are effectively directly and/or indirectly interfaced with the various air/gas(s) supply duct(s) (4515) and/or air/gas(s) entry vent(s) (4400) and air/gas exit vent(s) (4405) and/or air/gas(s) return duct(s) (4520), in one or more of any area(s) and/or room(s), allowing the said air/gas(s) entry vent(s) (4400) and/or air supply duct(s) (4515) and the air/gas exit vent(s) (4405) and/or air return duct(s) (4520) to effectively communicate, where the air/gas(s) that typically flows from the one or more air/gas(s) supply ducts into various room(s) and/or area(s) (4410), instead flows through the one or more hose(s) (40)(4380) and into the one or more connected air/gas(s) exit vent(s) (4405) and/or air/gas(s) return duct(s) (4520), and preferably and without limitation, flows, circulates, moves, either through, throughout, and/or around, any, open system(s) (4565), sealed air/gas flow system(s) (4530), and/or air duct system(s) (4460), and even more preferably and without limitation, flows, circulates, and/or moves, back to and/or through, the HVAC part(s) and equipment(s) (4465) and/or HVAC unit(s) (4610).

In a fourth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), can be mechanically cleaned by taking the step and/or undergoing the activity of "Loosening the Contamination(s)", whereby various means and methods known to those skilled in the art such as, but not limited to, mechanically scrubbing, air whipping, air washing, air brushing, hitting surface(s) with compressed air from one or more air nozzle(s), agitating, brushing, and/or wiping, the various targeted surface(s) of these various parts, space(s), and/or area(s), for one or more of any effective time(s), to remove any foreign object debris, pathogen(s), contaminant(s), and/or residue(s) that may have accumulated within, inside of, and/or on, these various part(s), component(s), structure(s), conduit(s), space(s), area(s), air duct(s) (4455), and/or various HVAC part(s) and equipment(s) (4465) and/or HVAC unit(s) (4610).

In a fifth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), can be further cleaned by various means and methods known to those skilled in the art such as, but not limited to any, vacuuming activity, pulling a vacuum through, and/or blowing air/gas(s) through, these said various part(s), component(s), structure(s), conduit(s), space(s), hose(s) (40) (4380), area(s), air duct(s) (4455), and/or various HVAC part(s) and equipment(s) (4465) and/or HVAC unit(s) (4610), at one or more of any effective time(s) and for any suitable and effective duration of time(s), by taking the step and/or undergoing the activity of "Collecting the Contaminant(s)", whereby one or more of any suitable and effective, tool(s), apparatus(s), pressure(s), vacuum(s), air velocity(s), air speed(s), and/or volume(s), of air and/or gas(s), may be used to remove any, foreign object debris, pathogen(s), particle(s), and/or residue(s), that may have accumulated within, inside of, and/or on, these said various, part(s), component(s), structure(s), conduit(s), hose(s), space(s), area(s), air duct(s) (4455), and/or various HVAC part(s) and equipment(s) (4465) and/or HVAC unit(s) (4610), all in a manner known to those skilled in the art.

Without being limited, at least the second step and the third step can also be combined in a manner known to those skilled in the art.

In a sixth step, and without being limited, one or more of any deployed agent(s) (4510) such as, but not limited to any, substance(s), agent(s), chemical(s), chemistry(s), and/or molecule(s), that includes, but is not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), can be administered, distributed, flowed, delivered, dispersed, and/or transmitted, by one or more of any agent dispenser(s) (4505), to clean, sanitize, disinfect, sterilize, and/or decontaminate, the one or more of any area(s), surface(s), and/or space(s), on and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460). This is further described in the step and/or activity called "Treating the Surfaces" mentioned earlier in the present invention. It is preferred, without limitation, that this fourth step is performed after the first, second, and third steps are effectively completed.

In a seventh step, and without being limited, after the said deployed agent(s) (4510) are finished being administered, distributed, flowed, delivered, dispersed, and/or transmitted, by one or more of any agent dispenser(s) (4505), the air/gas(s) within the one or more of any, open system(s) (4565), sealed air/gas flow system(s) (4530), and/or air duct system(s) (4460), can be suitably and effectively filtered at one or more of any suitable and effective, location(s), time(s), and duration of time(s), with one or more of any suitable and effective air/gas(s) filter(s) (4600)(4595)(4585), in any suitable and effective manner known to those skilled in the art. Also, without being limited, the one or more of any air/gas(s) filter(s) (4600)(4595)(4585) can be suitably and effectively, located, located within, directly attached, indirectly attached, connected, temporarily connected, removably connected, sealed within, removably sealed within, to, with, at, and/or within, one or more of any suitable and effective location(s), part(s), component(s) and/or equipment(s), such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), various HVAC part(s) and equipment(s) (4465) and/or HVAC unit(s) (4610), the beginning of any air duct (4455) system, the end of any air duct (4455) system, and/or any filter(s) holding apparatus(s) (not shown), at any suitable and effective time(s). Without being limited, the one or more of any effective vapor(s) and/or gas(s) capturing and/or airborne chemical absorbing filter(s) (4600)(4595)(4585) known to those skilled in the art, can also be removably connected to the one or more of any hose(s) (40)(4380), at any effective time(s), but preferably at least after the deployed agent(s) (4510) are finished being administered, distributed, flowed, delivered, dispersed, and/or transmitted.

In an eighth step, and without being limited, after the said deployed agent(s) (4510) are finished being administered, distributed, flowed, delivered, dispersed, and/or transmitted, by one or more of any agent dispenser(s) (4505), any suitable and effective air/gas(s), and more preferably and without limitation, any, effectively filtered, fresh, and/or pure, air/gas(s) that is effectively "dry" in a manner known to those skilled in the art, can be flowed through and/or over any, space(s), area(s), part(s), conduit(s), and/or component(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), to effectively dry the various treated surfaces on and/or within these said one or more of any, area(s), surface(s), part(s), conduit(s), component(s) and/or space(s). The flow of the said air/gas(s) can be provided by means such as, but not limited to, either pulling a vacuum through, and/or blowing, flowing, and/or moving, air/gas(s) through and/or over, these said area(s), surface(s), part(s), conduit(s), component(s) and/or space(s), at one or more of any effective time(s) and for any suitable and effective duration of time(s), using any suitable and effective, pressure(s), vacuum(s), air velocity(s), air speed(s), and/or volume(s), of air and/or gas(s).

With reference to FIGS. 19-21, and without limitation, an apparatus and method of another embodiment of the present invention comprises numerous steps to mechanically clean and/or treat with one or more of any deployed agent(s) (4510), the one or more of any area(s), surface(s), and/or space(s), on, inside of, and/or within any, air duct(s) (4455), air supply duct(s) (4515), HVAC part(s) and equipment(s) (4465) and/or HVAC unit(s) (4610), area(s), zone(s), area(s) of air duct(s) (4455), zone(s) of air duct(s) (4455), room(s) (4410), air/gas(s) entry vent(s) (4400), air/gas exit vent(s) (4405), hose(s) (40)(4380), vent bypass system(s) (4415), orifice(s), and/or air return ducts (4520), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550). These one or more steps can be, without limitation, taken in any number of any suitable and effective order(s) and/or combination(s), and one or more of these steps and/or one or more of any part(s) of these steps can also be omitted and/or modified, all in a manner known to those skilled in the art. These various steps and/or activities can, and without limitation, take place at one or more of any suitable and effective location(s), and at one or more of any suitable and effective time(s) and for any suitable and effective duration(s).

In a first step, and without being limited, one or more of any relevant, desired, and/or needed, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), can be effectively isolated (Herein called "Sealed Zone(s)" (4532)) in any suitable and effective manner known to those skilled in the art, so that they cannot communicate with other, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that are not in the same and/or designated sealed zone(s) (4532). Without being limited, the one or more of any sealed zone(s) (4532) can be created by using one or more of any suitable and effective means known to those skilled in the art, to effectively block, seal, and/or seal off, one or more of any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), in one or more of any suitable and effective location(s), area(s), and/or zone(s), in order to create one or more of any suitable and effective sealed zone(s) (4532). The one or more of any sealed zone(s) (4532) can be, and without limitation, any, size(s), shape(s), number(s), complexity(s), system(s), and/or group(s), of any part(s) and component(s) such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520).

In a second step, and without being limited, the desired, needed, and/or relevant, air/gas(s) entry vent(s) (4400) and air/gas exit vent(s) (4405), and/or any other orifice(s) that can cause any unwanted leaks of any air/gas(s) and/or deployed agent(s), and that connect with any air duct(s) (4455) and/or any other part(s), space(s), and/or component(s), that communicate with any air duct(s) (4455) and connect and/or communicate with the sealed zone(s) (4532), are effectively sealed in a manner known to those skilled in the art, and one or more of any suitable and effective hose(s) (40)(4380) of effective length and diameter, are used to suitably and effectively connect in a manner known to those skilled in the art, the one or more of any air/gas(s) entry vent(s) (4400) to the one or more of any suitable and effective air/gas exit vent(s) (4405), and preferably and without limitation, with one or more of any suitable vent bypass system(s) (4415), so that the various air supply duct(s) (4515) can effectively communicate with the various air return duct(s) (4520), to form one or more of any sealed zone(s) (4532).

Without being limited, once the sealed zone(s) (4532) are formed, air/gas(s) and/or deployed agent(s) (4510) can be effectively flowed, moved, and/or circulated, through and/or around, the various part(s), component(s), structure(s), conduit(s), space(s), and/or area(s), that can form the one or more of any sealed zone(s) (4532) such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40) (4380), vent bypass system(s) (4415), orifice(s), and/or air return ducts (4520).

In a third step, and without being limited, one or more of any suitable and effective air filter(s) (4600)(4595)(4585) such as, but not limited to any, HEPA filter(s) and/or ULPA filter(s), can also be located and/or used at any suitable and effective time(s), but preferably and without limitation, before, during, and/or after, any deployed agent(s) (4510) are administered, distributed, flowed, delivered, dispersed, and/or transmitted, by one or more of any agent dispenser(s) (4505), into the one or more of any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and more preferably, and without limitation, after the deployed agent(s) (4510) are administered, distributed, flowed, delivered, dispersed, and/or transmitted.

Without being limited, the one or more air filter(s) (4600) (4595)(4585), can be optionally located at any suitable and effective location(s), including, but not limited to, suitably and effectively sealed inside any, air duct(s) (4455), hose(s) (40)(4380), and/or vent bypass system(s) (4415). It is preferred, without limitation, that at least one air filter(s) (4600) can be effectively and suitably located either and/or both where any air/gas(s) and/or fresh air/gas(s) enters (4595) and exits (4585) the sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), so that any air/gas(s) and/or deployed agent(s) (4510) that enters and/or exits the one or more sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and then flow through one or more air/gas(s) exit filter(s) (4585), and then exit into the surrounding environment (4590). It is preferred, without limitation, that before any air/gas(s) exits into the surrounding environment (4590), the said air/gas(s) can also pass through one or more of any effective exit filter(s) (4585) that can be any suitable and effective filters such as, but not limited to any, HEPA filter(s) gas(s)/vapor(s) absorbing filter(s), and/or any gas(s)/vapor(s) capture filter(s), as known to those skilled in the art, before the air/gas(s) and/or deployed agent(s) (4510) exits the sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and into the surrounding environment (4590). It is more preferred, without limitation, that the said filter(s) (4600)(4595)(4585) are at least used during the time for administering, distributing, flowing, delivering, dispersing, and/or transmitting, the deployed agent(s) (4510) into any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and/or during any time(s) where air/gas(s) are flowed through any air duct(s) (4455) and/or HVAC part(s) and equipment(s) (4465) and/or HVAC unit(s) (4610), for drying any of these treated surfaces.

In a fourth step, and without being limited, various vent bypass system(s) (4415), conduit(s), and/or hose(s) (40) (4380), are effectively directly and/or indirectly interfaced with the various air/gas(s) supply duct(s) (4515) and/or air/gas(s) entry vent(s) (4400) and air/gas exit vent(s) (4405) and/or air/gas(s) return duct(s) (4520), in one or more of any area(s) and/or room(s), allowing the said air/gas(s) entry vent(s) (4400) and/or air supply duct(s) (4515) and the air/gas exit vent(s) (4405) and/or air return duct(s) (4520) to effectively communicate, where the air/gas(s) that typically flows from the one or more air/gas(s) supply ducts into various room(s) and/or area(s) (4410), instead flows through the one or more hose(s) (40)(4380) and into the one or more connected air/gas(s) exit vent(s) (4405) and/or air/gas(s) return duct(s) (4520), and preferably and without limitation, flows, circulates, and/or moves, either through, throughout, and/or around, any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550).

In a fifth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can be mechanically cleaned by various means and methods known to those skilled in the art such as, but not limited to, mechanically scrubbing, air whipping, air washing, air brushing, hitting surface(s) with compressed air from one or more air nozzle(s), agitating, brushing, and/or wiping, the various targeted surface(s) of these various parts, space(s), and/or area(s), for one or more of any effective time(s), to remove any foreign object debris, pathogen(s), contaminant(s), and/or residue(s) that may have accumulated within, inside of, and/or on, these various part(s), component(s), structure(s), conduit(s), space(s), area(s), air duct(s) (4455), and/or various HVAC part(s) and equipment(s) (4465) and/or HVAC unit(s) (4610).

In a sixth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can then be further cleaned by various means and methods known to those skilled in the art such as, but not limited to any, vacuuming activity, pulling a vacuum through, and/or blowing air/gas(s) through, these various part(s), component(s), structure(s), conduit(s), space(s), hose(s) (40)(4380), area(s), air duct(s) (4455), and/or various HVAC part(s) and equipment(s) (4465) and/or HVAC unit(s) (4610), at one or more of any effective time(s) and for any suitable and effective duration of time(s), and with one or more of any suitable and effective, tool(s), apparatus(s), pressure(s), vacuum(s), air velocity(s), air speed(s), and/or volume(s) of air and/or gas(s), to remove any foreign object debris, pathogen(s), particle(s), and/or residue(s), that may have accumulated within, inside of, and/or on, these various part(s), component(s), structure(s), conduit(s), hose(s), space(s), area(s), air duct(s) (4455), and/or various HVAC part(s) and equipment(s) (4465) and/or HVAC unit(s) (4610), in a manner known to those skilled in the art. Without being limited, at least the second step and the third step can also be combined in a manner known to those skilled in the art.

In a seventh step, and without being limited, one or more of any deployed agent(s) (4510) such as, but not limited to any, substance(s), agent(s), chemical(s), chemistry(s), and/or molecule(s), that includes, but is not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), can be administered, distributed, flowed, delivered, dispersed, and/or transmitted, by one or more of any agent dispenser(s) (4505), to clean, sanitize, disinfect, sterilize, and/or decontaminate, the one or more of any area(s), surface(s), and/or space(s), on and/or within any, air duct(s) (4455), air supply duct(s) (4515), air/gas(s) entry vent(s) (4400), air/gas exit vent(s) (4405), hose(s) (40) (4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550). It is preferred, without limitation, that this fourth step is performed after the first, second, and third steps are effectively completed.

In an eighth step, and without being limited, after the said deployed agent(s) (4510) are finished being administered, distributed, flowed, delivered, dispersed, and/or transmitted, by one or more of any agent dispenser(s) (4505), the air/gas(s) within the one or more of any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can be suitably and effectively filtered at one or more of any suitable and effective, time(s), location(s), and duration of time(s), with one or more of any suitable and effective air/gas(s) filter(s) (4600)(4595)(4585), in any suitable and effective manner known to those skilled in the art. Also, without being limited, the one or more of any air/gas(s) filter(s) (4600)(4595)(4585) can be suitably and effectively, located, located within, directly attached, indirectly attached, connected, temporarily connected, removably connected, sealed within, removably sealed within, to, with, at, and/or within, one or more of any suitable and effective location(s), part(s), component(s) and/or equipment(s) such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), and various HVAC part(s) and equipment(s) (4465) and/or HVAC unit(s) (4610), including but not limited to any filter(s) holding apparatus(s) (not shown). Without being limited, the one or more of any effective vapor and/or gas(s) capturing and/or airborne chemical absorbing filter(s) (4600)(4595)(4585) known to those skilled in the art, can also be removably connected to the one or more of any hose(s) (40)(4380), after the deployed agent(s) (4510) are finished being administered, distributed, flowed, delivered, dispersed, and/or transmitted.

In a ninth step, and without being limited, after the said deployed agent(s) (4510) are finished being administered, distributed, flowed, delivered, dispersed, and/or transmitted, by one or more of any agent dispenser(s) (4505), any suitable and effective air/gas(s), and more preferably and without limitation, any, effectively filtered, fresh, and/or pure, air/gas(s) that is effectively "dry" in a manner known to those skilled in the art, can be flowed through and/or over any, space(s), area(s), part(s), conduit(s), and/or component(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), to effectively dry the various treated surfaces on and/or within these said one or more of any, area(s), part(s), conduit(s), component(s) and/or space(s). The flow of the said air/gas(s) can be provided by means such as, but not limited to, either pulling a vacuum through, and/or blowing, flowing, and/or moving air/gas(s) through and/or over, these said area(s), part(s), conduit(s), component(s) and/or space(s), at one or more of any effective time(s) and for any suitable and effective duration of time(s), using any suitable and effective, pressure(s), vacuum(s), air velocity(s), air speed(s), and/or volume(s), of air and/or gas(s).

With reference to FIG. 22, and FIGS. 24-27, and according to another embodiment, and without limitation, many agent dispenser(s) (4505) known to those skilled in the art, cannot provide and/or output one or more of any effective air/gas(s) flow(s) that can carry the deployed agent(s) (4510) various effective and/or needed distance(s) and/or height(s), and/or the air/gas(s) flow(s) that the said agent dispenser(s) (4505) can generate and/or provide does not have one or more effective attributes such as, but not limited to any effective, air/gas flow(s) output speed(s), air/gas(s) output(s) velocity(s) and/or air/gas flow volume(s) output(s) per unit of time, to effectively carry the deployed agent(s) (4510), through and/or to various part(s), component(s), structure(s), height(s), conduit(s), enclosure(s), space(s), room(s), and/or area(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) and compartment(s) (not shown), room(s) (4410), air shaft(s) (4472), air/gas(s) entry vent(s) (4400), air/gas exit vent(s) (4405), hose(s) (40) (4380), vent bypass system(s) (4415), orifice(s), air return ducts (4520), air duct system(s) (4460), sealed zone(s) (4532), sealed air/gas flow system(s) (4530), and/or open system(s) (4565), especially and without limitation, when these various part(s), component(s), structure(s), conduit(s), enclosure(s), space(s), and/or area(s), have one or more of any, long, horizontal, complex, geometrically complex, and/or vertical, runs of conduit(s) and/or air duct(s) (4455), as well as any size(s), shape(s), area(s), volume(s), dimension(s), design(s), construction(s), geometry(s), height(s), length(s), and/or system height(s).

Also, with reference to FIG. 22 and FIGS. 24-27, and without limitation, agent dispenser(s) (4505) known to those skilled in the art, need one or more of any means to suitably and/or effectively interface with various, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), chamber(s), room(s) (4410), air shaft(s) (4472), air/gas(s) entry vent(s) (4400), air/gas exit vent(s) (4405), hose(s) (40)(4380), vent bypass system(s) (4415), orifice(s), service and/or work compartment(s) (not shown), and/or air return ducts (4520), especially in a manner that is hermetically sealed. The present invention also provides a means to solve these said problems with the current art.

According to FIG. 22 and FIGS. 24-27, and without limitation, an apparatus and method is presented in the present invention. Without being limited, one or more of any, agent dispenser(s) (4505), suitable and effective part(s) of the said agent dispenser(s) (4505), and/or deployed agent generator(s) (4620), and known and/or unknown to those skilled in the art, can be effectively communicated with and/or connected to one or more of any suitable and effective location(s) of the one or more of any agent flow compartment(s) (booster chamber) (4630). The booster chamber (4630) accelerates the momentum of the deployed agent(s) (4510) into the return ducts (4520) with at least one fan or the like. Further, and without limitation, the deployed agent(s) (4510) can be aerosolized, vaporized, generated, and/or created, at one or more of any suitable and effective location(s) outside of the said agent flow compartment(s) (4630) by one or more of any suitable and effective means to, aerosolize, generate, heat, vaporize, translate, and/or create, the deployed agent(s) (4510) that is known and/or unknown to those skilled in the art (Herein called "Deployed Agent Generator(s)") (4620) such as, but not limited to any, ultrasonic aerosol generator(s), aerosol generator(s), gas(s) and/or vapor(s) generator(s), hydrogen peroxide gas(s)/vapor(s) generator(s), peroxyacetic acid (PAA) gas(s)/vapor(s) generator(s), ozone generator(s), chlorine dioxide gas(s)/vapor(s) generator(s), means to create vapor(s), aerosol(s), and/or gas(s) containing both hydrogen peroxide and ozone, aerosol(s) containing chlorine dioxide generator(s), aerosol(s) and/or vapor(s) generator(s) that disperse any chemical(s) and/or molecules that are effective at killing and/or neutralizing any bacteria(s), viruse(s), spore(s), bacteriophage(s), and/or fungus(s), and/or aerosol generator(s) that generates aerosol(s) using any compressed air/gas(s).

Without being limited, the one or more deployed agent generator(s) (4620) can directly and/or indirectly connect and communicate with the one or more agent flow compartment(s) (4630) using one or more of any suitable and effective, pipe(s), connection area(s) and/or space(s), conduit(s), duct(s), and/or hose(s) (Herein called "Deployed Agent Exhaust Pipe(s)") (4625). Without being limited, the deployed agent exhaust pipe(s) (4625) can also include and/or be replaced by, one or more of any suitable and effective part(s) of any aerosol extractor apparatus(s), and even more specifically one or more of any exhaust stack(s) and/or output conduit(s) or pipe(s) that are a part of and/or connect with the one or more of any aerosol extractor apparatus(s), as taught in U.S. Pat. No. 9,789,508. Also, and without being limited, the deployed agent exhaust pipe(s) (4625) can removably connect to the agent flow compartment(s) (4630) using one or more of any suitable and effective means known to those skilled in the art such as, but not limited to any, Tri-clamp adapter(s), and/or hose coupling(s) (Herein called "Coupling(s)") (4797). The deployed agent exhaust pipe(s) (4625) can be, and without limitation, any suitable and effective, length(s), flexibility(s), width(s), height(s), design(s), construction(s), geometry(s), and/or diameter(s), and they can be constructed from one or more of any suitable and effective material(s) known to those skilled in the art. It is preferred, without limitation, that the one or more deployed agent exhaust pipe(s) (4625) at least, terminate with, terminate into, terminate inside of, connect with, connect inside of, connect outside of, and/or communicate with, the agent flow compartment(s) (4630) in or with any suitable and effective manner, and at one or more of any suitable and effective location(s), so that the deployed agent(s) (4510) can be effectively moved, circulated, flowed, and/or blown, into the said agent flow compartment(s) (4630) from the deployed agent generator(s)" (4620). Also, and without being limited, the deployed agent generator(s)

(4620) can be located at one or more of any suitable and effective location(s) such as, but not limited to, outside of the agent flow compartment(s) (4630), inside of the agent flow compartment(s) (4630), outside of the agent dispenser(s) (4505), inside of the agent dispenser(s) (4505), as a part(s) of the agent dispenser(s) (4505), and/or partially inside of the agent flow compartment(s) (4630). It is preferred, without limitation, that the deployed agent generator(s) (4620) are suitably and effectively located outside of the agent flow compartment(s) (4630) and suitably inside of the agent dispenser(s) (4505).

The deployed agent(s) (4510) can be, and without limitation, moved, pulled, suctioned, vacuumed, circulated, flowed, and/or blown, from the deployed agent generator(s) (4620) into the agent flow compartment(s) (4630) using any suitable and effective means known to those skilled in the art such as, but not limited to one or more of any, suitable and effective source(s) of pressurized air/gas(s), air pump(s), blower(s), fan(s), and/or any other means to move any air/gas(s), (Herein called "Agent Generator Blower(s)") (4700) and at any suitable and effective, air/gas flow rates, cubic feet per minute, air/gas output speed(s), and/or air/gas flow volume output(s) per unit of time, to effectively carry the deployed agent(s) (4510), from the deployed agent generator(s) (4620) into the agent flow compartment(s) (4630). Any suitable and effective amount of deployed agent(s) (4510) can be moved into the agent flow compartment(s) (4630) from the deployed agent generator(s) (4620) per and/or for any suitable and effective unit(s) and/or length(s) of time(s), and at any suitable and effective time(s). It is preferred, without limitation, that the one or more deployed agent generator(s) (4620) are effectively connected to and communicate with one or more of any suitable and effective agent generator blower(s) (4700). Without being limited, the agent generator blower(s) (4700) can be effectively directly and/or indirectly connected to and communicate with one or more of any suitable and effective means to filter the air/gas(s) before and/or after the agent generator blower(s) (4700), such as, but not limited to any, HEPA filter(s) (Herein called "Airflow Injection Filter(s)") (4603). Without being limited, the one or more agent generator blower(s) (4700) can be located at one or more of an any suitable and effective location(s).

The said agent generator blower(s) (4700) can be, and without limitation, effectively directly and/or indirectly connected and/or removably connected to, and communicate with, one or more of any suitable and effective filter(s) (4603) or airflow injection filter(s) (4603), at one or more of any suitable and effective location(s), all in a manner known to those skilled in the art. It is preferred, without limitation, that air/gas(s) first enters the said one or more agent generator blower(s) (4700) before passing through the one or more airflow injection filter(s) (4603). However, and without limitation, air/gas(s) can also enter the agent generator blower(s) (4700) after passing through the one or more airflow injection filter(s) (4603). The air/gas(s) leaving the agent generator blower(s) (4700) and/or entering the deployed agent generator(s) (4620), can move and/or flow at any suitable and effective, flow rate(s), cubic feet per minute, speed(s), air/gas(s) flow output speed(s), air/gas(s) flow input speed(s), and/or air/gas(s) flow volume output(s) and/or input(s) per unit of time, into and through the deployed agent generator(s) (4620), agent flow compartment(s) (4630), and/or into any, area(s), room(s), air duct(s), compartment(s), and/or space(s) after passing through the agent flow compartment(s) (4630).

Referring to FIGS. 22 and 24, and without being limited, the one or more agent flow compartment(s) (4630) can also be located in one or more of any suitable and effective location(s) including, but not limited to, inside the agent dispenser(s) (4505), partially inside the agent dispenser(s) (4505), outside of and remote from the agent dispenser(s) (4505), and/or outside of the agent dispenser(s) (4505). It is preferred, without limitation, that the one or more agent flow compartment(s) (4630) are located suitably and effectively outside of the agent dispenser(s) (4505), but at least suitably and effectively attached and/or connected to the one or more agent dispenser(s) (4505) with which they communicate with. It is also preferred, without limitation, that the one or more agent flow compartment(s) (4630) are removably and suitably connected and/or attached to the one or more agent dispenser(s) (4505) with which they effectively communicate with.

Referring to FIG. 24, FIG. 25, and FIG. 27, and without limitation, the one or more of any agent flow compartment(s) (4630) can be located, connected and located, and/or separated and located, at one or more of any suitable and effective distance(s) from the one or more agent dispenser(s) (4505) and/or deployed agent generator(s) (4620). Without being limited, the at least one deployed agent generator(s) (4620) and/or deployed agent exhaust pipe(s) (4625) can removably connect to the agent flow compartment(s) (4630) using one or more of any suitable and effective chamber connection conduit(s) (4799). Without being limited, any suitable and effective means known to those skilled in the art can suitably and effectively removably connect the said chamber connection conduit(s) (4799) to the deployed agent generator(s) (4620) and/or deployed agent exhaust pipe(s) (4625), and the agent flow compartment(s) (4630), so that the one or more deployed agent generator(s) (4620) can effectively communicate with the one or more agent flow compartment(s) (4630).

Also, and without being limited, the chamber connection conduit(s) (4799) can removably connect to the deployed agent generator(s) (4620), deployed agent exhaust pipe(s) (4625), and/or the the agent flow compartment(s) (4630), using one or more of any suitable and effective means known to those skilled in the art such as, but not limited to any, Tri-clamp adapter(s), hose coupling(s), and/or any other suitable coupling(s) (4797) and related part(s) and component(s). The chamber connection conduit(s) (4799) can be, and without limitation, any suitable and effective, length(s), flexibility(s), width(s), height(s), design(s), and/or diameter(s), and they can be constructed from one or more of any suitable and effective material(s) known to those skilled in the art.

Without being limited, the deployed agent(s) (4510) can be, and without limitation, moved, circulated, flowed, and/or blown, from the agent flow compartment(s) (4630) and into any, location(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using any suitable and effective means known to those skilled in the art such as, but not limited to one or more of any, suitable and effective source(s) of pressurized air/gas(s), air pump(s), blower(s), fan(s), and/or any means to move any air/gas(s), (Herein called "Compartment Blower(s)") (4665) and at any suitable and effective, speed(s), volume(s) per unit of time(s), flow rate(s), air/gas(s) flow output speed(s), and/or air/gas(s) flow volume output(s) per unit of time, to effectively carry the deployed agent(s) (4510), out from the agent flow compartment(s) (4630). Any suitable and effective amount of deployed agent(s) (4510) can be moved out of the agent flow compartment(s) (4630) at and/or per any suitable and effective unit(s) of time(s). It is preferred, without limitation, that the agent flow compartment(s) (4630) are connected to and communicate with one or more of any suitable and effective compartment blower(s) (4665). Without being limited, the compartment blower(s) (4665) can be connected to and communicate with one or more of any suitable and effective means to filter the air/gas(s) before they enter the agent flow compartment(s) (4630) such as, but not limited to any, HEPA filter(s) (Herein called "Compartment Airflow Filter(s)") (4675). Without being limited, the agent flow compartment(s) (4630) can be connected to and communicate with one or more of any suitable and effective compartment airflow filter(s) (4675) that can be used to filter any air/gas(s) before they enter the agent flow compartment(s) (4630) after leaving the said compartment blower(s) (4665). It is preferred, without limitation, that any air/gas(s) that leaves the one or more compartment blower(s) (4665) are at least effectively filtered by at least one compartment airflow filter(s) (4675), located in one or more of any suitable and effective location(s), before the said air/gas(s) enters the said agent flow compartment(s) (4630).

Without being limited, one or more any suitable and effective compartment blower(s) (4665) and/or compartment airflow filter(s) (4675), can be located at one or more of an any suitable and effective location(s), and in one or more of any suitable and effective combination(s) and/or order(s), that communicates with the agent flow compartment(s) (4630). Also, and without being limited, one or more of any air/gas(s), flow(s), movement(s), source(s), and/or inlet(s), entering and/or into the agent flow compartment(s) (4630) can be suitably and effectively filtered and/or directly and/or indirectly connected to any suitable and effective filter(s), by one or more of any suitable and effective compartment airflow filter(s) (4675) at one or more of any suitable and effective location(s). Additionally, and without limitation, one or more of any suitable and effective compartment blower(s) (4665) can also be suitably and effectively located at one or more of any suitable and effective location(s) at and/or communicating with, one or more of any, outlet(s), orifice(s), exit(s), air/gas(s) outlet(s), and/or air/gas(s) exit orifice(s), that connect and/or communicate with the agent flow compartment(s) (4630), so that any suitable and effective, negative pressure(s), negative air/gas(s) pressure(s), negative atmospheric pressure(s), and/or vacuum(s), can be created and/or exerted by the said compartment blower(s) (4665) to pull, vacuum, move, and/or flow, any suitable and effective quantity of any air/gas(s) and/or deployed agent(s) (4510) out of, evacuated from, and/or through, the agent flow compartment(s) (4630) and/or the deployed agent generator(s) (4620), at any suitable and effective, time(s), flow rate(s), speed(s), and/or volume(s) per unit of time(s).

The agent flow compartment(s) (4630) can be, without limitation, directly and/or indirectly connected to and effectively communicate with one or more of any, location(s), room(s), chamber(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using one or more of any suitable and effective means known to those skilled in the art. Without being limited, the agent flow compartment(s) (4630) can removably connect and communicate with and/or have, one or more of any suitable and effective outlet(s) (Herein called "Agent Outlet(s)") (4670) through which the deployed agent(s) (4510) and/or any air/gas(s) can, flow, move, be blown, and/or be evacuated through and, out of the agent flow compartment(s) (4630).

It is preferred, without limitation, that the one or more agent outlet(s) (4670) and/or agent flow compartment(s) (4630), can connect and communicate with the said one or more of any, location(s), room(s), chamber(s), enclosure(s), space(s), part(s), component(s), structure(s), and/or conduit(s), with one or more of any suitable and effective, hose(s), pipe(s), and/or conduit(s) (Herein called "Connection Conduit(s)") (4645). Without being limited, the connection conduit(s) (4645) can be any suitable and effective, length(s), width(s), flexibility(s), design(s), height(s), and/or diameter(s), and they can be constructed from one or more of any suitable and effective material(s) known to those skilled in the art. Also, and without being limited, the one or more agent flow compartment(s) (4630) and/or agent outlet(s) (4670) can removably connect with and communicate with one or more of any suitable and effective connection conduit(s) (4645) using one or more of any suitable and effective means known to those skilled in the art such as, but not limited to any, Tri-clamp adapter(s), and/or hose coupling(s). It is preferred, without limitation, that the agent flow compartment(s) (4630) is directly and/or indirectly connected to and effectively communicates with one or more of any suitable and effective hose connector(s) (4640), and it is more preferred, without limitation, that the agent flow compartment(s) (4630) is directly and/or indirectly connected to and effectively communicates with one or more of any suitable and effective agent outlet(s) (4670) that can suitably and effectively connect with one or more hose connector(s) (4640), all in a manner known to those skilled in the art.

Also, without being limited, the connection conduit(s) (4645) can connect and communicate with the said any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), chamber(s) (not shown), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using one or more of any suitable and effective means known to those skilled in the art such as, but not limited to any, bulkhead fitting(s), and/or air/gas(s) pass-through fitting(s), that can be any suitable and effective, size(s), shape(s), geometry(s), length(s), width(s), design(s), and/or height(s), and can be removably attached at one or more of any suitable and effective location(s) (Herein called "Airflow Bulkhead Fitting(s)") (4680). Without being limited, the airflow bulkhead fitting(s) (4680) can be any suitable and effective, design(s), size(s), shape(s), geometry(s), diameter(s), length(s), width(s), and/or height(s), and can be any suitable and effective airflow bulkhead fitting(s) (4680) design(s) known to those skilled in the art. Without limitation, the said bulkhead fitting(s) (4680) can be designed and built so that they have one or more of any suitable and effective hole(s) and/or orifice(s) (not shown), that are any suitable and effective, size(s), shape(s), geometry(s), length(s), width(s), design(s), thickness(s), and/or height(s), but at least effectively sized and designed to allow any effective flow(s) of air/gas(s) and/or deployed agent(s) (4510) to flow from the one or more of any connection conduit(s) (4645) and into and through the one or more airflow bulkhead fitting(s) (4680), and into the said any, location(s), room(s), enclosure(s), space(s), part(s), component(s), structure(s), and/or conduit(s). Further, and without limitation, at least one side(s), halve(s), and/or part(s), of the bulkhead fitting(s) (4680), and as known to those skilled in the art, can removably connect with and communicate with one or more of any suitable and effective connection conduit(s) (4645) using one or more of any suitable and effective means known to those skilled in the art such as, but not limited to any suitable, Tri-clamp adapter(s), and/or hose coupling(s) (Herein called "Hose Connector(s)") (4640).

Also, and without being limited, one or more of any suitable and effective seal(s) and/or gasket(s) (Herein called "Gasket(s)") (4660) can be located at one or more of any suitable and effective location(s) between any suitable and effective part(s) of any airflow bulkhead fitting(s) (4680) and any suitable and effective parts of any wall(s) (4695). It is preferred, without limitation, that the said gasket(s) (4660) are included in the design of the said bulkhead fitting(s) (4680) and/or are a part of the design of the bulkhead fitting(s) (4680). Without limitation, the said gasket(s) (4660) can be designed and built so that they have one or more of any suitable and effective hole(s) and/or orifice(s) (not shown), that are any suitable and effective, size(s), shape(s), geometry(s), length(s), width(s), design(s), thickness(s), and/or height(s), but at least effectively sized and designed to allow any effective flow(s) of any air/gas(s) and/or deployed agent(s) (4510) to flow from the one or more of any connection conduit(s) (4645), through the one or more airflow bulkhead fitting(s) (4680), through the said gasket(s) (4660), and into the said one or more of any, location(s), room(s), enclosure(s), space(s), part(s), component(s), structure(s), and/or conduit(s). It is preferred, without limitation, that the one or more said hole(s) and/or orifice(s) (not shown) are located in and/or about the middle of the said gasket(s) (4660). It is also preferred, without limitation, that at least one of the said gasket(s) (4660) is located between one suitable part of any bulkhead fitting(s) (4680) known to those skilled in the art and one side of any wall(s) (4695), and another at least one of the said gasket(s) (4660) is located between another suitable part of any bulkhead fitting(s) (4680) known to those skilled in the art, and the other side of any wall(s) (4695), all in a manner known to those skilled in the art.

Without being limited, the deployed agent(s) (4510) can flow from at least the one or more agent flow compartment(s) (4630), preferably and without limitation through the one or more agent outlet(s) (4670) and/or air/gas(s) exhaust orifice(s) (4671), and then through the one or more connection conduit(s) (4645), where the deployed agent(s) (4510) can then flow through the one or more airflow bulkhead fitting(s) (4680) and any associated part(s), component(s), and gasket(s) (4660), including flowing through the one or more wall hole(s) (4690) and through the one or more hole(s)s and/or orifice(s) in the rear fitting plate(s) (Herein called "Rear Fitting Plate Orifice(s)") (4735), and into the said one or more of any, location(s), room(s), chamber(s), enclosure(s), space(s), part(s), component(s), structure(s), and/or conduit(s). Without being limited, the one or more wall hole(s) (4690) and rear fitting plate orifice(s) (4735) can be any suitable and effective, number(s), size(s), shape(s), diameter(s), length(s), width(s), depth(s), thickness(s), and/or design(s).

Without being limited, one or more of any suitable and effective, hole(s), opening(s), and/or orifice(s) (Herein called "Wall Hole(s)") (4690), of any suitable and effective, design(s), size(s), depth(s), shape(s), geometry(s), diameter(s), length(s), width(s), and/or height(s), can exist, can be made, can be penetrated through, and/or can be created in, on, and/or through, one or more of any, wall(s), barrier(s), structure(s), part(s), component(s), bulkhead wall(s), and/or partition(s) (Herein called "Wall(s)") (4695), of and/or belonging to, one or more of any, location(s), room(s), enclosure(s), chamber(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). Without being limited, the one or more of any airflow bulkhead fitting(s) (4680) can suitably and effectively, interface with, interact with, communicate with, cover, partially cover, fully cover, cover and communicate with, and/or connect with, the one or more of any wall hole(s) (4690). Also, and without being limited, the one or more wall hole(s) (4690) can, and without limitation, create one or more effective path(s) for any air/gas(s) and/or deployed agent(s) (4510) to flow from the one or more connection conduit(s) (4645), through the one or more airflow bulkhead fitting(s) (4680) and wall hole(s) (4690), and into the said one or more of any, location(s), room(s), chamber(s), enclosure(s), space(s), part(s), component(s), structure(s), and/or conduit(s).

Referring to FIGS. 22 and 24-27, and without limitation, air/gas(s) can be moved, supplied, and/or flowed, from one or more of any, location(s), room(s), chamber(s), enclosure(s), space(s), part(s), component(s), structure(s), and/or conduit(s), such as, but not limited to any, room(s) (4410), surrounding environment(s) (4705), air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), chamber(s) (not shown), air shaft(s) (4472), air/gas(s) entry vent(s) (4400), air/gas exit vent(s) (4405), hose(s) (40) (4380), vent bypass system(s) (4415), orifice(s), and/or air return ducts (4520), and can enter both the deployed agent generator(s) (4620) and the agent flow compartment(s) (4630) in any suitable and effective manner and having any suitable and effective attribute(s) including, but not limited to any, ratio of flow rate(s), ratio of flow speed(s), ratio of cubic feet per minute measurement(s), ratio of the airflow split between the deployed agent generator(s) (4620) and the agent flow compartment(s) (4630), flow rate(s), cubic feet per minute, speed(s), air/gas(s) flow output speed(s), air/gas(s) flow input speed(s), and/or air/gas(s) flow volume output(s) and/or input(s) per unit of time(s).

Also, and without being limited, the airflow that can be provided or flowed through one or more of any shared supply conduit(s) (5020) and into the one or more of any deployed agent generator(s) (4620) and agent flow compartment(s) (4630), can also enter both the deployed agent generator(s) (4620) and the agent flow compartment(s) (4630) in any suitable and effective manner and having any suitable and effective attribute(s) including, but not limited to any, ratio of flow rate(s), ratio of flow speed(s), ratio of cubic feet per minute measurement(s), ratio of the airflow split between the deployed agent generator(s) (4620) and the agent flow compartment(s) (4630), flow rate(s), cubic feet per minute, speed(s), air/gas(s) flow output speed(s), air/gas(s) flow input speed(s), and/or air/gas(s) flow volume output(s) and/or input(s) per unit of time.

It is preferred, without limitation, that any air/gas(s) that is supplied to at least the deployed agent generator(s) (4620), agent flow compartment(s) (4630), and the agent flow compartment(s) (4630) via the deployed agent generator(s) (4620), is at least effective, and it is more preferred, without limitation that the air/gas(s) that are supplied to at least the deployed agent generator(s) (4620), agent flow compartment(s) (4630), and the agent flow compartment(s) (4630) via the deployed agent generator(s) (4620), are effective, effectively set and established, set and established in any effective ratio, effectively established, and/or established and set in any effective balanced condition(s), for the effective and/or optimum deployment of the deployed agent(s) (4510) from the agent flow compartment(s) (4630) and/or agent dispenser(s) (4505).

With reference to FIG. 22 and FIGS. 24-27, and without limitation, various means or methods for flowing, moving, and/or supplying, air/gas(s) to the deployed agent generator(s) (4620) and the agent flow compartment(s) (4630) can be constructed and used, and certain examples are shown and described below. First, and with reference to FIG. 22, FIG. 24, and FIG. 27, and without limitation, air/gas(s) can be supplied, moved, and/or flowed, separately to the deployed agent generator(s) (4620) and the agent flow compartment(s) (4630), from within the one or more of any, location(s), room(s), chamber(s), enclosure(s), space(s), part(s), component(s), structure(s), and/or conduit(s), that the one or more agent dispenser(s) (4505) and/or agent flow compartment(s) (4630) are located at and/or within such as, but not limited to any, room(s) (4410), surrounding environment(s) (4705), enclosure(s) (not shown), chamber(s) (not shown), and outside of any chamber(s) (not shown).

Figure 25:
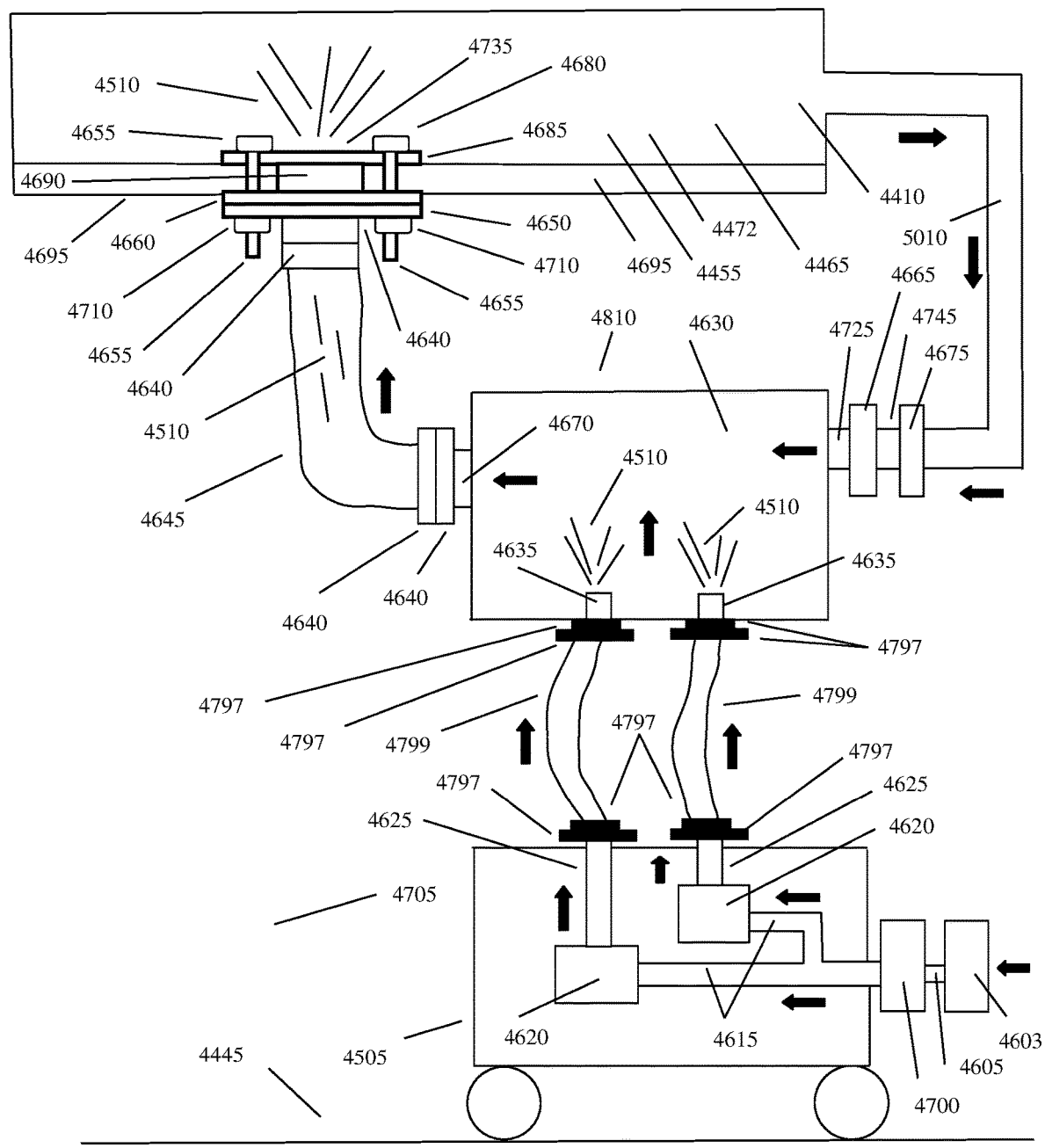

Second, and with reference to FIG. 25, and without limitation, air/gas(s) can be supplied, moved, and/or flowed, from the one or more of any, location(s), room(s), chamber(s), enclosure(s), space(s), part(s), component(s), structure(s), and/or conduit(s), such as, but not limited to any, room(s) (4410), air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), chamber(s) (not shown), air shaft(s) (4472), air/gas(s) entry vent(s) (4400), air/gas exit vent(s) (4405), hose(s) (40)(4380), vent bypass system(s) (4415), orifice(s), and/or air return ducts (4520), to the one or more agent flow compartment(s) (4630), by flowing the said air/gas(s) through one or more of any suitable and effective, pipe(s), hose(s), and/or conduit(s), herein called "Inlet supply Conduit(s)" (5010), that can directly and/or indirectly removably communicate with the one or more agent flow compartment(s) (4630). Without being limited, the inlet supply conduit(s) (5010) can be any suitable and effective, hose(s), pipe(s), and/or conduit(s), that can have any suitable and effective, construction, materials, flexibility, rigidness, and design, known to those skilled in the art, and can communicate with the agent flow compartment(s) (4630) and/or one or more of any suitable and effective part(s) and/or connector(s) that directly and/or indirectly communicate with the agent flow compartment(s) (4630), all in a manner known to those skilled in the art. Without being limited, air/gas(s) can also be supplied separately to the deployed agent generator(s) (4620) from one or more of any suitable and effective location(s) such as, but not limited to, within the one or more of any, location(s), room(s), enclosure(s), space(s), part(s), component(s), structure(s), and/or conduit(s), that the one or more agent dispenser(s) (4505), deployed agent generator(s) (4620), and/or agent flow compartment(s) (4630), are located at and/or within such as, but not limited to any, room(s) (4410), surrounding environment(s) (4705), enclosure(s) (not shown), chamber(s) (not shown), and outside of any chamber(s) (not shown). It is preferred, without being limited, that in this particular embodiment, the air/gas(s) that are supplied to the deployed agent generator(s) (4620) are not sourced from the same source of air/gas(s) that are supplied to the agent flow compartment(s) (4630), and the air/gas(s) that are supplied to the deployed agent generator(s) (4620) are from a separate and/or isolated environment and/or atmosphere from the air/gas(s) that are supplied to the agent flow compartment(s) (4630).

Figure 26:
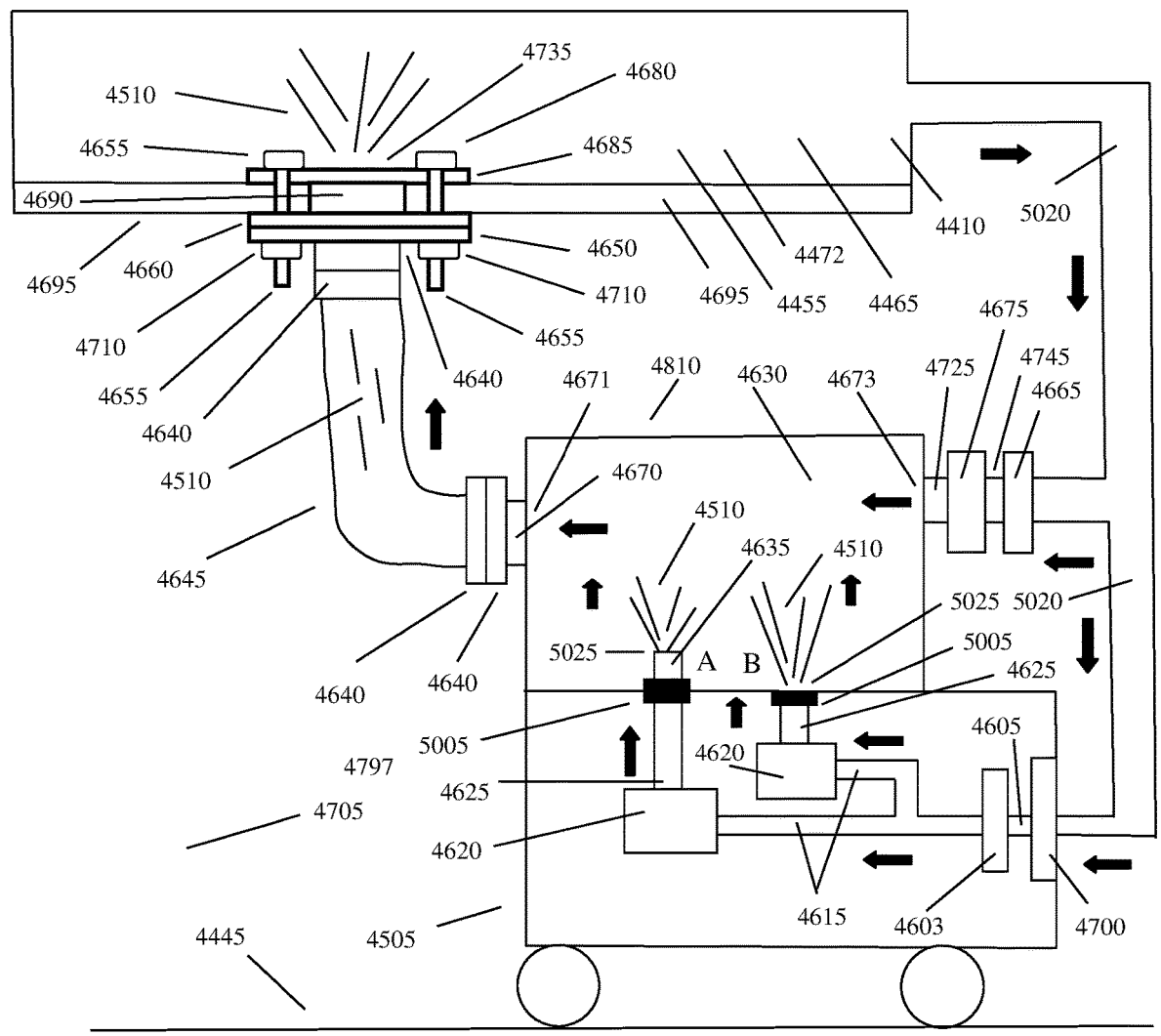

Third, and with reference to FIG. 26, and without limitation, air/gas(s) can be supplied, moved, and/or flowed, from the one or more of any, location(s), room(s), chamber(s), enclosure(s), space(s), part(s), component(s), structure(s), and/or conduit(s), such as, but not limited to any, room(s) (4410), air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), chamber(s) (not shown), air shaft(s) (4472), air/gas(s) entry vent(s) (4400), air/gas exit vent(s) (4405), hose(s) (40)(4380), vent bypass system(s) (4415), orifice(s), and/or air return ducts (4520), to both the one or more deployed agent generator(s) (4620) and the one or more agent flow compartment(s) (4630), by flowing the said air/gas(s) through one or more of any suitable and effective, pipe(s), hose(s), and/or conduit(s) (Herein called "Shared Supply Conduit(s)" (5020), that is a shared supply of the said air/gas(s) to both the one or more deployed agent generator(s) (4620) and the one or more agent flow compartment(s) (4630). Without being limited, the shared supply conduit(s)" (5020) can directly and/or indirectly removably communicate with both the one or more deployed agent generator(s) (4620) and the one or more agent flow compartment(s) (4630). Without being limited, the one or more shared supply conduit(s) (5020) can be any suitable and effective, hose(s), pipe(s), and/or conduit(s), that can have any suitable and effective, construction(s), dimension(s), length(s), width(s), height(s), diameter(s), material(s), flexibility(s), rigidness, and design(s), known to those skilled in the art, and can communicate with one or more of any suitable and effective part(s) that directly and/or indirectly communicates with the one or more deployed agent generator(s) (4620) and the one or more agent flow compartment(s) (4630) all in a manner known to those skilled in the art.

Referring to FIGS. 22 and 24-27, and without limitation, a more detailed description of an apparatus and method of the present invention is given. Without being limited, an improved agent dispenser(s) (4505) includes at least one agent flow compartment(s) (4630) that can be removably interfaced with, remotely connected to, be a part of, and/or be attached to, the said agent dispenser(s) (4505). The deployed agent(s) (4510) can be, and without limitation, generated in, by, and/or from, at least one deployed agent generator(s) (4620). Without being limited, the said deployed agent(s) (4510) can be flowed and/or moved out of the said deployed agent generator(s) (4620) and through one or more of any suitable and effective deployed agent exhaust pipe(s) (4625). Also without being limited, the said one or more deployed agent generator(s) (4620) and/or deployed agent exhaust pipe(s) (4625) can directly and/or indirectly communicate with the said agent flow compartment(s) (4630), where the said deployed agent(s) (4510) can preferably, and without limitation, flow and/or move into the said agent flow compartment(s) (4630) through and/or out of one or more of any suitable and effective flow outlet(s) (4635) that preferably, and without limitation, effectively communicates with and/or is directly and/or indirectly connected to, and/or is a part of, the said exhaust pipe(s) (4625). It is preferred, without limitation, that the one or more flow outlet(s) (4635) are suitably and effectively located inside of the agent flow compartment(s) (4630). Without being limited, the said exhaust pipe(s) (4625) can also terminate with one or more of the said flow outlet(s) (4635) that can face in one or more of any suitable and effective direction(s) and/or angle(s).

Alternatively, and without limitation, the one or more flow outlet(s) (4635) can connect and/or removably connect with one or more of any suitable and effective, Tri-clamp adapter(s), hose coupling(s), and/or any other suitable coupling(s) (4797) and related part(s) and component(s), all in a manner known to those skilled in the art. For example, and without limitation, the one or more flow outlet(s) (4635) can also extend any suitable and effective distance(s) outside of and/or beyond the agent flow compartment(s) (4630) and effectively connect and communicate with one or more suitable coupling(s) (4797), and the one or more output end(s) of the one or more deployed agent exhaust pipe(s) (4625) and/or deployed agent generator(s) (4620), can also effectively connect and communicate with one or more suitable coupling(s) (4797), so that one or more of any suitable chamber connection conduit(s) (4799) can removably connect with the input end of the said flow outlet(s) (4635) and the output end of the said deployed agent exhaust pipe(s) (4625) and/or deployed agent generator(s) (4620), and provide a means for the deployed agent generator(s) (4620) to effectively communicate with the agent flow compartment(s) (4630). Without being limited, the said flow outlet(s) (4635) can be any suitable and effective, size(s), shape(s), diameter(s), design(s), height(s), length(s), diameter(s), width(s), and/or number(s).

One or more of any suitable and effective blower(s), fan(s), air pump(s), or otherwise agent generator blower(s) (4700), can and without limitation, provide any effective flow(s) of air/gas(s) to effectively move, circulate, and/or flow, the deployed agent(s) (4510) out of and/or from the one or more deployed agent generator(s) (4620) and into the one or more agent flow compartment(s) (4630). The agent generator blower(s) (4700) can be, and without limitation, effectively and removably connected directly and/or indirectly to one or more of any effective filter(s) (4603) or air flow injection filter(s) (4603), all in a manner known to those skilled in the art. Air/gas(s), preferably and without limitation, from the environment surrounding the agent dispenser(s) (4505), can and without limitation, enter the said agent generator blower(s) (4700) after passing through one or more suitable conduit(s) or air flow inlet pipe(s) (4605) and before and/or after exiting the said air flow injection filter(s) (4603). Without being limited, the said fresh air/gas(s) can leave the said agent generator blower(s) (4700) and travels through one or more of any suitable conduit(s) or air flow supply pipe(s) (4615), where the said fresh air/gas(s) enters the one or more deployed agent generator(s) (4620). Without being limited, the one or more deployed agent(s) (4510) are created, formed, generated, vaporized, aerosolized, and/or turned into any gas(s), aerosol(s), and/or vapor(s), inside of and/or by, the one or more of any deployed agent generator(s) (4620), all in a manner known to those skilled in the art. The said air/gas(s) that is supplied to and/or into the deployed agent generator(s) (4620), flows, pushes, blows, moves, and/or circulates, the deployed agent(s) (4510) out of the said deployed agent generator(s) (4620) and directly and/or indirectly into the agent flow compartment(s) (4630). It is preferred, without limitation, that the said air/gas(s) that is supplied to and/or into the deployed agent generator(s) (4620), flows, pushes, blows, moves, and/or circulates, the deployed agent(s) (4510) out of the said deployed agent generator(s) (4620) and into the one or more suitable conduit(s) or deployed agent exhaust pipe(s) (4625) and then directly and/or indirectly into the agent flow compartment(s) (4630). The said one or more deployed agent exhaust pipe(s) (4625) directly and/or indirectly effectively communicates with one or more agent flow compartment(s) (4630) so that the said deployed agent(s) (4510) can effectively flow, move, and/or circulate, from the said deployed agent generator(s) (4620) and into the said agent flow compartment(s) (4630).

Without being limited, the agent flow compartment(s) (4630) can be any suitable and effective, size(s), shape(s), number(s), length(s), width(s), height(s), design(s), and/or geometry(s), and can include various design enhancements for effective air/gas(s) flow(s) and/or movement of air/gas(s), as well as any draining of any fluids, all in a manner known to those skilled in the art. Also, and without being limited, the agent flow compartment(s) (4630) can have one or more of any suitable and effective, outlet(s), exit orifice(s), exit(s), exhaust outlet(s), exhaust conduit(s), and/or hole(s) (Herein called "Agent Outlet(s)") (4670), through which air/gas(s) and the deployed agent(s) (4510) can exit the agent flow compartment(s) (4630). The agent outlet(s) (4670) can be any suitable and effective, size(s), shape(s), number(s), length(s), protrusion length(s), diameter(s), width(s), height(s), design(s), and/or geometry(s). Without being limited, the deployed agent(s) (4510) can flow from the one or more agent flow compartment(s) (4630), through the one or more agent outlet(s) (4670), and then into and through the one or more connection conduit(s) (4645). Without being limited, the deployed agent(s) (4510) can also flow from the one or more agent flow compartment(s) (4630), through the one or more agent outlet(s) (4670), and into the environment that surrounds the agent dispenser(s) (4505) and/or agent flow compartment(s) (4630). Alternatively, and without limitation, the deployed agent(s) (4510) can also flow from the one or more agent flow compartment(s) (4630), through the one or more agent outlet(s) (4670), through the one or more connection conduit(s) (4645), and then exit the said connection conduit(s) (4645) into the environment (4705) that surrounds the agent dispenser(s) (4505) and/or agent flow compartment(s) (4630). In another alternative, and without limitation, the deployed agent(s) (4510) can also flow from the one or more agent flow compartment(s) (4630), through the one or more agent outlet(s) (4670), through the one or more connection conduit(s) (4645) and then exit the said connection conduit(s) (4645) into the one or more of any, location(s), room(s), chamber(s), enclosure(s), space(s), part(s), component(s), structure(s), and/or conduit(s), such as, but not limited to any, room(s) (4410), air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), chamber(s) (not shown), air shaft(s) (4472), air/gas(s) entry vent(s) (4400), air/gas exit vent(s) (4405), hose(s) (40)(4380), vent bypass system(s) (4415), orifice(s), and/or air return ducts (4520), with which the said connection conduit(s) (4645) can directly and/or indirectly effectively communicate and/or connect with.

Without being limited, the said agent outlet(s) (4670) can directly and/or indirectly connect with one or more of any suitable and effective means, known to those skilled in the art, to suitably and effectively connect and/or removably connect, with one or more of any of the said connection conduit(s) (4645). It is preferred, without limitation, that the one or more agent flow compartment(s) (4630) have and/or communicate with one or more of any suitable and effective agent outlet(s) (4670) that suitably and effectively connects and communicates with one or more of the said hose connector(s) (4640), and the said hose connector(s) (4640) connects and communicates with one or more of the said connection conduit(s) (4645). It is also preferred, without limitation, that the said hose connector(s) (4640) are any suitable and effective, Tri-clamp adapter(s) and Tri-clamp connector(s) known to those skilled in the art.

One or more of any suitable and effective blower(s), fan(s), air pump(s), or otherwise compartment blower(s) (4665) can be, and without limitation, effectively and removably connected to the agent flow compartment(s) (4630) at one or more of any suitable and effective location(s). Also, without being limited, the said compartment blower(s) (4665) can provide an effective flow of any air/gas(s) into the one or more agent flow compartment(s) (4630) to effectively move, circulate, and/or flow, the deployed agent(s) (4510), that are flowed, moved, and/or circulated, into the said agent flow compartment(s) (4630) from the said deployed agent generator(s) (4620), out of the said agent flow compartment(s) (4630) and into one or more of any, location(s), room(s), chamber(s), enclosure(s), space(s), part(s), component(s), structure(s), and/or conduit(s), such as, but not limited to any, room(s) (4410), air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), chamber(s) (not shown), air shaft(s) (4472), air/gas(s) entry vent(s) (4400), air/gas exit vent(s) (4405), hose(s) (40)(4380), vent bypass system(s) (4415), orifice(s), air return ducts (4520), connection conduit(s) (4645) and/or surrounding environment(s) (4705).

The said compartment blower(s) (4665) can be, and without limitation, effectively directly and/or indirectly connected and/or removably connected to, and communicate with, one or more of any suitable and effective filter(s) (4675) or compartment air flow filter(s) (4675), all in a manner known to those skilled in the art. It is preferred, without limitation, that air/gas(s) first enters and/or passes through the said one or more compartment blower(s) (4665) before passing through the one or more compartment air flow filter(s) (4675) and entering the agent flow compartment(s) (4630). However, and without limitation, air/gas(s) can also enter the compartment blower(s) (4665) and pass through into the agent flow compartment(s) (4630), after passing through the one or more compartment air flow filter(s) (4675). Without being limited, the compartment air flow filter(s) (4675) can be located in or at one or more of any suitable and effective location(s). According to FIG. 22, and without limitation, any suitable and effective air/gas(s) can enter the one or more compartment airflow filter(s) (4675), flow through one or more of any suitable compartment air inlet(s) (4745) or any other suitable conduit(s), to the one or more suitable compartment blower(s) (4665), and then flow through one or more of any suitable compartment flow tube(s) (4725) or any other suitable conduit(s), and into the one or more agent flow compartment(s) (4630).

Alternatively, and without limitation, the one or more compartment blower(s) (4665) can also be suitably and effectively and removably mounted to, interfaced with, and/or located at, the one or more of the said agent outlet(s) (4670) and/or air/gas(s) exhaust orifice(s) (4671), where the compartment blower(s) (4665) can be interfaced, connected, designed, and/or configured, in a manner known to those skilled in the art, to effectively vacuum, suction, and/or pull, the air/gas(s) and/or deployed agent(s) (4510) through and/or out of at least the agent flow compartment(s) (4630), but preferably both the deployed agent generator(s) (4620) and the agent flow compartment(s) (4630). It is also preferred, without limitation, that in this configuration at least the air/gas(s) that are supplied to the deployed agent generator(s) (4620) are effectively filtered by one or more air flow injection filter(s) (4603). It is more preferred, without limitation, that in this configuration at least the air/gas(s) that are supplied to the deployed agent generator(s) (4620) are effectively filtered by one or more air flow injection filter(s) (4603), and other air/gas(s) that may also be supplied to the agent flow compartment(s) (4630), is also effectively filtered by one or more compartment air flow filter(s) (4675).

Without being limited, the air/gas(s) and deployed agent(s) (4510) can flow through one or more of the said connection conduit(s) (4645) that can connect, communicate, and/or terminate, with one or more of any suitable and effective hose connector(s) (4640), that can effectively removably connect and communicate with one or more additional suitable and effective hose connector(s) (4640) that can effectively connect, removably connect, interface, removably interface, and/or communicate, with one or more of any suitable and effective airflow bulkhead fitting(s) (4680) such as, but not limited to, any suitable and effective bulkhead fitting(s) (4680) that are known to those skilled in the art.

Also, and without being limited, the one or more said airflow bulkhead fitting(s) (4680) described in the present invention can include and communicate with at least one suitable and effective hose connector(s) (4640) that connects and communicates with at least one front fitting plate(s) (4650), all in a manner known to those skilled in the art. It is preferred, without limitation, that the said various hose connector(s) (4640) are any suitable Tri-clamp adapter(s) and Tri-clamp connector(s) known to those skilled in the art.

In an even more detailed aspect of the present invention, and without being limited, the airflow bulkhead fitting(s) (4680) can include various part(s) and component(s) such as, but not limited to, at least one of any suitable and effective, front fitting plate(s) (4650), gasket(s) (4660), rear fitting plate(s) (4685), threaded bolt(s) (4655), and threaded nut(s) (4710). Without being limited, the front fitting plate(s) (4650) can interface with the at least one of any, wall(s) (4695), of and/or belonging to, one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). It is preferred, without limitation that the at least one of any effective seal(s) and/or gasket(s) (4660) is effectively located between the front fitting plate(s) (4650) and the said wall(s) (4695). Without being limited, the various part(s) and component(s) such as, but not limited to, at least one of any suitable and effective, front fitting plate(s) (4650), gasket(s) (4660), rear fitting plate(s) (4685), threaded bolt(s) (4655), and threaded nut(s) (4710), can be any suitable and effective, size(s), design(s), diameter(s), shape(s), geometry(s), length(s), width(s), height(s), and/or thickness(s), and can have any suitable and effective thread pattern(s) and thread design(s) known in the art, and use any suitable and effective materials for their construction.

Without being limited, one or more of any effectively threaded rod, bolt, and/or screw, hole(s) (not shown) of any suitable size(s) and depth(s), can be effectively located in the front fitting plate(s) (4650), so that one or more of any effective threaded rod(s), bolt(s), and/or screw(s) (Herein called "Threaded Bolt(s)") (4655) can preferably, but without limitation, protrude from the rear fitting plate(s) (4685) located on the other side of the said wall(s) (4695) and through the one or more wall hole(s) (4690) and into and/or through the one or more front fitting plate(s) (4650).

Also, and without being limited, one or more of any suitable, plate(s), bar(s), and/or support(s) (Herein called "Rear Fitting Plate(s)") (4685) are suitably and effectively located, preferably and without limitation, directly opposed to the front fitting plate(s) (4650), on the other side of the wall(s) (4695) from the front fitting plate(s) (4650). Also, and without being limited, one or more of any threaded bolt(s) (4655) with any effective length(s), can protrude from any of the said plate(s) (4685)(4650) and/or protrude in one or more of any effective direction(s), but preferably, and without limitation, protrude from the rear fitting plate(s) (4685) in any effective manner know to those skilled in the art, and through the one or more suitable wall hole(s) (4690) and gasket(s) (4660), and screw and/or thread any effective distance(s) into and/or through the one or more said threaded rod, bolt, and/or screw, hole(s) (not shown), located in the front fitting plate(s) (4650) located on the other side of the wall(s) (4695) from the rear fitting plate(s) (4685). Without being limited, this order can also be reversed from the front fitting plate(s) (4650) to the rear fitting plate(s) (4685). It is preferred, without limitation, that the front fitting plate(s) (4650) are located on the same side(s) of the one or more wall(s) (4695) as the agent dispenser(s) (4505) and the agent flow compartment(s) (4630). It is also preferred, without limitation, that the threaded bolt(s) (4655) are fixed into one or more of any suitable and effective position(s), and cannot turn, as they protrude from the rear fitting plate(s) (4685), all in a manner known to those skilled in the art.

Additionally, and without being limited, the rear fitting plate(s) (4685), threaded bolt(s) (4655), and front fitting plate(s) (4650) are designed in a manner known to those skilled in the art, so that one or more of any suitable nut(s) (4710) can be threaded onto the threaded bolt(s) (4655) and mechanically tightening the nut(s) (4710) from the side of the front fitting plate(s) (4650), causes the rear fitting plate(s) (4685) and the front fitting plate(s) (4650) to tighten effectively against the said wall(s) (4695) and at least one effective hermetic seal(s) to form against the wall(s) (4695) with the said one or more suitable gasket(s) (4660), all in a manner known to those skilled in the art. Without being limited one or more suitable gasket(s) (4660) can also be positioned between the rear fitting plate(s) (4685) and the said wall(s) (4695). Without being limited, any suitable and effective thread pattern(s) and thread design(s) can be used for the various said part(s) and component(s).

Referring to FIG. 22, FIG. 24, and FIGS. 25-27, and without being limited, an even much more detailed description of the one or more agent dispenser(s) (4505) is given. Without being limited, the one or more agent dispenser(s) (4505) can include one or more of any suitable and effective deployed agent(s) generator(s) (4620) that can directly and/or indirectly effectively connect and communicate with at least one aerosol(s), gas(s), and/or vapor(s), collection chamber(s) or agent flow compartment(s) (4630), that can have one or more of any suitable air/gas(s) intake orifice(s) (4673) and/or compartment flow tube(s) (4725), which can directly and/or indirectly connect to and effectively connect and communicate with at least one suitable and effective blower(s), fan(s), and/or air pump(s), and/or otherwise compartment blower(s) (4665) that is effectively connected to and directly and/or indirectly communicates with, and is supplied with, pulls, draws, flows, and/or receives, air/gas(s) and/or deployed agent(s) (4510) from one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520).

Also, and without being limited, the said agent flow compartment(s) (4630) can have one or more of any suitable and effective air/gas exhaust orifice(s) (4671) and/or exhaust outlet(s) (4670), which can be removably and effectively connected to and directly and/or indirectly communicate with, and supply and/or flow the air/gas(s) and/or deployed agent(s) (4510) that are first flowed, moved, and/or deposited into the said agent flow compartment(s) (4630) from the said deployed agent(s) generator(s) (4620), to the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). Without being limited, the agent flow compartment(s) (4630) can also be any suitable and effective, number(s), size(s), shape(s), length(s), width(s), height(s), and/or volume(s), and have one or more of any suitable and effective internal geometry(s) and/or shape(s).

Without being limited, the one or more deployed agent(s) (4510) such as, but not limited to any, gas(s), vapor(s), particle(s), and/or aerosol(s), including one or more of any suitable and effective combination(s) of one or more of any agent(s) (4510) in one or more of any suitable and effective form(s), that are generated or created by and/or within the deployed agent(s) generator(s) (4620), are moved or flowed into the said one or more agent flow compartment(s) (4630) with one or more of any suitable and effective fan(s), blower(s), and/or air pump(s), such as, but not limited to any agent generator blower(s) (4700), that can be located at one or more of any suitable and effective location(s), and can directly and/or indirectly communicate with the one or more deployed agent(s) generator(s) (4620) and/or the one or more agent flow compartment(s) (4630). Without limitation, the said one or more fan(s), blower(s), and/or air pump(s) such as, but not limited to the agent generator blower(s) (4700), can also be effectively located in the said air/gas stream before and/or after the deployed agent(s) generator(s) (4620).

Figure 22:
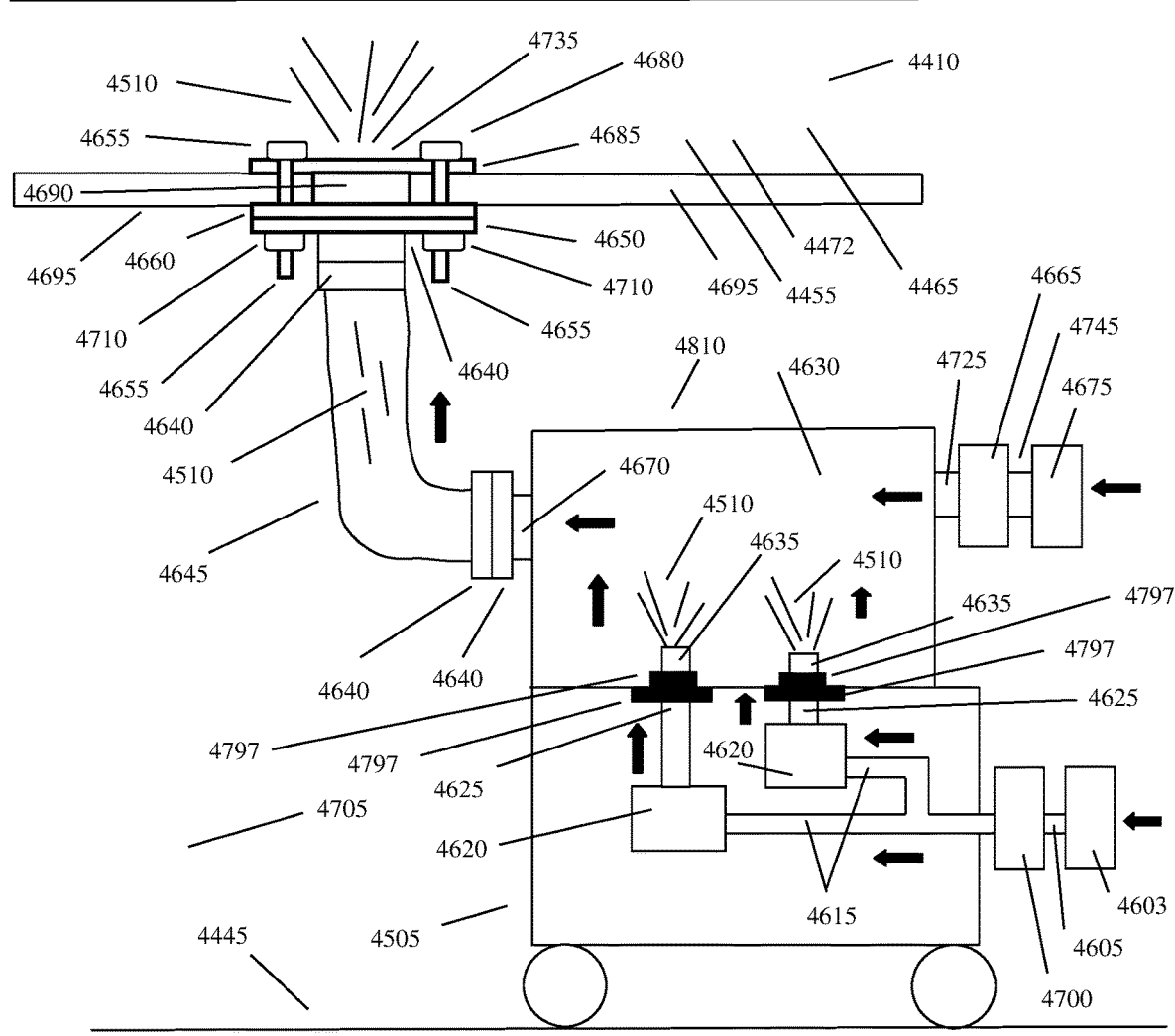
Figure 24:
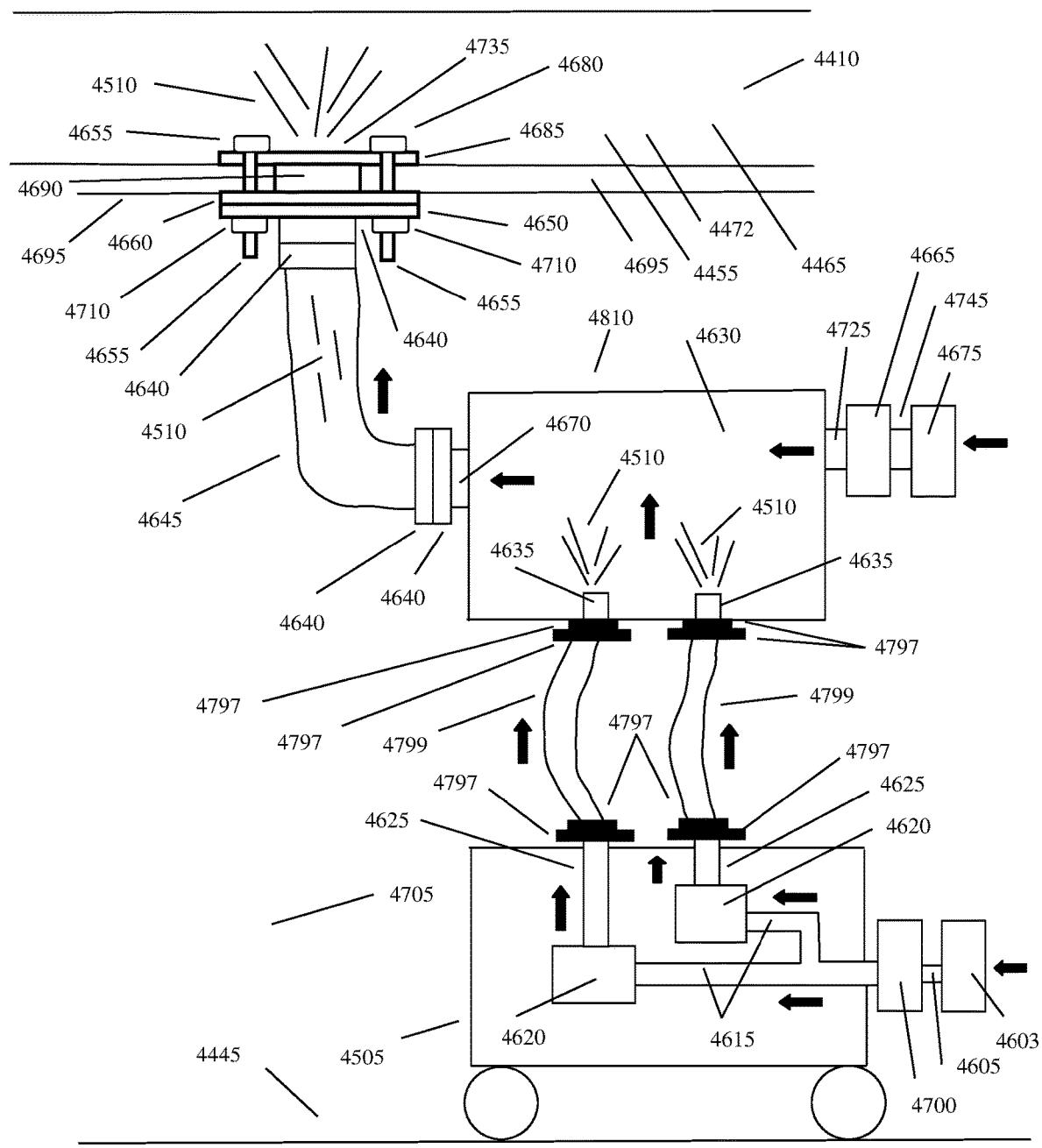
Figure 27:
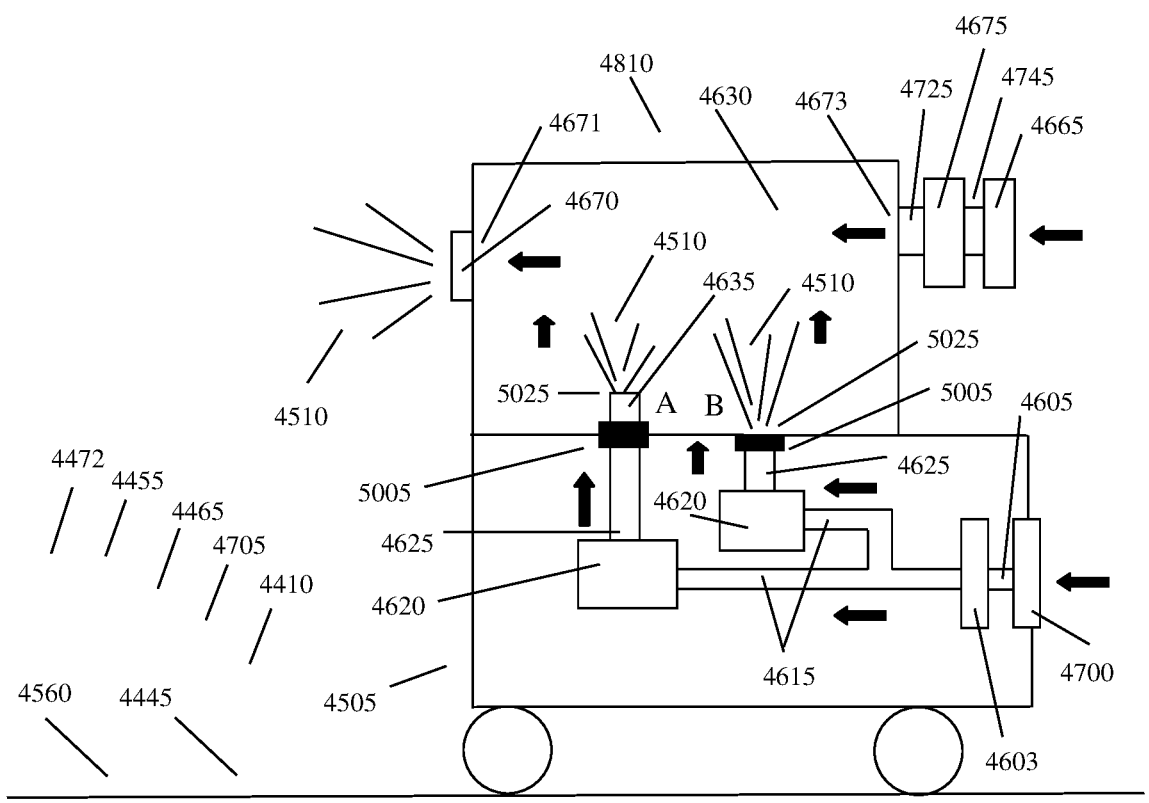
FIG. 27 is a schematic side view of an enhanced deployed agent(s) generator that is positioned in at least one room(s) or targeted area(s), and air/gas(s) from the room are supplied and flowed to and into both the deployed agent(s) generator(s) and the agent flow compartment(s).
Figure 28:
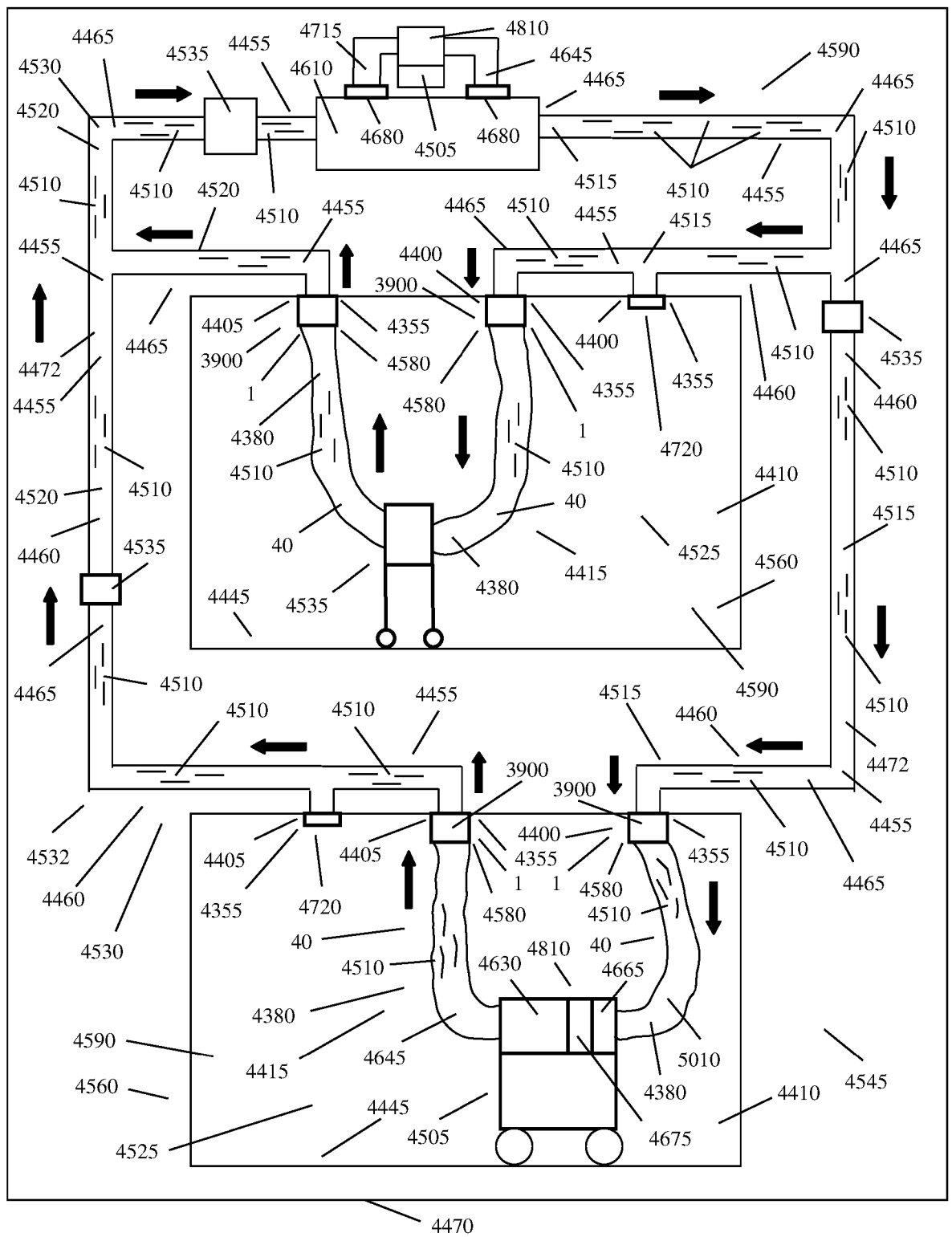
FIG. 28 is a schematic diagram of a two story of building showing at least one room on each floor and the rooms are connected by at least one system of shared air ducts that communicate with at least one HVAC system that supply air to the at least one room on each floor with a duct fan supported on wheels and located in a hose, which connects flow between entry and exit vents on a second floor.

According to FIGS. 22, 24, and 27, and without limitation, it is preferred without limitation, that the air/gas(s) that are supplied to the both the deployed agent(s) generator(s) (4620) and the agent flow compartment(s) (4630), are sourced from the same and/or shared one or more location(s) and/or area(s), such as, but not limited to any atmosphere or environment that surrounds the one or more agent dispenser(s) (4505).

However, according to FIG. 25, and without limitation, it is more preferred without limitation, that the air/gas(s) that are supplied to the agent flow compartment(s) (4630) can be sourced from the same and/or communicating, one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that the deployed agent(s) (4510) is deployed into and/or through. In addition, and without limitation, the air/gas(s) that is supplied to the deployed agent(s) generator(s) (4620) can be sourced from the environment or atmosphere that surrounds the one or more agent dispenser(s) (4505).

Also, however, according to FIG. 26, and without limitation, it is even more preferred without limitation, that the air/gas(s) that are supplied to both the deployed agent(s) generator(s) (4620) and the agent flow compartment(s) (4630) can be sourced from the same and/or communicating, one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that the deployed agent(s) (4510) is deployed into and/or through.

Without being limited, air, gas(s), and/or deployed agent(s) (4510), can be flowed and/or moved into the one or more deployed agent(s) generator(s) (4620) and/or the one or more agent flow compartment(s) (4630), and/or into both the one or more deployed agent(s) generator(s) (4620) and the one or more agent flow compartment(s) (4630), to move, pump, and/or flow, the deployed agent(s) (4510) out of, through, and/or from, the said deployed agent(s) generator(s) (4620) and into the agent flow compartment(s) (4630), and/or then out of, through, and/or from, the agent flow compartment(s) (4630), and into the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). For example, and with reference to FIGS. 25-26, and without limitation, the air/gas(s) and/or deployed agent(s) (4510) can be recirculated back through the deployed agent(s) generator(s) (4620) and/or the agent flow compartment(s) (4630) from the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that are connected to and/or communicate with, any output of any deployed agent(s) (4510) and/or air/gas(s) flow(s) from the agent flow compartment(s) (4630).

With reference to FIG. 26, it is preferred, without limitation, that the air/gas(s) and/or deployed agent(s) (4510) can be recirculated back through both the deployed agent(s) generator(s) (4620) and the agent flow compartment(s) (4630) from the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that are connected to and/or communicate with, any output of any deployed agent(s) (4510) and/or air/gas(s) flow(s) from the agent flow compartment(s) (4630).

Also, with reference to FIG. 26, and without being limited, instead of sharing one or more common supply conduit(s) (5020) that communicate with the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), the deployed agent(s) generator(s) (4620) and the agent flow compartment(s) (4630) can also have their own separate and/or designated one or more conduit(s) (not shown) that can connect to the said one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s)

(4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40) (4380), vent bypass system(s) (4415), orifice(s), and/or air return ducts (4520). Without being limited, one or more of any suitable and effective fan(s), blower(s), and/or air pump(s), can be suitably and effectively located and operated to push, pull, and/or vacuum, the said air/gas(s) through the deployed agent(s) generator(s) (4620) and the agent flow compartment(s) (4630), as well as out of the agent flow compartment(s) (4630), at one or more of any suitable and effective speed(s), velocity(s), and/or air/gas volume(s) per unit of time.

Also referring to FIG. 26, and without being limited, the one or more outlet end(s) and/or agent outlet(s)) (5025) of the one or more of any pipe(s), hose(s), and/or conduit(s) (4625) (4635), that first connect to and communicate with the deployed agent(s) generator(s) (4620), and then communicate with and terminate into and/or empty into, the agent flow compartment(s) (4630), can be located, positioned, and/or angled, at one or more of any suitable and effective, location(s), pattern(s), height(s), and/or angles, within the agent flow compartment(s) (4630) as denoted by letter (A). Also, without being limited, the one or more outlet end(s) (Herein called "Agent Outlet(s)") (5025) of the one or more of any pipe(s), hose(s), and/or conduit(s) (4625) (4635) that connect to and communicate with the deployed agent(s) generator(s) (4620), and then communicate with and terminate into and/or empty into the agent flow compartment(s) (4630), can be located, positioned, and/or angled, at one or more of any suitable and effective, location(s), pattern(s), height(s), and/or angles, that is flush with and/or at and/or about the same elevation as, the floor of the agent flow compartment(s) (4630) as denoted by letter (B).

Without being limited, one or more of any suitable pipe(s), hose(s), and/or conduit(s), that can enter the agent flow compartment(s) (4630), and/or directly and/or indirectly connect in a manner known to those skilled in the art to form one or more assembly(s) of suitable conduit(s) that can effectively connect and allow the deployed agent(s) generator(s) (4620) to effectively communicate with the agent flow compartment(s) (4630), such as, but not limited to any flow outlet(s) (4635) and/or deployed agent exhaust pipe(s) (4625), can suitably and effectively interface with, pierce, connect with, intersect with, and/or enter, the agent flow compartment(s) (4630) with and/or through one or more of any suitable and effective pipe connector(s) (5005) known to those skilled in the art, such as, but not limited to any, suitable and effective wipe seal assembly(s), pipe and/or hose joining apparatus(s), pipe and/or hose interface mechanism(s), hose and/or pipe connector(s), and/or conduit joining component(s).

Without being limited, the one or more deployed agent(s) generator(s) (4620) can be located in one or more of any suitable and effective, location(s) and/or area(s). It is preferred, without limitation, that the one or more deployed agent(s) generator(s) (4620), are suitably located in one or more area(s) and/or location(s) that are remote and/or separate from the said agent flow compartment(s) (4630), and the deployed agent(s) generator(s) (4620) can effectively communicate with the agent flow compartment(s) (4630). The deployed agent(s) generator(s) (4620) can also be, without limitation, effectively located at one or more of any suitable and effective distance(s) from the agent flow compartment(s) (4630).

Without being limited, the deployed agent(s) generator(s) (4620) can effectively communicate with the agent flow compartment(s) (4630) using one or more of any suitable and effective means known to those skilled in the art such as, but not limited to any suitable and effective, pipe(s), conduit(s), and/or hose(s) (4615), that can be flexible, semi-rigid, and/or rigid. Without being limited, one or more of any suitable and effective means, part(s), and/or component(s), known to those skilled in the art can be used to removably connect the deployed agent(s) generator(s) (4620) to the agent flow compartment(s) (4630), so that they can effectively communicate and air/gas(s) and/or deployed agent(s) (4510) can flow and/or move from the deployed agent(s) generator(s) (4620) and into the agent flow compartment(s) (4630).

Referring to FIG. 27, and without limitation, the one or more agent dispenser(s) (4505) as described in the present invention, can also be located and operated in one or more of any suitable, space(s), chamber(s), enclosure(s), area(s), and/or room(s) (4410). In this particular embodiment, and without limitation, the said one or more agent dispenser(s) (4505) can be located in any sized space(s), that is preferably and without limitation at least suitable, and both the deployed agent(s) generator(s) (4620) and the agent flow compartment(s) (4630), can instead be supplied with air/gas(s) and/or deployed agent(s) (4510) that would be sourced from the atmosphere and/or environment that surrounds the agent dispenser(s) (4505).

Referring to FIGS. 16, 17, 19, and 21, and without being limited, any air/gas(s) flow and/or deployed agent(s) (4510) that is circulated within and/or through the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), vent bypass system(s) (4415), and/or air return ducts (4520), can be effectively flowed, moved, and/or circulated through, the one or more of any agent dispenser(s) (4505), and more specifically through one or more of any suitable and effective part(s) and component(s) of the one or more agent dispenser(s) (4505), and even more specifically through one or more of any, agent generator blower(s) (4700), deployed agent generator(s) (4620), agent flow compartment(s) (4630), compartment blower(s) (4665), agent outlet(s) (4670), connection conduit(s) (4645), and/or airflow bulkhead fitting(s) (4680), that are a part of and/or communicate with one or more of any agent dispenser(s) (4505).

According to FIGS. 16, 17, 19, and 21, and without limitation, one or more of any suitable and effective, pipe(s), conduit(s), and/or hose(s) (Herein called "Agent Dispenser Inlet Connection(s)" (4715), can also suitably and effectively connect and communicate with one or more of any agent dispenser(s) (4505) in a manner known to those skilled in the art, and supply the said agent dispenser(s) (4505) with any suitable and effective supply and/or flow of any air/gas(s) and/or deployed agent(s) (4510). It is preferred, without limitation, that the supply and/or flow of the said air/gas(s) and/or deployed agent(s) (4510) are sourced from the one or more of any suitable and effective, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s)

(4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). Also, and without being limited, the said supply and/or flow of the said air/gas(s) and/or deployed agent(s) (4510) can be supplied to and flow through the one or more deployed agent generator(s) (4620) and/or agent flow compartment(s) (4630), where the deployed agent(s) (4510) and air/gas(s) can then flow through and/or out of, one or more location(s), outlet(s), part(s), and/or component(s) such as, but not limited to any, connection conduit(s) (4645). Without being limited the one or more connection conduit(s) (4645) can suitably and effectively connect and communicate with one or more of any suitable and effective, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), all in a manner known to those skilled in the art.

It is preferred, without limitation, that the one or more of any agent dispenser(s) (4505) are therefore hermetically sealed and connected to the said one or more of any suitable and effective, location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), and at least one effective communicating and closed loop air/gas(s) flow system(s) is formed, where the said flow of air/gas(s) and/or deployed agent(s) (4510) is moved, circulated, and flowed, through the one or more of the said any, location(s), room(s), enclosure(s), space(s), part(s), equipment(s), component(s), structure(s), conduit(s), HVAC parts and equipment(s) (4465), HVAC unit(s) (4610), and/or air duct(s) (4455), in addition to also being moved, circulated, and flowed, effectively and suitably through the one or more of any agent dispenser(s) (4505), and even more preferably and without limitation, at least through either and/or both of the one or more, agent flow compartment(s) (4630) and/or the deployed agent generator(s) (4620), as well as any vent bypass system(s) (4415) that are connected to the closed, effectively sealed, and communicating system of any of the said, location(s), room(s), enclosure(s), space(s), part(s), equipment(s), component(s), structure(s), conduit(s), HVAC parts and equipment(s) (4465), HVAC unit(s) (4610), and/or air duct(s) (4455), through which the air/gas(s) and/or deployed agent (s) can move, circulate, and flow through.

Alternatively, and referring to FIGS. 18 and 20, and without limitation, the one or more of any agent dispenser(s) (4505) can be hermetically sealed and connected to the said one or more of any suitable and effective, location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), and at least one effective communicating and open loop air/gas(s) flow system(s) is formed, where the said flow of air/gas(s) and/or deployed agent(s) (4510) is moved, circulated, and flowed, through the one or more of the said any, location(s), room(s), enclosure(s), space(s), part(s), equipment(s), component(s), structure(s), conduit(s), HVAC parts and equipment(s) (4465), HVAC unit(s) (4610), and/or air duct(s) (4455), in addition to also being moved, circulated, and flowed, effectively and suitably through the one or more of any agent dispenser(s) (4505), and even more preferably and without limitation, at least through either and/or both of the one or more, agent flow compartment(s) (4630) and/or the deployed agent generator(s) (4620), as well as any vent bypass system(s) (4415), where the air/gas(s) and deployed agent(s) (4510) is eventually flowed and/or vented into any environment, area, and/or atmosphere, at one or more of any suitable and effective location(s) that is outside of and/or separate from the said open loop air/gas(s) flow system(s).

Referring to FIGS. 16-17, 19, and 23, and according to an embodiment, and without limitation, an enhanced vent bypass system(s) (4415) (4790) is shown, where the enhanced vent bypass system (4415) (4790) can also include and communicate with one or more of any, including one or more of any suitable and effective combination(s) of any, suitable and effective, part(s), component(s), and/or equipment(s), such as, but not limited to any, means to filter any air/gas(s) (4600) including any means to filter airborne chemicals from any air/gas(s), means to flow, blow, or move any air/gas(s) (4535), means to heat any air/gas(s) (4740), means to dehumidify any air/gas(s) (4800), and/or agent dispenser(s) (4505). Without being limited, the one or more said part(s), component(s), and/or equipment(s), can be connected and/or located in any suitable and effective order(s), and be activated and/or used for one or more of any purposes, and at any suitable and effective time(s), and for any effective duration of time(s). Without limitation, the said part(s), component(s), and/or equipment(s), can also suitably and effectively connect and communicate with one or more of any conduit(s) and/or hose(s) (40)(4380) that connect with and/or are a part of any enhanced vent bypass system(s) (4415) (4790). Also without being limited, the one or more conduit(s) or hose(s) (40)(4380) can form, take the place of, and/or function as, the one or more agent dispenser inlet connection(s) (4715) and connection conduit(s) (4645) that can connect and communicate with the one or more agent dispenser(s) (4505).

Figure 23:
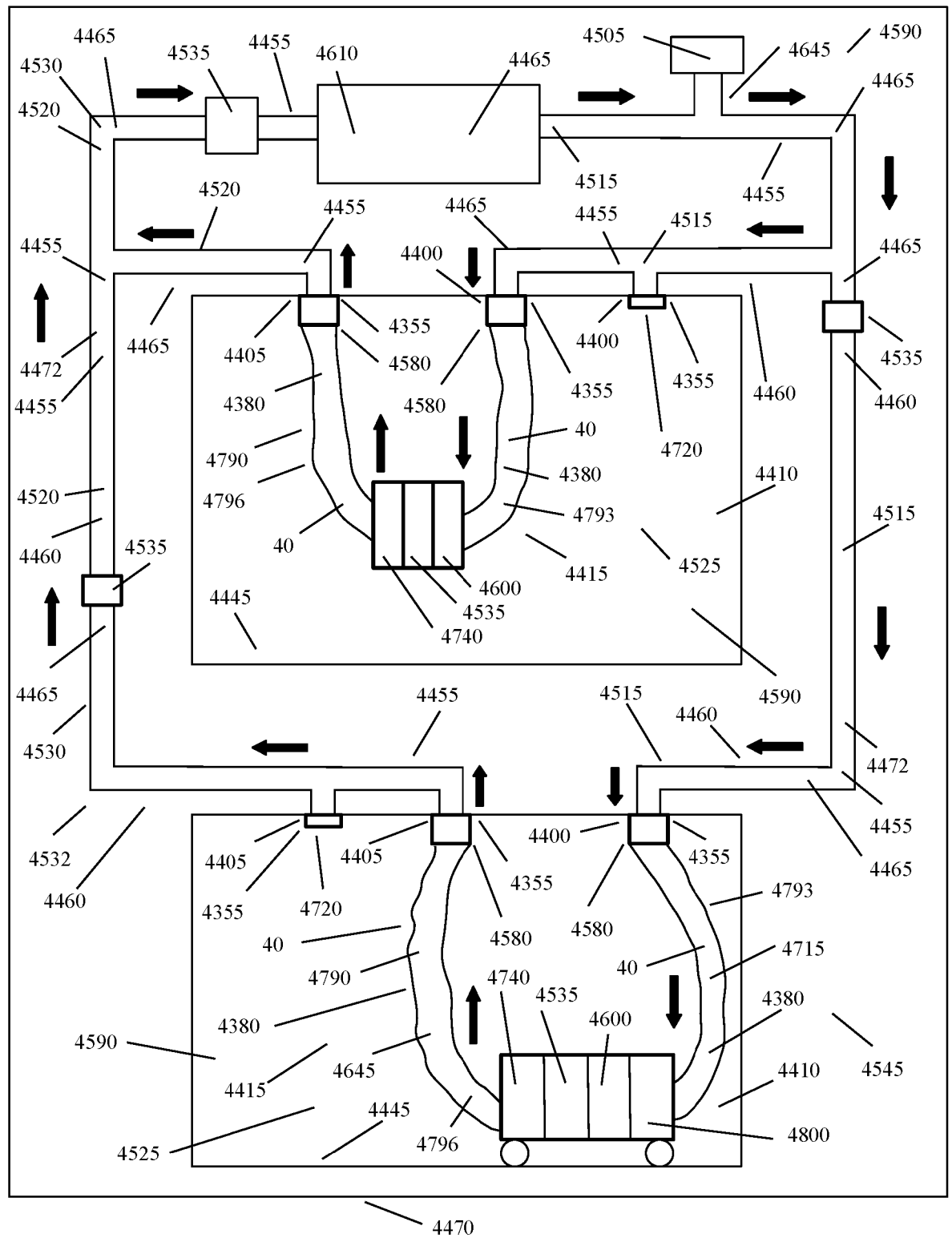

More specifically, and referring to FIG. 23, and without limitation, one or more enhanced vent bypass system(s) (4790) can be used in any building(s) and structure(s) including, but not limited to any multi-story building(s) (4470), where one or more hoses and/or conduits (40)(4380) (Herein called "Air/gas(s) Supply Conduit(s)") (4793), that connect to one part of an enhanced vent bypass system (4790) that covers and seals any air/gas(s) vent(s) (4400) that supply air/gas(s) in and/or into any area(s) and/or room(s) (4410) is first connected to and communicates with one or more of any, air filter(s) (4600), blower(s) (4535), air/gas(s) flow heater(s) (4740), dehumidifier(s) (4800), and/ or agent dispenser(s) (4505), in any suitable and effective combination(s), and is then connected and sealed to one or more hoses and/or conduits (40)(4380) (Herein called "Air/ gas(s) Exit Conduit(s)") (4796), that connects to another part of the enhanced vent bypass system(s) (4790) that covers and seals the air/gas(s) vent(s) (4405) that vent, remove, and/or provide an exit for air/gas(s) to leave, any area(s) and/or room(s) (4410).

In one example, and without being limited, at least one suitable and effective duct fan(s) (4535) is suitably and effectively connected to and communicates with the vent bypass system (4415), and more specifically with the various conduit(s) or hose(s) (40)(4380) of the vent bypass system (4415). The said duct fan(s) (4535) are operated at least during the deployment of the deployed agent(s) (4510) by the agent dispenser(s) (4505), and assist with moving or flowing air/gas(s) and/or the deployed agent(s) (4510) effectively through various location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520).

In another example, and without being limited, after the deployed agent(s) (4510) are finished being administered by the agent dispenser(s) (4505), at least one of any suitable and effective, duct fan(s) (4535), air heater(s) (4740), dehumidifier(s) (4800), and/or air filter(s) such as, but not limited to any, airborne chemical absorbing filter(s) and/or HEPA filter(s), can be suitably and effectively connected to and communicate with the one or more of any conduit(s) or hose(s) (40)(4380) of the vent bypass system (4415). Without limitation, the said duct fan(s) (4535), dehumidifier(s) (4800), and/or air/gas(s) heater(s) is operated and effectively flows and moves air/gas(s), and preferably and without limitation, effectively heated air/gas(s), through various location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), for purposes including, but not limited to effectively, drying, dehumidifying, and/or removing any, gas(s), chemical(s), humidity, and/or vapor(s), from these various, surface(s), space(s), location(s), part(s), and/or equipment(s). Without being limited, the one or more duct fan(s) (4535) and/or air heater(s) (4740) can be operated for one or more of any suitable and effective duration(s) of time. Also without being limited, the duct heater(s) can heat the air/gas(s) that are flowed and moved, to any suitable and effective temperatures, but at least preferably, and without limitation, to any effective temperature above 70 degree Fahrenheit.

According to FIG. 22 and FIG. 24-28, and without being limited, one or more of any suitable and effective booster chamber(s) (4810), having one or more of any suitable and effective, size(s), shape(s), geometry(s), length(s), width(s), height(s), diameter(s), design(s), and/or complexity(s), can suitably and effectively directly and/or indirectly communicate with one or more of any suitable and effective agent dispenser(s) (4505) known to those skilled in the art.

Without being limited, the booster chamber(s) (4810) can include various parts and components such as, but not limited to, one or more of any, suitable chamber(s) and/or agent flow compartment(s) (4630) that can directly and/or indirectly connect and communicate with one or more of any suitable and effective deployed agent generator(s) (4620) using, through, and/or by way of, one or more of any suitable and effective, conduit(s) and/or deployed agent exhaust pipe(s) (4625). Also, without being limited, one or more of any deployed agent(s) (4510) of any suitable and effective, quantity(s), density(s), number density(s), volume(s), and/or concentration(s), for one or more of any suitable and effective unit(s) of time(s), can effectively flow from the one or more deployed agent generator(s) (4620), through the one or more deployed agent exhaust pipe(s) (4625), and into the one or more agent flow compartment(s) (4630). The one or more deployed agent exhaust pipe(s) (4625) can, and without limitation, suitably and effectively directly and/or indirectly connect with the agent flow compartment(s) (4630) in any suitable and effective manner known to those skilled in the art.

In one example, and without limitation, the deployed agent exhaust pipe(s) (4625) can connect to and/or removably connect to, and communicate with, the agent flow compartment(s) (4630) using one or more of any suitable and effective means known to those skilled in the art. In another example, and without limitation, the deployed agent exhaust pipe(s) (4625) can connect to and/or removably connect to, and effectively communicate with, the agent flow compartment(s) (4630) using one or more of any suitable and effective coupling(s) (4797). In still another example, and without limitation, the deployed agent exhaust pipe(s) (4625) can connect to and/or removably connect to, and effectively communicate with, the agent flow compartment(s) (4630) using one or more of any suitable and effective pipe connector(s) (5005).

Without being limited, the one or more of any, deployed agent exhaust pipe(s) (4625), coupling(s) (4797), and/or pipe connector(s) (5005), can effectively directly and/or indirectly interface and/or communicate with one or more of any agent flow compartment(s) (4630). Also, without being limited, one or more of any suitable, flow outlet(s) (4635) and/or deployed agent exhaust pipe(s) (4625), can suitably and effectively interface with, pierce, connect with, intersect with, and/or enter, the agent flow compartment(s) (4630) at one or more of any suitable and effective location(s). Without being limited, the one or more of any deployed agent(s) (4510), can flow through and/or out of, one or more of any suitable and effective, deployed agent exhaust pipe(s) (4625), flow outlet(s) (4635), and/or agent outlet(s) (5025), and into the one or more agent flow compartment(s) (4630), at one or more of any suitable and effective, speed(s), rate(s), velocity(s), quantity(s), and/or concentration(s).

Without being limited, the agent flow compartment(s) (4630) are effectively directly and/or indirectly connected to one or more of any suitable and effective source(s) of positive pressure air/gas(s) flow(s) and/or negative pressure air/gas(s) flow(s), such as, but not limited to any suitable and effective, blower(s), fan(s), and/or compartment blower(s) (4665), located at one or more of any suitable and effective location(s). In one example, and without limitation, air/gas(s) enters the agent flow compartment(s) (4630) by first flowing through one or more of any suitable and effective filter(s) or compartment airflow filter(s) (4675) and then through one or more of any suitable and effective compartment blower(s) (4665), before flowing into the agent flow compartment(s) (4630). In a preferred example, and without limitation, air/gas(s) enters the agent flow compartment(s) (4630) by first flowing through the one or more of any suitable and effective compartment blower(s) (4665) and then through one or more of any suitable and effective filter(s) or compartment airflow filter(s) (4675) before flowing into the agent flow compartment(s) (4630). Without being limited, air/gas(s) can first travel through one or more of any suitable and effective pre-filter(s) (not shown) before entering the compartment blower(s) (4665), all in a manner known to those skilled in the art.

Once the said air/gas(s) have flowed into and through the agent flow compartment(s) (4630), the said air/gas(s) and deployed agent(s) (4510) can flow out of the agent flow compartment(s) (4630), through one or more of any suitable and effective air/gas(s) exhaust orifice(s) (4671), and preferably and without limitation, through and out of one or more of any suitable and effective agent outlet(s) (4670). Without being limited, the air/gas(s) and deployed agent(s) (4510) can flow into one or more of any location(s), area(s), and/or space(s), and/or flow through one or more of any effective hose connector(s) (4640) and into and through one or more suitable and effective connection conduit(s) (4645) and then be delivered and/or deployed into or to, any suitable and effective, location(s), space(s), and/or area(s).

According to FIGS. 1-28, and without limitation, the one or more of any suitable and effective, vent bypass system(s) (4415) can also include, but is not limited to, any one or more of any suitable and effective, portable automated vent cover(s) (3900) and vent cover system(s) (1).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of treating at least one HVAC system, one of said at least one HVAC system includes a source of conditioned air, a conditioned outlet for flowing the conditioned air to a plurality of supply vents through a plurality of supply ducts and a conditioned inlet for receiving air from a plurality of return vents through a plurality of return ducts, the plurality of supply and return ducts supply a plurality of enclosed spaces, comprising the steps of:

providing at least one device for supplying a treatment substance for application to an inside surface of the at least one HVAC system, one of said at least one device includes a device outlet and a device inlet, said device outlet is connected to one of the plurality of return vents, said device inlet is connected to one of said plurality of supply vents;

connecting some of the plurality of supply vents to some of the plurality of return vents with a plurality of tubes in the plurality of enclosed spaces; and flowing said treatment substance from said device outlet of said at least one device into the one of the plurality of return vents, through at least one of the plurality of return ducts into the conditioned inlet, receiving a flow from the conditioned outlet, through the plurality of supply ducts and the one of the at least one supply vent through said device inlet, said treatment substance is for at least one of sanitizing, disinfecting and sterilizing, the plurality of enclosed spaces not being exposed to said treatment substance.

2. The method of treating at least one HVAC system of claim 1, further comprising the step of:

providing a booster fan having an inlet and an outlet, said inlet of said booster fan is connected to another one of the plurality of supply vents, said outlet of said booster fan is connected to another one of the plurality of return vents.

3. The method of treating at least one HVAC system of claim 1, further comprising the step of:

providing a booster fan having an inlet and an outlet, said inlet of said booster fan receives flow from one of the plurality of supply ducts or one of the plurality of return ducts, said outlet of said booster fan provides a flow to one of the plurality of supply ducts or one of the plurality of return ducts.

4. The method of treating at least one HVAC system of claim 1, further comprising the step of:

providing a second device supplying a treatment substance, said second device includes a second inlet and a second outlet, said second inlet is connected to another one of the plurality of supply vents, said second outlet is connected to another one of the plurality of return vents.

5. The method of treating at least one HVAC system of claim 1, further comprising the step of:

providing a filter having an inlet and an outlet, said inlet of said filter receives flow from one of the plurality of supply ducts or one of the plurality of return ducts, said outlet of said filter provides a flow to one of the plurality of supply ducts or one of the plurality of return ducts.

6. A method of treating at least one HVAC system, one of said at least one HVAC system includes a source of conditioned air, a conditioned outlet for flowing the conditioned air to a plurality of supply vents through a plurality of supply ducts and a conditioned inlet for receiving air from a plurality of return vents through a plurality of return ducts, the plurality of supply and return ducts supply a plurality of enclosed spaces, comprising the steps of:

providing at least one device for supplying a treatment substance for application to an inside surface of the at least one HVAC system, one of said at least one device includes a device outlet and a device inlet, said device outlet is connected to one of the plurality of return vents, one of said at least one device is located in one of said plurality of enclosed spaces;

connecting some of the plurality of supply vents to some of the plurality of return vents with a plurality of tubes in the plurality of enclosed spaces; and flowing said treatment substance from said device outlet of said at least one device into the one of the plurality of return vents, through at least one of the plurality of return ducts into the conditioned inlet, receiving a flow from the conditioned outlet, through the plurality of supply ducts and the one of the at least one supply vent through a dehumidifier, said treatment substance is at least one for sanitizing, disinfecting and sterilizing, the plurality of enclosed spaces not being exposed to said treatment substance.

7. The method of treating at least one HVAC system of claim 6, further comprising the step of:

providing a booster fan having an inlet and an outlet, said inlet of said booster fan is connected to another one of the plurality of supply vents, said outlet of said booster fan is connected to another one of the plurality of return vents.

8. The method of treating at least one HVAC system of claim 6, further comprising the step of:
providing a booster fan having an inlet and an outlet, said inlet of said booster fan receives flow from one of the plurality of supply ducts or one of the plurality of return ducts, said outlet of said booster fan provides a flow to one of the plurality of supply ducts or one of the plurality of return ducts.

9. The method of treating at least one HVAC system of claim 6, further comprising the step of:
providing a second device supplying a treatment substance, said second device includes a second inlet and a second outlet, said second inlet is connected to another one of the plurality of supply vents, said second outlet is connected to another one of the plurality of return vents.

10. The method of treating at least one HVAC system of claim 6, further comprising the step of:
providing a filter having an inlet and an outlet, said inlet of said filter receives flow from one of the plurality of supply ducts or one of the plurality of return ducts, said outlet of said filter provides a flow to one of the plurality of supply ducts or one of the plurality of return ducts.

11. A method of treating at least one HVAC system, one of said at least one HVAC system includes a source of conditioned air, an conditioned outlet for flowing the conditioned air to a plurality of supply vents through a plurality of supply ducts and a conditioned inlet for receiving air from a plurality of return vents through a plurality of return ducts, the plurality of supply and return ducts supply a plurality of enclosed spaces, comprising the steps of:
providing at least one device for supplying a treatment substance for application to an inside surface of the at least one HVAC system, one of said at least one device includes a device outlet and a device inlet, one of said at least one device is located in one of said plurality of enclosed spaces;
a booster chamber having a booster inlet, and a booster outlet, said booster inlet is connected to said device outlet of one of said at least one device, said booster chamber accelerating the flow of said treatment substance to said booster outlet, said booster outlet is connected to one of the plurality of return vents;

connecting some of the plurality of supply vents to some of the plurality of return vents with a plurality of tubes in the plurality of enclosed spaces; and flowing said treatment substance from said booster outlet into one of the plurality of return vents, through at least one of the plurality of return ducts into the conditioned inlet, receiving a flow from the conditioned outlet, through the plurality of supply ducts and the one of the at least one supply vent to said device inlet, said treatment substance is at least one for sanitizing, disinfecting and sterilizing, the plurality of enclosed spaces not being exposed to said treatment substance with the exception of the one of the plurality of enclosed spaces.

12. The method of treating at least one HVAC system of claim 11, further comprising the step of:

connecting one end of at least one connection conduit to said output of said device, connecting an opposing end of said connection conduit to said booster inlet.

13. The method of treating at least one HVAC system of claim 11, further comprising the step of:

providing said booster chamber with an additional booster input for obtaining a flow of gas.

14. The method of treating at least one HVAC system of claim 11, further comprising the step of:

providing a booster fan having an inlet and an outlet, said inlet of said booster fan is connected to another one of the plurality of supply vents, said outlet of said booster fan is connected to another one of the plurality of return vents.

15. The method of treating at least one HVAC system of claim 11, further comprising the step of:

providing a booster fan having an inlet and an outlet, said inlet of said booster fan receives flow from one of the plurality of supply ducts or one of the plurality of return ducts, said outlet of said booster fan provides a flow to one of the plurality of supply ducts or one of the plurality of return ducts.

16. The method of treating at least one HVAC system of claim 11, further comprising the step of:

providing a second device supplying a treatment substance, said second device includes a second inlet and a second outlet, said second inlet is connected to another one of the plurality of supply vents, said second outlet is connected to another one of the plurality of return vents.

17. The method of treating at least one HVAC system of claim 11, further comprising the step of:

providing a filter having an inlet and an outlet, said inlet of said filter receives flow from one of the plurality of supply ducts or one of the plurality of return ducts, said outlet of said filter provides a flow to one of the plurality of supply ducts or one of the plurality of return ducts.

* * * * *